(12) United States Patent
Bundock

(10) Patent No.: US 12,215,329 B2
(45) Date of Patent: Feb. 4, 2025

(54) METHODS OF TARGETED GENETIC ALTERATION IN PLANT CELLS

(71) Applicant: Keygene N.V., Wageningen (NL)

(72) Inventor: Paul Bundock, Wageningen (NL)

(73) Assignee: Keygene N.V., Wageningen (NL)

( * ) Notice: Subject to any disclaimer, the term of this patent is extended or adjusted under 35 U.S.C. 154(b) by 0 days.

(21) Appl. No.: 16/485,806

(22) PCT Filed: Feb. 15, 2018

(86) PCT No.: PCT/EP2018/053775
§ 371 (c)(1),
(2) Date: Aug. 14, 2019

(87) PCT Pub. No.: WO2018/149915
PCT Pub. Date: Aug. 23, 2018

(65) Prior Publication Data
US 2020/0190527 A1    Jun. 18, 2020

(30) Foreign Application Priority Data
Feb. 15, 2017  (NL) ..................... 2018381

(51) Int. Cl.
*C12N 15/82* (2006.01)
*C12N 9/22* (2006.01)
*C12N 9/78* (2006.01)
*C12N 15/11* (2006.01)

(52) U.S. Cl.
CPC ........... *C12N 15/8213* (2013.01); *C12N 9/22* (2013.01); *C12N 9/78* (2013.01); *C12N 15/11* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 10,077,453 | B2 | 9/2018 | Liu et al. | |
| 11,371,051 | B2* | 6/2022 | Bundock | C12N 9/22 |
| 2015/0166980 | A1* | 6/2015 | Liu | C12N 9/22 435/227 |
| 2016/0208243 | A1 | 7/2016 | Zhang et al. | |
| 2019/0367933 | A1* | 12/2019 | Bundock | A01H 4/00 |

FOREIGN PATENT DOCUMENTS

| CN | 110214183 A * | 9/2019 | ............... A61P 35/00 |
| EP | 3115457 A1 * | 1/2017 | ............ C12N 15/102 |
| WO | WO2015/089406 A1 | 6/2015 | |
| WO | WO2015/139008 A1 | 9/2015 | |
| WO | WO-2015133554 A1 * | 9/2015 | ............... C12N 9/22 |

OTHER PUBLICATIONS

Liu, Chenggang. "Reconstitution of Metabolic Pathway in Nicotiana benthamiana." Plant Metabolic Engineering. Humana, New York, NY, 2022. 29-33. (Year: 2022).*
Dalal, Jyoti, et al. "A novel gateway-compatible binary vector series (PC-GW) for flexible cloning of multiple genes for genetic transformation of plants." Plasmid 81 (2015): 55-62. (Year: 2015).*
Chan, Kin, and Dmitry A. Gordenin. "Clusters of multiple mutations: incidence and molecular mechanisms." Annual review of genetics 49 (2015): 243. (Year: 2015).*
Steinert, Highly efficient heritable plant genome engineering using Cas9 orthologues from *Streptococcus thermophilus* and *Staphylococcus aureus*, The Plant Journal, 2015, Issue 84, pp. 1295-1305 (Year: 2015).*
Li, Generation of Targeted Point Mutations in Rice by a Modified CRISPR/Cas9 System, Molecular Plant 10, 526-529, Dec. 8, 2016 (Year: 2016).*
Jingying Li et al:Targeted Point Mutations in Rice by a Modified CRISPR/Cas9 System, Molecular Plant. vol. 10, (Dec. 8, 2016), pp. 526-529.
Li Jian-Feng et al: Multiplex and homologous recombination-mediated genome editing in *Arabidopsis* and *Nicotiana benthamiana* using guide RNA and Cas9, Nature Biotechnology, vol. 31, No. 8, (Jun. 23, 2013), pp. 688-691.
Xingliang Ma et al: CRISPR/Cas9 Platforms for Genome Editing in Plants: Developments and Applications, Molecular Plant, vol. 9, No. 7, (Jul. 1, 2016), pp. 961-974.
Simon Schiml et al: Revolutionizing plant biology: multiple ways of genome engineering by CRISPR/Cas, Plant Methods, vol. 12, No. 1, (Jan. 28, 2016).
Komor, A.C., et al., 2016. Programmable editing of a target base in genomic DNA without double-stranded DNA cleavage. Nature, 533(7603), p. 420.
Yang, et al. "Engineering and optimising deaminase fusions for genome editing." Nature communications 7 (2016): 13330.
Gaudelli et al. "Programmable base editing of A• T to G• C in genomic DNA without DNA cleavage." Nature 551.7681 (2017): 464.

* cited by examiner

*Primary Examiner* — Weihua Fan
*Assistant Examiner* — Brian James Sullivan
(74) *Attorney, Agent, or Firm* — Troutman Pepper Hamilton Sanders LLP

(57) ABSTRACT

The current invention relates to methods of targeted genetic alteration in cells, preferably plant cells, as well as to plant cells and plants thus obtained using at least a fusion protein comprising a site-specific nuclease domain and a deaminase domain, or a construct encoding the same. The method also provides for a composition and a kit comprising a combination of a first fusion protein comprising a cytosine deaminase domain and a second fusion protein comprising an adenine deaminase domain, preferably for use in the method of the invention. The method provides for targeted alteration of a DNA duplex in plant cells with increased efficacy.

18 Claims, 12 Drawing Sheets
Specification includes a Sequence Listing.

Figure 1A

*DNA sequence encoding the rAPOBEC-Cas9-UGI fusion protein (SEQ ID NO: 1)*

ATGGGTAGCAGCCATCATCATCACCATCATATGAGCAGCGAAACAGGTCCGGTTGCAGTTGATCCGACCCTGCGTC
GTCGTATTGAACCGCATGAATTTGAAGTTTTTTTTGATCCGCGTGAGCTGCGTAAAGAAACCTGTCTGCTGTATGAA
ATTAACTGGGGTGGTCGTCATAGCATTTGGCGTCATACCAGCCAGAATACCAATAAACATGTGGAAGTGAACTTCA
TCGAGAAATTTACCACCGAACGTTATTTTTGTCCGAATACCCGTTGTAGCATTACCTGGTTTCTGAGCTGGTCACCGT
GTGGTGAATGTAGCCGTGCAATTACCGAATTTCTGAGCCGTTATCCGCATGTTACCCTGTTTATCTATATTGCCCGTC
TGTATCATCATGCAGATCCGCGTAATCGTCAGGGTCTGCGTGATCTGATTAGCAGCGGTGTTACCATTCAGATTATG
ACCGAACAAGAAAGCGGTTATTGCTGGCGTAATTTTGTGAATTATAGCCCGAGCAATGAAGCACATTGGCCTCGCT
ATCCGCATCTGTGGGTTCGTCTGTATGTTCTGGAACTGTATTGTATTATTCTGGGTCTGCCTCCGTGTCTGAATATTC
TGCGTCGTAAACAGCCGCAGCTGACCTTTTTTACCATTGCACTGCAGAGCTGTCATTATCAGCGTCTGCCACCGCAT
ATTCTGTGGGCAACAGGTCTGAAAAGCGGTAGCGAAACACCGGGTACAAGCGAAAGCGCAACACCGGAAAGCGA
CAAAAAATACAGCATTGGTCTGGACATTGGTACCAACAGCGTGGGCTGGGCCGTGATCACCGACGAGTACAAG
GTGCCCAGCAAGAAGTTCAAGGTGCTGGGCAACACCGACCGCCACAGCATCAAGAAGAACCTGATCGGCGCCC
TGCTGTTCGACAGCGGCGAGACCGCCGAGGCCACCCGCCTGAAGCGCACCGCCCGCCGCTACACCCGCCGC
AAGAACCGCATCTGCTACCTGCAGGAGATCTTCAGCAACGAGATGGCCAAGGTGGACGACAGCTTCTTCCACCG
CCTGGAGGAGAGCTTCCTGGTGGAGGAGGACAAGAAGCACGAGCGCCACCCCATCTTCGGCAACATCGTGGAC
GAGGTGGCCTACCACGAGAAGTACCCCACCATCTACCACCTGCGCAAGAAGCTGGTGGACAGCACCGACAAGG
CCGACCTGCGCCTGATCTACCTGGCCCTGGCCCACATGATCAAGTTCCGCGGCCACTTCCTGATCGAGGGCGACC
TGAACCCCGACAACAGCGACGTGGACAAGCTGTTCATCCAGCTGGTGCAGACCTACAACCAGCTGTTCGAGGAG
AACCCCATCAACGCCAGCGGCGTGGACGCCAAGGCCATCCTGAGCGCCCGCCTGAGCAAGAGCCGCCGCCTGG
AGAACCTGATCGCCCAGCTGCCCGGCGAGAAGAAGAACGGCCTGTTCGGCAACCTGATCGCCCTGAGCCTGGGC
CTGACCCCCAACTTCAAGAGCAACTTCGACCTGGCCGAGGACGCCAAGCTGCAGCTGAGCAAGGACACCTACGA
CGACGACCTGGACAACCTGCTGGCCCAGATCGGCGACCAGTACGCCGACCTGTTCCTGGCCGCCAAGAACCTGA
GCGACGCCATCCTGCTGAGCGACATCCTGCGCGTGAACACCGAGATCACCAAGGCCCCCCTGAGCGCCAGCATG
ATCAAGCGCTACGACGAGCACCACCAGGACCTGACCCTGCTGAAGGCCCTGGTGCGCCAGCAGCTGCCCGAGAA
GTACAAGGAGATCTTCTTCGACCAGAGCAAGAACGGCTACGCCGGCTACATCGACGGCGGCGCCAGCCAGGAG
GAGTTCTACAAGTTCATCAAGCCCATCCTGGAGAAGATGGACGGCACCGAGGAGCTGCTGGTGAAGCTGAACC
GCGAGGACCTGCTGCGCAAGCAGCGCACCTTCGACAACGGCAGCATCCCCCACCAGATCCACCTGGGCGAGCTG
CACGCCATCCTGCGCCGCCAGGAGGACTTCTACCCCTTCCTGAAGGACAACCGCGAGAAGATCGAGAAGATCCT
GACCTTCCGCATCCCCTACTACGTGGGCCCCCTGGCCCGCGGCAACAGCCGCTTCGCCTGGATGACCCGCAAGAG
CGAGGAGACCATCACCCCCTGGAACTTCGAGGAGGTGGTGGACAAGGGCGCCAGCGCCCAGAGCTTCATCGAG
CGCATGACCAACTTCGACAAGAACCTGCCCAACGAGAAGGTGCTGCCCAAGCACAGCCTGCTGTACGAGTACTT
CACCGTGTACAACGAGCTGACCAAGGTGAAGTACGTGACCGAGGGCATGCGCAAGCCCGCCTTCCTGAGCGGC
GAGCAGAAGAAGGCCATCGTGGACCTGCTGTTCAAGACCAACCGCAAGGTGACCGTGAAGCAGCTGAAGGAG
GACTACTTCAAGAAGATCGAGTGCTTCGACAGCGTGGAGATCAGCGGCGTGGAGGACCGCTTCAACGCCAGCC
TGGGCACCTACCACGACCTGCTGAAGATCATCAAGGACAAGGACTTCCTGGACAACGAGGAGAACGAGGACAT
CCTGGAGGACATCGTGCTGACCCTGACCCTGTTCGAGGACCGCGAGATGATCGAGGAGCGCCTGAAGACCTAC
GCCCACCTGTTCGACGACAAGGTGATGAAGCAGCTGAAGCGCCGCCGCTACACCGGCTGGGGCCGCCTGAGCC
GCAAGCTTATCAACGGCATCCGCGACAAGCAGAGCGGCAAGACCATCCTGGACTTCCTGAAGAGCGACGGCTTC
GCCAACCGCAACTTCATGCAGCTGATCCACGACGACAGCCTGACCTTCAAGGAGGACATCCAGAAGGCCCAGGT
GAGCGGCCAGGGCGACAGCCTGCACGAGCACATCGCCAACCTGGCCGGCAGCCCCGCCATCAAGAAGGGCATC
CTGCAGACCGTGAAGGTGGTGGACGAGCTGGTGAAGGTGATGGGCCGCCACAAGCCCGAGAACATCGTGATC

Figure 1B

GAGATGGCCCGCGAGAACCAGACCACCCAGAAGGGCCAGAAGAACAGCCGCGAGCGCATGAAGCGCATCGAG
GAGGGCATCAAGGAGCTGGGCAGCCAGATCCTGAAGGAGCACCCCGTGGAGAACACCCAGCTGCAGAACGAG
AAGCTGTACCTGTACTACCTGCAGAACGGCCGCGACATGTACGTGGACCAGGAGCTGGACATCAACCGCCTGAG
CGACTACGACGTGGACCACATCGTGCCCCAGAGCTTCCTGAAGGACGACAGCATCGACAACAAGGTGCTGACCC
GCAGCGACAAGAACCGCGGCAAGAGCGACAACGTGCCCAGCGAGGAGGTGGTGAAGAAGATGAAGAACTACT
GGCGCCAGCTGCTGAACGCCAAGCTGATCACCCAGCGCAAGTTCGACAACCTGACCAAGGCCGAGCGCGGCGG
CCTGAGCGAGCTGGACAAGGCCGGCTTCATCAAGCGCCAGCTGGTGGAGACCCGCCAGATCACCAAGCACGTG
GCCCAGATCCTGGACAGCCGCATGAACACCAAGTACGACGAGAACGACAAGCTGATCCGCGAGGTGAAGGTGA
TCACCCTGAAGAGCAAGCTGGTGAGCGACTTCCGCAAGGACTTCCAGTTCTACAAGGTGCGCGAGATCAACAAC
TACCACCACGCCCACGACGCCTACCTGAACGCCGTGGTGGGCACCGCCCTGATCAAGAAGTACCCCAAGCTGGA
GAGCGAGTTCGTGTACGGCGACTACAAGGTGTACGACGTGCGCAAGATGATCGCCAAGAGCGAGCAGGAGAT
CGGCAAGGCCACCGCCAAGTACTTCTTCTACAGCAACATCATGAACTTCTTCAAGACCGAGATCACCCTGGCCAA
CGGCGAGATCCGCAAGCGCCCCCTGATCGAGACCAACGGCGAGACCGGCGAGATCGTGTGGGACAAGGGCCG
CGACTTCGCCACCGTGCGCAAGGTGCTGAGCATGCCCCAGGTGAACATCGTGAAGAAGACCGAGGTGCAGACC
GGCGGCTTCAGCAAGGAGAGCATCCTGCCCAAGCGCAACAGCGACAAGCTGATCGCCCGCAAGAAGGACTGGG
ACCCCAAGAAGTACGGCGGCTTCGACAGCCCCACCGTGGCCTACAGCGTGCTGGTGGTGGCCAAGGTGGAGAA
GGGCAAGAGCAAGAAGCTGAAGAGCGTGAAGGAGCTGCTGGGCATCACCATCATGGAGCGCAGCAGCTTCGA
GAAGAACCCCATCGACTTCCTGGAGGCCAAGGGCTACAAGGAGGTGAAGAAGGACCTGATCATCAAGCTGCCC
AAGTACAGCCTGTTCGAGCTGGAGAACGGCCGCAAGCGCATGCTGGCCAGCGCCGGCGAGCTGCAGAAGGGC
AACGAGCTGGCCCTGCCCAGCAAGTACGTGAACTTCCTGTACCTGGCCAGCCACTACGAGAAGCTGAAGGGCAG
CCCCGAGGACAACGAGCAGAAGCAGCTGTTCGTGGAGCAGCACAAGCACTACCTGGACGAGATCATCGAGCAG
ATCAGCGAGTTCAGCAAGCGCGTGATCCTGGCCGACGCCAACCTGGACAAGGTGCTGAGCGCCTACAACAAGC
ACCGCGACAAGCCCATCCGCGAGCAGGCCGAGAACATCATCCACCTGTTCACCCTGACCAACCTGGGCGCCCCC
GCCGCCTTCAAGTACTTCGACACCACCATCGACCGCAAGCGCTACACCAGCACCAAGGAGGTGCTGGACGCCAC
CCTGATCCACCAGAGCATCACCGGTCTGTATGAAACCCGTATTGATCTGAGCCAGCTGGGTGGTGAT*AGCGGTG*
*GTAGCACCAATCTGAGCGATATCATTGAAAAAGAAACCGGCAAACAGCTGGTGATTCAAGAAAGCATTCTGATGC*
*TGCCTGAAGAAGTGGAAGAAGTTATTGGTAATAAACCGGAAAGCGATATTCTGGTTCATACCGCATATGATGAAA*
*GCACCGATGAAAATGTTATGCTGAGCGGTGGTTCC*CCGAAAAAAAAACGTAAAGTTTAA

*rAPOBEC-Cas9-UGI fusion protein (SEQ ID NO: 2)*

MGSSHHHHHH*MSSETGPVAVDPTLRRRIEPHEFEVFFDPRELRKETCLLYEINWGGRHSIWRHTSQNTNKHVEVNFIE*
*KFTTERYFCPNTRCSITWFLSWSPCGECSRAITEFLSRYPHVTLFIYIARLYHHADPRNRQGLRDLISSGVTIQIMTEQESGY*
*CWRNFVNYSPSNEAHWPRYPHLWVRLYVLELYCIILGLPPCLNILRRKQPQLTFFTIALQSCHYQRLPPHILWATG*LKSGS
ETPGTSESATPESDKKYSIGLDIGTNSVGWAVITDEYKVPSKKFKVLGNTDRHSIKKNLIGALLFDSGETAEATRLKRTA
RRRYTRRKNRICYLQEIFSNEMAKVDDSFFHRLEESFLVEEDKKHERHPIFGNIVDEVAYHEKYPTIYHLRKKLVDSTDK
ADLRLIYLALAHMIKFRGHFLIEGDLNPDNSDVDKLFIQLVQTYNQLFEENPINASGVDAKAILSARLSKSRRLENLIAQ
LPGEKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDGTE
ELLVKLNREDLLRKQRTFDNGSIPHQIHLGELHAILRRQEDFYPFLKDNREKIEKILTFRIPYYVGPLARGNSRFAWMTR
KSEETITPWNFEEVVDKGASAQSFIERMTNFDKNLPNEKVLPKHSLLYEYFTVYNELTKVKYVTEGMRKPAFLSGEQK
KAIVDLLFKTNRKVTVKQLKEDYFKKIECFDSVEISGVEDRFNASLGTYHDLLKIIKDKDFLDNEENEDILEDIVLTLTLFE
DREMIEERLKTYAHLFDDKVMKQLKRRRYTGWGRLSRKLINGIRDKQSGKTILDFLKSDGFANRNFMQLIHDDSLTF
KEDIQKAQVSGQGDSLHEHIANLAGSPAIKKGILQTVKVVDELVKVMGRHKPENIVIEMARENQTTQKGQKNSRER

Figure 1C

MKRIEEGIKELGSQILKEHPVENTQLQNEKLYLYYLQNGRDMYVDQELDINRLSDYDVDHIVPQSFLKDDSIDNKVLT
RSDKNRGKSDNVPSEEVVKKMKNYWRQLLNAKLITQRKFDNLTKAERGGLSELDKAGFIKRQLVETRQITKHVAQIL
DSRMNTKYDENDKLIREVKVITLKSKLVSDFRKDFQFYKVREINNYHHAHDAYLNAVVGTALIKKYPKLESEFVYGDY
KVYDVRKMIAKSEQEIGKATAKYFFYSNIMNFFKTEITLANGEIRKRPLIETNGETGEIVWDKGRDFATVRKVLSMPQ
VNIVKKTEVQTGGFSKESILPKRNSDKLIARKKDWDPKKYGGFDSPTVAYSVLVVAKVEKGKSKKLKSVKELLGITIME
RSSFEKNPIDFLEAKGYKEVKKDLIIKLPKYSLFELENGRKRMLASAGELQKGNELALPSKYVNFLYLASHYEKLKGSPED
NEQKQLFVEQHKHYLDEIIEQISEFSKRVILADANLDKVLSAYNKHRDKPIREQAENIIHLFTLTNLGAPAAFKYFDTTID
RKRYTSTKEVLDATLIHQSITGLYETRIDLSQLGGD<u>SGGSTNLSDIIEKETGKQLVIQESILMLPEEVEEVIGNKPESDILVH
TAYDESTDENVMLSGGS</u>PKKKRKV

*DNA sequence encoding the TadA-Cas9 D10A-NLS fusion protein (SEQ ID NO: 3)*

*ATGTCCGAGGTCGAGTTCTCTCATGAGTACTGGATGAGGCACGCTCTCACTCTTGCTAAAAGAGCTTGGGACGAGA
GAGAGGTTCCAGTTGGAGCTGTTTTGGTGCACAACAACCGTGTGATTGGCGAAGGATGGAACAGGCCAATTGGAA
GGCATGATCCAACTGCTCACGCTGAGATTATGGCCCTTAGACAAGGTGGACTCGTGATGCAGAACTACAGGCTTAT
CGACGCCACTCTCTACGTGACACTTGAGCCATGTGTTATGTGCGCTGGTGCCATGATTCACTCCAGGATTGGAAGG
GTTGTGTTCGGAGCTAGAGATGCTAAAACTGGCGCTGCCGGATCTCTCATGGATGTGCTTCATCATCCTGGGATGA
ACCACAGGGTTGAGATCACTGAGGGAATCCTTGCTGATGAGTGCGCTGCTCCTGTCTGATTTTTTCAGGATGAG
GCGTCAAGAGATCAAGGCCCAGAAGAAGGCTCAGTCCTCTACTGA*TCTGGCGGATCTTCTGGTGGGTCATCTGG
ATCTGAAACCCCTGGAACTTCTGAGTCCGCTACTCCAGAATCATCCGGTGGATCTAGTGGTGGTTCT*AGCGAGGTT
GAGTTCAGCCACGAATACTGGATGCGTCACGCACTTACTTTGGCTAAGAGGGCTCGTGATGAGAGGGAAGTTCCT
GTTGGTGCAGTGCTCGTGCTTAACAACAGAGTGATCGGAGAAGGCTGGAATCGTGCTATCGGACTTCATGATCCTA
CCGCACATGCAGAGATCATGGCTTTGAGGCAAGGTGGGCTTGTCATGCAAAATTACCGTCTGATCGACGCTACCTT
GTACGTCACATTCGAGCCTTGCGTGATGTGTGCTGGGCTATGATCCATTCTAGGATCGGTAGAGTGGTGTTCGGT
GTGAGGAATGCTAAGACAGGTGCTGCTGGCTCACTTATGGATGTGTTGCATTACCCCGGCATGAACCACCGTGTGG
AAATTACAGAGGGCATCTTGGCAGATGAGTGTGCCGCTCTTTTGTGCTACTTCTTCAGGATGCCACGTCAGGTGTTC
AACGCTCAAAAGAAGGCCCAATCCAGCACCGA*TTCTGGTGGTAGTAGTGGTGGATCTTCCGGATCAGAGACTCCT
GGTACTAGTGAGTCTGCTACCCCTGAAAGTAGCGGAGGTTCAAGTGGTGGGTCC*GACAAGAAGTACTCTATCGG
ATTGGCTATCGGGACCAACTCTGTTGGATGGGCTGTGATCACTGACGAGTACAAGGTGCCCTCCAAGAAGTTCA
AGGTTCTCGGAAACACCGACAGGCACTCCATCAAGAAGAACCTCATCGGGGCTCTGCTTTTCGATTCAGGTGAA
ACTGCTGAGGCCACCAGGCTTAAGAGAACTGCTAGAAGAAGGTACACCCGTAGGAAGAACAGGATCTGCTACC
TCCAAGAGATCTTCTCCAACGAGATGGCTAAGGTGGACGACTCATTCTTCCACAGGCTCGAAGAGTCCTTCTTGG
TGGAAGAGGATAAGAAGCACGAGAGGCACCCAATCTTCGGGAACATTGTGGATGAAGTGGCCTACCACGAGA
AGTACCCAACCATCTACCACCTGAGGAAGAAGCTCGTTGACTCCACCGATAAGGCTGACCTGAGGCTTATCTACC
TTGCTCTCGCTCACATGATCAAGTTCCGTGGGCACTTCCTTATCGAAGGGGATCTGAACCCAGACAACTCCGATG
TGGACAAGCTGTTCATTCAGCTCGTGCAGACCTACAACCAGCTGTTCGAAGAGAACCCAATCAACGCTTCTGGTG
TGGACGCTAAGGCTATCCTTTCTGCCAGGCTTTCCAAGTCCAGAAGGCTTGAGAACCTGATTGCTCAGCTTCCTG
GGGAGAAGAAGAACGGACTTTTCGGGAACCTGATCGCCCTCTCTCTTGGACTTACTCCAACTTCAAGTCCAACT
TCGACCTCGCTGAGGATGCCAAGCTTCAGCTCTCTAAGGATACCTACGATGACGACCTCGACAACCTCCTTGCTC
AGATTGGAGATCAGTACGCCGACCTTTTCCTCGCCGCTAAAAACCTCTCTGACGCCATCCTCCTGTCCGATATTCT
TAGGGTGAACACCGAGATCACCAAGGCACCACTTTCCGCCTCTATGATCAAGCGTTACGATGAGCACCACCAGG
ACCTCACTTTGCTTAAGGCTCTTGTTAGGCAGCAGCTCCCAGAGAAGTACAAAGAGATTTTCTTCGACCAGTCCA
AGAACGGGTACGCCGGTTATATTGATGGTGGGGCTTCTCAAGAAGAGTTCTACAAGTTCATCAAGCCCATCTTG
GAAAAGATGGACGGGACCGAAGAGTTGCTCGTGAAGCTTAACCGTGAGGACCTTCTTAGGAAGCAGCGAACTT*

Figure 1D

```
TCGACAACGGCTCTATTCCTCACCAGATCCACCTTGGAGAGCTGCACGCTATTCTTCGTAGGCAAGAGGACTTCT
ACCCATTCCTCAAGGACAACCGTGAGAAGATCGAGAAGATTCTCACCTTCAGGATCCCTTACTACGTGGGACCAC
TTGCTAGGGGAAATTCTAGGTTCGCTTGGATGACCCGTAAGAGCGAAGAGACTATCACTCCATGGAACTTCGAA
GAGGTGGTGGACAAAGGTGCTAGCGCTCAGTCTTTCATCGAGAGGATGACTAACTTCGACAAGAACCTGCCAA
ACGAGAAGGTGCTCCCAAAGCACTCTCTGCTCTACGAGTACTTCACCGTGTACAACGAGCTGACCAAGGTCAAG
TATGTGACCGAGGGAATGCGTAAGCCAGCTTTCCTTAGTGGTGAGCAGAAAAAGGCCATCGTGGACCTCTTGTT
CAAGACCAATAGAAAGGTGACCGTGAAGCAGCTCAAAGAGGACTACTTCAAAAAGATCGAGTGCTTCGACTCC
GTCGAGATCTCTGGTGTTGAGGATAGGTTCAACGCCTCCTTGGGAACTTACCACGACCTCCTCAAGATCATCAAG
GATAAGGATTTCTTGGACAACGAGGAAAACGAGGACATCTTGGAGGACATCGTGCTCACCCTTACCTTGTTCGA
GGATCGAGAGATGATCGAGGAACGACTCAAGACCTACGCTCACCTGTTCGATGACAAGGTCATGAAGCAGTTG
AAGAGGCGTAGGTACACTGGATGGGGACGTTTGTCCCGTAAGCTCATTAACGGAATCAGGGACAAGCAGTCCG
GCAAGACTATCCTCGACTTCCTCAAGTCTGATGGGTTCGCCAACCGTAACTTCATGCAGCTCATCCACGACGACA
GCCTGACCTTTAAAGAGGACATCCAAAAGGCCCAGGTGTCCGGTCAAGGCGATTCTCTTCATGAGCACATTGCT
AACCTCGCTGGGTCACCAGCTATCAAGAAGGGAATTCTCCAGACTGTGAAGGTCGTGGACGAGTTGGTTAAGGT
GATGGGTAGACACAAGCCCGAGAACATCGTGATTGAGATGGCTCGTGAGAACCAGACTACTCAGAAGGGGCA
GAAGAACTCCAGGGAACGTATGAAGAGGATCGAAGAGGGGATCAAAGAGCTGGGTCCCAGATTCTTAAAGA
GCACCCAGTTGAGAACACCCAGCTCCAGAATGAGAAGCTCTACCTCTACTACCTGCAGAACGGCAGGGATATGT
ACGTGGACCAAGAGCTGGATATCAACAGGCTCTCCGACTACGATGTTGACCACATTGTGCCCCAGTCTTTCTTGA
AGGACGACTCCATCGACAACAAGGTGCTCACCAGGTCTGATAAGAACCGTGGGAAGTCTGACAACGTGCCATCT
GAAGAGGTCGTGAAGAAGATGAAGAACTACTGGCGTCAGCTCCTCAACGCCAAGCTTATTACTCAGAGGAAGT
TCGACAACTTGACCAAGGCTGAGCGTGGTGGACTTTCCGAACTTGATAAGGCCGGATTCATCAAGAGGCAGCTC
GTGGAAACTAGGCAGATCACTAAGCACGTGGCCCAGATCTTGGACTCTAGGATGAACACCAAGTACGACGAGA
ACGACAAGCTCATCCGTGAGGTGAAGGTCATCACCCTCAAGAGCAAGCTGGTGTCCGATTTCAGAAAGGACTTC
CAATTCTACAAGGTGAGAGAGATCAACAACTACCATCACGCTCACGACGCTTACCTTAACGCTGTTGTTGGAACC
GCTCTCATCAAAAAGTACCCCAAGCTCGAGTCCGAGTTCGTGTACGGTGATTACAAGGTGTACGACGTGCGTAA
GATGATCGCCAAGTCAGAGCAAGAGATCGGTAAGGCTACCGCCAAGTATTTCTTCTACTCCAACATCATGAATTT
CTTCAAGACTGAGATCACCCTCGCCAACGGGGAGATTAGAAAGAGGCCACTTATCGAGACTAACGGCGAGACT
GGTGAAATCGTGTGGGATAAGGGAAGAGACTTCGCCACTGTGCGTAAGGTGTTGTCTATGCCACAGGTGAACA
TCGTCAAGAAAACCGAGGTTCAGACCGGCGGGTTCTCCAAAGAATCTATCCTTCCAAAGAGGAACTCCGACAAG
CTGATCGCTAGGAAGAAGGATTGGGACCCAAAAAAGTACGGTGGGTTCGATTCTCCAACCGTGGCTTACTCTGT
TCTTGTTGTGGCCAAGGTTGAGAAGGGGAAGTCTAAGAAACTCAAGTCCGTGAAAGAGCTGCTCGGGATCACT
ATCATGGAAAGGTCCAGCTTCGAGAAGAATCCAATCGATTTCCTCGAGGCCAAGGGCTACAAAGAGGTGAAGA
AGGACCTTATCATCAAGCTCCCCAAGTACAGCCTCTTCGAGTTGGAGAACGGACGTAAGAGGATGCTTGCTTCT
GCTGGGGAACTTCAGAAGGGAAACGAACTCGCTCTGCCCTCTAAGTACGTGAACTTCCTGTACCTCGCTTCCCAC
TACGAGAAGCTTAAGGGATCTCCAGAGGATAACGAGCAAAAGCAGCTTTTCGTCGAGCAGCACAAGCACTACC
TCGACGAGATTATCGAGCAGATCTCCGAGTTCTCCAAGCGTGTGATTCTCGCTGATGCCAACTTGGACAAGGTGT
TGAGCGCTTACAACAAGCACCGTGACAAGCCAATTAGAGAGCAGGCTGAGAACATCATCCACCTGTTCACTCTC
ACCAACCTTGGTGCTCCAGCTGCCTTTAAGTACTTCGATACCACCATCGACCGTAAGAGGTACACCTCCACCAAA
GAGGTTTTGGACGCTACCCTTATCCACCAGTCCATCACTGGACTTTACGAGACTAGGATCGACCTCTCACAGCTCG
GTGGTGACTCTGGTGGATCACCAAAGAAGAAGAGGAAGGTCTAA
```

Figure 1E

TadA-Cas9 D10A-NLS fusion protein *(SEQ ID NO: 4)*

MSEVEFSHEYWMRHALTLAKRAWDEREVPVGAVLVHNNRVIGEGWNRPIGRHDPTAHAEIMALRQGGLVMQNYR
LIDATLYVTLEPCVMCAGAMIHSRIGRVVFGARDAKTGAAGSLMDVLHHPGMNHRVEITEGILADECAALLSDFFRMR
RQEIKAQKKAQSSTD<u>SGGSSGGSSGSETPGTSESATPESSGGSSGGS</u>SEVEFSHEYWMRHALTLAKRARDEREVPVGAV
LVLNNRVIGEGWNRAIGLHDPTAHAEIMALRQGGLVMQNYRLIDATLYVTFEPCVMCAGAMIHSRIGRVVFGVRNAK
TGAAGSLMDVLHYPGMNHRVEITEGILADECAALLCYFFRMPRQVFNAQKKAQSSTD<u>SGGSSGGSSGSETPGTSESAT
PESSGGSSGGS</u>DKKYSIGLAIGTNSVGWAVITDEYKVPSKKFKVLGNTDRHSIKKNLIGALLFDSGETAEATRLKRTAR
RRYTRRKNRICYLQEIFSNEMAKVDDSFFHRLEESFLVEEDKKHERHPIFGNIVDEVAYHEKYPTIYHLRKKLVDSTDKA
DLRLIYLALAHMIKFRGHFLIEGDLNPDNSDVDKLFIQLVQTYNQLFEENPINASGVDAKAILSARLSKSRRLENLIAQL
PGEKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDGTE
ELLVKLNREDLLRKQRTFDNGSIPHQIHLGELHAILRRQEDFYPFLKDNREKIEKILTFRIPYYVGPLARGNSRFAWMTR
KSEETITPWNFEEVVDKGASAQSFIERMTNFDKNLPNEKVLPKHSLLYEYFTVYNELTKVKYVTEGMRKPAFLSGEQK
KAIVDLLFKTNRKVTVKQLKEDYFKKIECFDSVEISGVEDRFNASLGTYHDLLKIIKDKDFLDNEENEDILEDIVLTLTLFE
DREMIEERLKTYAHLFDDKVMKQLKRRRYTGWGRLSRKLINGIRDKQSGKTILDFLKSDGFANRNFMQLIHDDSLTF
KEDIQKAQVSGQGDSLHEHIANLAGSPAIKKGILQTVKVVDELVKVMGRHKPENIVIEMARENQTTQKGQKNSRER
MKRIEEGIKELGSQILKEHPVENTQLQNEKLYLYYLQNGRDMYVDQELDINRLSDYDVDHIVPQSFLKDDSIDNKVLT
RSDKNRGKSDNVPSEEVVKKMKNYWRQLLNAKLITQRKFDNLTKAERGGLSELDKAGFIKRQLVETRQITKHVAQIL
DSRMNTKYDENDKLIREVKVITLKSKLVSDFRKDFQFYKVREINNYHHAHDAYLNAVVGTALIKKYPKLESEFVYGDY
KVYDVRKMIAKSEQEIGKATAKYFFYSNIMNFFKTEITLANGEIRKRPLIETNGETGEIVWDKGRDFATVRKVLSMPQ
VNIVKKTEVQTGGFSKESILPKRNSDKLIARKKDWDPKKYGGFDSPTVAYSVLVVAKVEKGKSKKLKSVKELLGITIME
RSSFEKNPIDFLEAKGYKEVKKDLIIKLPKYSLFELENGRKRMLASAGELQKGNELALPSKYVNFLYLASHYEKLKGSPED
NEQKQLFVEQHKHYLDEIIEQISEFSKRVILADANLDKVLSAYNKHRDKPIREQAENIIHLFTLTNLGAPAAFKYFDTTID
RKRYTSTKEVLDATLIHQSITGLYETRIDLSQLGGD<u>SGGS</u>*PKKKRKV**

Figure 2

LIN5 sgRNA1 (SEQ ID NO: 5)

GGAGTGATCAAAAGTCCCACATCGATCAGGTGATATATAGCAGCTTAGTTTATATAATGATAGA
GTCGACATAGCGATTGCCTGACGATGAAATTAAGAAGTTTTAGAGCTAGAAATAGCAAGTTAAA
ATAAGGCTAGTCCGTTATCAACTTGAAAAAGTGGCACCGAGTCGGTGCTTTTTTT

LIN5 sgRNA2 (SEQ ID NO: 6)

GGAGTGATCAAAAGTCCCACATCGATCAGGTGATATATAGCAGCTTAGTTTATATAATGATAGA
GTCGACATAGCGATTGTTCATCGTCAGGTAATACATGTTTTAGAGCTAGAAATAGCAAGTTAAA
ATAAGGCTAGTCCGTTATCAACTTGAAAAAGTGGCACCGAGTCGGTGCTTTTTTT

ALS2 sgRNA1 (SEQ ID NO: 7)

GGAGTGATCAAAAGTCCCACATCGATCAGGTGATATATAGCAGCTTAGTTTATATAATGATAGA
GTCGACATAGCGATTGCAAGTGCCGAGGAGGATGATGTTTTAGAGCTAGAAATAGCAAGTTAAA
ATAAGGCTAGTCCGTTATCAACTTGAAAAAGTGGCACCGAGTCGGTGCTTTTTTT

ALS2 sgRNA2 (SEQ ID NO: 8)

GGAGTGATCAAAAGTCCCACATCGATCAGGTGATATATAGCAGCTTAGTTTATATAATGATAGA
GTCGACATAGCGATTGCATCCTCCTCGGCACTTGACGTTTTAGAGCTAGAAATAGCAAGTTAAA
ATAAGGCTAGTCCGTTATCAACTTGAAAAAGTGGCACCGAGTCGGTGCTTTTTTT

ALS2 sgRNA3 (SEQ ID NO: 9)

GGAGTGATCAAAAGTCCCACATCGATCAGGTGATATATAGCAGCTTAGTTTATATAATGATAGA
GTCGACATAGCGATTGTTACCGGTCAAGTGCCGAGGGTTTTAGAGCTAGAAATAGCAAGTTAAA
ATAAGGCTAGTCCGTTATCAACTTGAAAAAGTGGCACCGAGTCGGTGCTTTTTTT

ALS2 S640 sgRNA1 (SEQ ID NO: 10)

GGAGTGATCAAAAGTCCCACATCGATCAGGTGATATATAGCAGCTTAGTTTATATAATGATAGA
GTCGACATAGCGATTGGCACCGCCACTGGGAATCATGTTTTAGAGCTAGAAATAGCAAGTTAAA
ATAAGGCTAGTCCGTTATCAACTTGAAAAAGTGGCACCGAGTCGGTGCTTTTTTT

ALS2 S640 sgRNA2 (SEQ ID NO: 11)

GGAGTGATCAAAAGTCCCACATCGATCAGGTGATATATAGCAGCTTAGTTTATATAATGATAGA
GTCGACATAGCGATTGTCTTTGAAAGCACCGCCACTGTTTTAGAGCTAGAAATAGCAAGTTAAA
ATAAGGCTAGTCCGTTATCAACTTGAAAAAGTGGCACCGAGTCGGTGCTTTTTTT

ALS2 S640 sgRNA3 (SEQ ID NO: 12)

GGAGTGATCAAAAGTCCCACATCGATCAGGTGATATATAGCAGCTTAGTTTATATAATGATAGA
GTCGACATAGCGATTGCTACCGATGATTCCCAGTGGGTTTTAGAGCTAGAAATAGCAAGTTAAA
ATAAGGCTAGTCCGTTATCAACTTGAAAAAGTGGCACCGAGTCGGTGCTTTTTTT

Figure 3

| | | |
|---|---|---|
| KG10098 + KG10075 | CCTGACGATGAAATTAAGAAAGG (SEQ ID NO: 13) | |
| | .....T................ | 0.8% |
| | .T...T................ | 0.08% |
| | TT...T................ | 0.07% |
| | T..................... | 0.01% |
| | | |
| KG10126 + KG10075 | CCTGACGATGAAATTAAGAAAGG (SEQ ID NO: 14) | |
| | .....T................ | 0.08% |
| | T..................... | 0.04% |
| | TT...T................ | 0.02% |
| | .....T.--------------. | 0.01% |
| | T....T................ | 0.01% |
| | | |
| KG10098 + KG10252 | CCGATGTATTACCTGACGATGAA (SEQ ID NO: 15) | |
| | ...............A..A..  | 0.48% |
| | ...................A.. | 0.36% |
| | ...........A..A..A..   | 0.3% |
| | | |
| KG10436 + KG10075 | CCTGACGATGAAATTAAGAAAGG (SEQ ID NO: 16) | |
| | .....G................ | 0.12% |
| | .......G.............. | 0.02% |
| | | |
| KG10098 + KG10436 + KG10075 | CCTGACGATGAAATTAAGAAAGG (SEQ ID NO: 17) | |
| | .....T................ | 0.35% |
| | .....G................ | 0.15% |
| | .....T.G.............. | 0.02% |

Figure 4

```
WT      ATGTATTACCTGACGATGAA                    (SEQ ID NO: 18)
Line 1  ATGTATTAYCTGAYGATGAA    KG10075         (SEQ ID NO: 19)
Line 2  ATGTATTACYTGAYGATGAA    KG10075         (SEQ ID NO: 20)
Line 3  ATGTATTAYYTGAYGATGAA    KG10075         (SEQ ID NO: 21)
Line 4  ATGTATTACCTGACRATRAA    KG10252         (SEQ ID NO: 22)
Line 5  ATGTATTACCTRACRATRAA    KG10252         (SEQ ID NO: 23)
Line 6  ATGTATTACCTAACAATAAA    KG10252         (SEQ ID NO: 24)
```

Figure 5

Codon P184

```
                              ---------------------- ALS sgRNA1
                     ---------------------- ALS sgRNA3
5'     TGCTATTACCGGTCAAGTGCCGAGGAGGATGATTGGTAC         (SEQ ID NO: 25)
3'     ACGATAATGGCCAGTTCACGGCTCCTCCTACTAACCATG         (SEQ ID NO: 26)
       ALS sgRNA2 ----------------------
```

Codon S640

```
                         ---------------------- S640 sgRNA3
5'     TGTTCTACCGATGATTCCCAGTGGCGGTGCTTTCAAAGA         (SEQ ID NO: 27)
3'     ACAAGATGGCTACTAAGGGTCACCGCCACGAAAGTTTCT         (SEQ ID NO: 28)
                      ---------------------- S640 sgRNA1
            S640 sgRNA2 ----------------------
```

Figure 6A

```
                              T  G  E  V  P  R  R  M  I  G
P184 ref      TGCTATTACCGGTCAAGTGCCGAGGAGGATGATTGGTAC       (SEQ ID NO: 29)
ALS sgRNA1    .........................T............       P184S
ALS sgRNA1    ..........................T...........       P184L
ALS sgRNA1    ..........................TT..........       P184L
ALS sgRNA1    ...............T.......................      E182stop
ALS sgRNA2    .............................A.........      R185L
ALS sgRNA2    ..............................A........      R185
ALS sgRNA2    .................................A.....      R186L
ALS sgRNA2    ....................................A...     M187I
ALS sgRNA3    ........T..............................      T180I
ALS sgRNA3    .........T.............................      T180
ALS sgRNA3    ........TT.............................      T180I
ALS sgRNA3    ...............T.......................      E182stop
ALS sgRNA3    .........................T............       P184S
ALS sgRNA3    ..........................T...........       P184L
ALS sgRNA3    ..........................TT..........       P184L L  P  M  I  P  S  G  G  A  F  L
S640 ref      TGTTCTACCGATGATTCCCAGTGGCGGTGCTTTCAAAGA       (SEQ ID NO: 30)
S640 sgRNA1   ............A..........................      M637I
S640 sgRNA1   ....................A..................      S640N
S640 sgRNA1   ......................A................      G641S
S640 sgRNA1   .......................A...............      G641D
S640 sgRNA1   .........................A.............      G642S
S640 sgRNA1   ..........................A............      G642D
S640 sgRNA1   ............................A..........      A643T
```

Figure 6B

```
              L  P  M  I  P  S  G  G  A  F  L
S640 ref   TGTTCTACCGATGATTCCCAGTGGCGGTGCTTTCAAAGA    (SEQ ID NO: 31)
S640 sgRNA2 .....................A.................   S640N
S640 sgRNA2 ........................A..............   G641S
S640 sgRNA2 ..........................A............   G641D
S640 sgRNA2 ............................A..........   G642S
S640 sgRNA2 ..............................A........   G642D
S640 sgRNA2 ................................A......   A643T
S640 sgRNA2 .......................................A. D645N
S640 sgRNA3 ....T..................................   L635
S640 sgRNA3 .......T...............................   P636S
S640 sgRNA3 ........T..............................   P636L
S640 sgRNA3 ................T......................   P639S
S640 sgRNA3 .................T.....................   P639L
S640 sgRNA3 ....................T..................   P639
```

| Line | ALS1 P186 seq. | ALS2 P184 seq. | ALS1 AA change | ALS2 AA change |
|---|---|---|---|---|
| WT | GTGCCAAGG | GTGCCGAGG | WT | WT |
| 1 | GTGYCAAGG | GTGCCGAGG | P184S | WT |
| 2 | GTGYYAAGG | GTGYYGAGG | P184L | P184L |
| 3 | GTGGCAAGG | GTGCCGAGG | P184A | WT |
| 4 | GTGCCAAGG | GTGYCGAGG | WT | P184S |
| 5 | GTGYCAAGG | GTGYYGAGG | P184S | P184L |

B.

| Line | ALS2 S640 sequence | ALS2 S640 AA change |
|---|---|---|
| WT | AGCGGCGGT | WT |
| 1 | ARCGGCGGT | S640N |
| 2 | ARCGGCRRT | S640N, G642N |

METHODS OF TARGETED GENETIC ALTERATION IN PLANT CELLS

The process of deliberately creating alterations in the genetic material of living cells generally has the goal of modifying one or more genetically encoded biological properties of that cell, or of the organism of which the cell forms part or into which it can regenerate. These changes can take the form of deletion of parts of the genetic material, addition of exogenous genetic material, or changes in the existing nucleotide sequence of the genetic material.

Methods of altering the genetic material of eukaryotic organisms have been known for over 20 years, and have found widespread application in plant, human and animal cells and micro-organisms for improvements in the fields of agriculture, human health, food quality and environmental protection.

The most common methods consist of adding exogenous DNA fragments to the genome of a cell, which will then confer a new property to that cell or its organism over and above the properties encoded by already existing genes (including applications in which the expression of existing genes will thereby be suppressed). Although many such examples are effective in obtaining the desired properties, these methods are nevertheless not very precise, because there is no control over the genomic positions in which the exogenous DNA fragments may be inserted (and hence over the ultimate levels of expression), and because the desired effect will have to manifest itself over the natural properties encoded by the original and well-balanced genome.

On the contrary, methods of genome editing that will result in the addition, deletion or conversion of nucleotides in predefined, i.e. targeted, genomic loci will allow the precise modification of the genome, for example in existing genes.

By using site-specific nucleases, such as zinc finger nucleases (ZFNs), transcription activator-like effector nucleases (TALENs), and Clustered Regularly Interspaced Short Palindromic Repeat (CRISPR), the field of targeted DNA alteration is rapidly developing. Despite recent advances in understanding mechanisms of targeted DNA alteration, targeted alteration in plant material is still not always successful or efficient. Indeed, available methodology is often optimized for animal, in particular human, cell material and is not always successful or efficient when applied specifically to plant cells. Thus, there is a need for new methods of providing plant cells wherein a targeted alteration has been introduced with a system and protocol specifically designed for such plant cells. Such methods of targeted alteration of DNA in a plant cell may, preferably, be successfully applied on various plant cells and with a suitable efficiency in comparison to methods known in the art.

In the light of this, new methods for targeted alteration of DNA in plant cells, and for providing plant cells and plants wherein a targeted alteration has been introduced, would be highly desirable. In particular, there is a clear need in the art for reliable, efficient, reproducible and in particular targeted methods that allow for efficient targeted alteration of a DNA molecule in a plant cell. Accordingly, the technical problem underlying the present invention can be seen in the provision of methods for complying with any of the aforementioned needs. The technical problem is solved by the embodiments characterized in the claims and herein below.

Recently, programmable deaminases have been reported (Komor et al. 2016, Nature 533: 420-424; Yang et al. 2016 Nature Communications 7:13330; Gaudelli et al. 2017 Nature 551: 464-471). The inventors for the first time report effective genome editing of plant cells using (combinations of) programmable deaminases.

BRIEF DESCRIPTION OF THE FIGURES

FIGS. 1A-1E: Nucleotide and protein sequences of the deaminase-Cas9 fusion constructs. For the rAPOBEC-Cas9-UGI-NLS construct (FIGS. 1A-1C), in both the nucleotide sequence (SEQ ID NO: 1) and the protein sequence (SEQ ID NO: 2) the rAPOBEC sequence is shown in italics, the Cas9 sequence is shown in bold, the UGI sequence is shown in underlined italics, the spacer is in regular font underlined, and the NLS sequence is shown in bold italics. The D10 and H840 amino acid codons/residues are shaded. In the construct KG10098 the D 10A change has been introduced. For the TadA-Cas9 D10A-NLS construct (FIGS. 1C-1E), in both the nucleotide sequence (SEQ ID NO: 3) and the protein sequence (SEQ ID NO: 4), the deaminase domains are shown in italics, the spacers are in regular font underlined, the Cas9 D 10A sequence is in bold and the NLS sequence is shown in bold italics.

FIG. 2: The sgRNA cassettes used (SEQ ID NO: 5-12). The sequence of the *Arabidopsis* U6 promoter is underlined, the 20 bps of the sgRNA identical to the target locus is shown in bold, the remainder of the sgRNA is in italics.

FIG. 3: Targeted base changes at the LIN5 locus of tomato. The constructs KG10098 (pK2GW7::rAPOBEC1-Cas9 D10A-UGI-NLS), KG10126 (pK2GW7::rAPOBEC1-Cas9-UGI-NLS) or KG10436 (TadA-Cas9 D10A-NLS) were used in combination with the LIN5 sgRNA expression plasmids KG10075 (SEQ ID NO: 5) or KG10252 (SEQ ID NO: 6). The 20 bps LIN5 target sites are shown as a reference (SEQ ID NO: 13-17) with the percentage of sequence reads that show a specific sequence change listed below it. Identical nucleotides are shown as dots (.) and missing nucleotides as dashes (-). The PAM sequences are indicated in bold.

FIG. 4: Mutations found at the LIN5 locus in regenerated plants. The LIN5 region containing the KG10075 and KG10252 target sequences were amplified from the plants regenerated from different mutant calli and then sequenced. The WT target sequence is shown (SEQ ID NO: 18) and under this the sequences found in each plant line (SEQ ID NO: 19-24). The nucleotide changes are underlined. Y=(C/T), R=(G/A). The LIN5 sgRNA expression plasmids used in the original transfections are also shown.

FIG. 5: Creating herbicide resistance at the tomato ALS locus using targeted deamination. The sequences of the target regions (double stranded) from the tomato ALS2 gene are shown with the codons P184 and S640 shown in bold (SEQ ID NO: 25-28).

FIGS. 6A-6B: Mutagenesis of the ALS codons P184 and S640. The sequences surrounding the codons P184 (FIG. 6A) and S640 (FIGS. 6A-6B) in the tomato ALS2 gene are shown (SEQ ID NOs: 29-31). The mutations that can be introduced by a specific sgRNA and the resulting effect on the amino acid sequence are shown. Identical nucleotides are indicated with a dot (.).

FIG. 7: Regenerated plants with C to T mutations at the ALS loci. Mutations found at the ALS1/ALS2 P186/P184 codon (A) and the ALS2 S640 codon (B). The P186/P184 and S640 codons are underlined while the mutations and the amino acid changes they produce in each line are indicated.

SUMMARY OF THE INVENTION

The invention provides for a method for targeted nucleotide editing in a cell, preferably a plant cell, comprising contacting DNA in the cell with at least one fusion protein comprising a site-specific nuclease domain and a deaminase domain. Preferably, said site-specific nuclease domain is a CRISPR-nuclease and said method further comprises contacting the DNA with one or more guide RNAs that each comprise a guide sequence for targeting the site-specific nuclease to a target sequence in the DNA. Preferably, said CRISPR-nuclease is a Cas9 or Cpf1. Preferably, the deaminase domain is selected from the group consisting of an apolipoprotein B mRNA-editing complex (APOBEC) family deaminase, an activation-induced cytosine deaminase (AID), an ACF1/ASE deaminase, an adenine deaminase, and an ADAT family deaminase.

Preferably, the deaminase domain in the at least one fusion protein is fused to the N-terminus of the nuclease domain.

Preferably, the method of the invention comprises contacting of the DNA with at least a first and a second fusion protein, wherein the first fusion protein comprises a cytosine deaminase domain and the second fusion protein comprises an adenine deaminase domain.

A fusion protein comprising a cytosine deaminase may further comprise a Uracil DNA glycosylase inhibitor domain, which preferably is fused to the C-terminus of the nuclease domain.

Optionally, the at least one fusion protein and/or the one or more guide RNAs used in the method of the invention are contacted to the DNA by introducing into the cell one or more DNA constructs for expression of said fusion protein and/or said guide RNA in the cell.

Optionally, the at least one fusion protein and/or the one or more guide RNAs used in the method of the invention are contacted to the DNA by introducing into the cell said fusion protein and/or said guide RNA.

Preferably, the fusion protein, the one or more guide RNAs and/or construct encoding the same are introduced into the cell using polyethylene glycol mediated transformation, preferably using an aqueous medium comprising PEG. In case the cell of the method of the invention is a plant cell, the method of the invention may further comprise a step of regenerating a plant or descendent thereof comprising the targeted alteration.

The invention further provides for a plant, plant part, plant product, seed, or plant cell obtained by the method of the invention wherein the cell is a plant cell, wherein the plant, plant part, seed, or plant cell is modified by comprising the targeted alteration introduced when compared to a control plant, plant part, plant product, seed, or plant cell, and wherein preferably the control plant, plant part, plant product, seed, or plant cell is plant, plant part, plant product, seed, or plant cell before the targeted alteration was introduced by the method of any of the previous claims.

The invention further provides for the use of at least one fusion protein as defined herein, or construct encoding the same, in targeted nucleotide editing of DNA in a cell, preferably a plant cell.

The invention also provides for a composition comprising a first and second fusion protein of the invention, or construct(s) encoding the same, wherein the first fusion protein comprises a cytosine deaminase domain and the second fusion protein comprises an adenine deaminase domain.

The invention also provides for a kit for targeted nucleotide editing comprising at least a first and a second fusion protein of the invention, wherein the first fusion protein comprises a cytosine deaminase domain and the second fusion protein comprises an adenine deaminase domain.

DEFINITIONS

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

"A," "an," and "the": these singular form terms include plural referents unless the content clearly dictates otherwise. Thus, for example, reference to "a cell" includes a combination of two or more cells, and the like.

As used herein, the term "about" is used to describe and account for small variations. For example, the term can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

"And/or": the term "and/or" refers to a situation wherein one or more of the stated cases may occur, alone or in combination with at least one of the stated cases, up to with all of the stated cases.

"Codon-optimized": this term refers to one or more replacement(s) of codon of a nucleic acid from a first organism (for example a bacterium) with codon more frequently used and coding for the same amino acid in a second, different, organism (for example a plant), to adapt and optimize protein translation in the second organism.

"Comprising": this term is construed as being inclusive and open ended, and not exclusive. Specifically, the term and variations thereof mean the specified features, steps or components are included. These terms are not to be interpreted to exclude the presence of other features, steps or components.

"Construct" or "nucleic acid construct" or "vector": this refers to a man-made nucleic acid molecule resulting from the use of recombinant DNA technology and which is used to deliver exogenous DNA into a host cell, often with the purpose of expression in the host cell of a DNA region comprised on the construct. The vector backbone of a construct may for example be a plasmid into which a (chimeric) gene is integrated or, if a suitable transcription regulatory sequence is already present (for example a (inducible) promoter), only a desired nucleotide sequence (e.g. a coding sequence) is integrated downstream of the transcription regulatory sequence. Vectors may comprise further genetic elements to facilitate their use in molecular cloning, such as e.g. selectable markers, multiple cloning sites and the like. "Exemplary": this terms means "serving as an example, instance, or illustration," and should not be construed as excluding other configurations disclosed herein.

"Expression": this refers to the process wherein a DNA region, which is operably linked to appropriate regulatory regions, particularly a promoter, is transcribed into an RNA, which in turn is being translated into a protein or peptide.

"Guide RNA" is to be understood herein as the RNA that targets a CRISPR-nuclease to the target sequence, and may be a CRISPR RNA (crRNA) such as used in combination with Cpf1, or the combination of a crRNA and transactivating crRNA (tracrRNA), either as two RNA strands or as a single fusion, which is known in the art as a single guide RNA (sgRNA). A sgRNA is engineered as a fusion between a crRNA and at least part of the transactivating CRISPR RNA (tracrRNA). The combination of crRNA and tracrRNA, or the sgRNA, may be used in combination with Cas, preferably Cas9.

"Guide sequence" is to be understood herein as the section of the sgRNA or crRNA, which is for targeting the sgRNA or crRNA to the target sequence in the duplex DNA.

"Plant": this includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grains and the like. Non-limiting examples of plants include crop plants and cultivated plants, such as barley, cabbage, canola, cassava, cauliflower, chicory, cotton, cucumber, eggplant, grape, hot pepper, lettuce, maize, melon, oilseed rape, potato, pumpkin, rice, rye, sorghum, squash, sugar cane, sugar beet, sunflower, sweet pepper, tomato, water melon, wheat, and zucchini.

"Nucleic acid sequence" or "nucleotide sequence": This refers to the order of nucleotides of, or within a nucleic acid. In other words, any order of nucleotides in a nucleic acid may be referred to as a sequence of nucleic acid sequence. Likewise, a "target sequence" is to denote an order of nucleotides within a nucleic acid that is to be targeted, i.e. wherein an alteration is to be introduced. Within the context of the current invention a first target nucleic acid sequence may be comprised within or overlap with a further target nucleic acid sequence. The target sequence may be an order of nucleotides comprised in a first strand of a DNA duplex.

The term "deaminase" refers to an enzyme that catalyzes a deamination reaction. In some embodiments, the deaminase is a cytosine deaminase, catalyzing the hydrolytic deamination of cytosine to uracil. The deaminase may also be an adenine deaminase, catalyzing the deamination of adenine thereby converting it to inosine.

The term "effective amount," as used herein, refers to an amount of a biologically active agent that is sufficient to elicit a desired biological response. For example, in some embodiments, an effective amount of a nuclease may refer to the amount of the nuclease that is sufficient to induce cleavage of a target site specifically bound and cleaved by the nuclease. In some embodiments, an effective amount of a fusion protein provided herein, e.g., of a fusion protein comprising a nuclease domain and a deaminase domain may refer to the amount of the fusion protein that is sufficient to induce editing of a target site specifically bound and edited by the fusion protein. As will be appreciated by the skilled artisan, the effective amount of an agent, e.g., a fusion protein, a nuclease, a deaminase, a recombinase, a hybrid protein, a protein dimer, a complex of a protein (or protein dimer) and a polynucleotide, or a polynucleotide, may vary depending on various factors as, for example, on the desired biological response, e.g., on the specific allele, genome, or target site to be edited, on the cell or tissue being targeted, and on the agent being used.

A nucleotide or polypeptide "variant" of a specific nucleic acid or polypeptide is to be understood herein as a nucleotide or polypeptide "derived" from a specific nucleotide or polypeptide. For example, a variant of a nucleic acid having SEQ ID NO: 1 or 3, or a nucleic acid derived from a nucleic acid having SEQ ID NO: 1 or 3 preferably comprises or consists of a nucleotide sequence having at least 50%, 60%, 70%, 80%, 90, 91, 92, 93, 94, 95 96 97, 98 or at least 99% identity to SEQ ID NO: 1 or 3, respectively. In a further example, a variant of a polypeptide or protein having SEQ ID NO: 2 or 4, or a polypeptide or protein derived from a polypeptide or protein having SEQ ID NO: 2 or 4 preferably comprises or consists of an amino acid sequence comprising or consisting of at least 50%, 60%, 70%, 80%, 90, 91, 92, 93, 94, 95 96 97, 98 or at least 99% identity to SEQ ID NO: 2 or 4, respectively.

DETAILED DESCRIPTION

It is contemplated that any method, use or composition described herein can be implemented with respect to any other method, use or composition described herein. Embodiments discussed in the context of methods, use and/or compositions of the invention may be employed with respect to any other method, use or composition described herein. Thus, an embodiment pertaining to one method, use or composition may be applied to other methods, uses and compositions of the invention as well.

As embodied and broadly described herein, the present invention is directed to a method for targeted editing of DNA in a cell, preferably a plant cell, using a site-specific nuclease domain fused to a deaminase domain. More in particular the invention provides for a method for targeted nucleotide editing in a cell, preferably a plant cell, comprising the contacting of DNA in the cell, preferably genomic DNA, with at least one fusion protein comprising a site-specific nuclease domain and a deaminase domain. Optionally, at least two different fusion proteins are used in the method of the invention, wherein preferably a first fusion protein comprises a cytosine deaminase domain and a second fusion protein comprises an adenine deaminase domain. The inventors for the first time report effective targeted nucleotide editing of plant cells using this method. The method according to the invention is in particular suitable for accurate introduction of pre-defined and desired modifications in a locus of interest present in the duplex DNA present in a plant cell, but is not limited thereto. The method of the invention may also be used for accurate introduction of pre-defined and desired modifications in a locus of interest present in the duplex DNA present in e.g. a microorganism, a mammalian cell, a eukaryotic cell, a human cell and/or an animal cell. Preferably, in case the cell is a human or animal cell, the method of the invention is an ex vivo (e.g. in vitro) method. Optionally, the method as defined herein is not a method for treatment of the human or animal body. Optionally, the method as defined herein is not performed on the human or animal body. In addition to the unexpected finding broadly described above, the current inventors also found that within the method of the invention, even more optimal results may be achieved by including several other factors, as will be detailed below.

From the following detailed description, the skilled person will understand that method for targeted alteration of DNA in a cell, preferably a plant cell, may also find use as a method for the provision of a cell having a targeted alteration or modification in a duplex DNA molecule in that cell. Further, the method of the invention may provide for a plant, and a descendent thereof, or a plant part, comprising a targeted alteration or modification in a duplex DNA molecule in that plant or plant part, wherein the alteration or modification is relative to duplex DNA molecule of a plant or plant part not treated with the method according to the invention.

With the method of the invention an alteration (i.e. a change or modification) in the nucleotides may be introduced in the duplex DNA of the cell, changing the sequence of said DNA. In other words, the targeted alteration is a specific and selective alteration of one or more nucleotides at (a) specific site(s) in the duplex DNA.

The duplex DNA in the cell comprises a first DNA strand a second DNA strand. The second DNA strand is the complement of the first DNA strand and pairs to it to form the duplex. For example, a complement of a first DNA strand sequence ATTT (in the 5' to 3' direction) is TAAA (in the 3' to 5' direction). The DNA of the duplex DNA may be any type of DNA, endogenous or exogenous to the, for example genomic DNA, chromosomal DNA, artificial chromosomes, plasmid DNA, or episomal DNA. The duplex may be nuclear or organellar DNA. Preferably, the DNA duplex is chromosomal DNA, preferably endogenous to the cell. It is further understood that the terms "DNA", "duplex DNA" and "DNA molecule" may be used interchangeable herein, except if it is clear from its context that a single stranded DNA molecule is intended.

Within the context of the current invention, the first DNA strand of the DNA duplex comprises a target sequence and the second (complementary) strand comprises a nucleotide sequence that is antisense to the target sequence and capable of hybridizing to the target sequence.

The skilled person understands that the "target sequence" is to denote an order of nucleotides (i.e. nucleotide sequence) that is to be targeted, i.e. wherein an alteration is to be introduced. In other words, the first strand comprises a nucleic acid sequence that is to be targeted with the method of the invention, i.e. wherein an alteration is to be introduced.

The target sequence is not limited to a particular part or section of the DNA. The target sequence may for example, be part of an intron or an exon, may be part of a coding or non-coding sequence, and/or may be part of a regulatory element or not. The target sequence thus refers to an order of nucleotides that is comprised in the first strand. Preferably, the target sequence is present only once or twice in the DNA. However, the target sequence may be present more often, for example but not limited to, 3, 4, 5, 6, 7, 8, 9 or 10 times within the DNA of the cell.

In case the site-specific nuclease of the fusion protein of the invention is a CRISPR-nuclease, the target sequence of the first strand, or its antisense sequence in the second strand is flanked or followed by a protospacer adjacent motif (PAM) sequence that is required by the particular CRISPR-nuclease. The precise sequence and length requirements for the PAM differs depending on the CRISPR-nuclease used, but PAMs are typically 2-5 base pair sequences adjacent the sequence recognized by the guide sequence of the guide RNA. The skilled person will be able to identify further PAM sequences for use with a given CRISPR-nuclease. For instance, in case the CRISPR nuclease is Cas9, the sequence targeted by the guide sequence is flanked at its 3' end by a suitable PAM for example 5'-NRG (e.g. 5'-NGG) or 5'-NN-GRR for SpCas9 or SaCas9 enzymes (or derived enzymes), respectively. In case the nuclease is Cpf1, the sequence targeted by the guide sequence is flanked at its 5' end by a suitable PAM for example 5'-TTTN.

More in particular the invention provides for a method for targeted nucleotide editing in a plant cell, comprising the contacting of a DNA molecule with at least one fusion protein comprising a site-specific nuclease and a deaminase domain.

In the method of the invention, a cell, preferably a plant cell, comprising the DNA to be targeted is provided, wherein said DNA is exposed to at least one fusion protein comprising at least a site-specific nuclease domain and a deaminase domain. In case the nuclease domain is a CRISPR-nuclease as further detailed herein, the DNA is further exposed to a guide RNA for targeting the fusion protein to a target sequence in the DNA strand. Optionally, together with the fusion protein and the optional guide RNA, the DNA molecule may be further exposed to functional proteins as further detailed herein. The DNA molecule is exposed to the fusion protein, and optionally the guide RNA and/or further functional proteins, in an amount effective and under conditions suitable for the deamination of a nucleotide base. Deamination of a cytosine results in the direct conversion to uracil, thereby effecting a C to T substitution, or G to A substitution if the complementary strand is targeted. Deamination of adenine results in the direct conversion to inosine, thereby effecting an A to G substitution, or T to C substitution if the complementary strand is targeted. Aspects of this method are further detailed herein below.

Plant Cell

As indicated herein, the method of the invention may be applied to any type of cell in which DNA is desired to be edited. Preferably, the cell is a plant cell. According to the invention, any type of plant cell may be used in the method as long as the plant cells allows the exposure of the DNA duplex to a fusion protein as defined herein (e.g. comprising a site-specific nuclease), and in some embodiments, the guide RNA. However, in a preferred embodiment the plant cell is a plant protoplast. The skilled person is aware of methods and protocols for preparing and propagation plant protoplasts, see for example Plant Tissue Culture (ISBN: 978-0-12-415920-4, Roberta H. Smith). The plant protoplasts for use in the method of the current invention can be provided using common procedures (e.g. using macerase and/or cellulases and pectinases) used for the generation of plant cell protoplasts.

Plant cell protoplasts systems have for example been described for tomato, tobacco and many more (*Brassica napus, Daucus carota, Lactuca sativa, Zea mays, Nicotiana benthamiana, Petunia hybrida, Solanum tuberosum, Oryza sativa*). The present invention is generally applicable to any protoplast system, including those, but not limited to, the systems described in any one of the following references: Barsby et al. 1986, Plant Cell Reports 5(2): 101-103; Fischer et al. 1992, Plant Cell Rep. 11(12): 632-636; Hu et al. 1999, Plant Cell, Tissue and Organ Culture 59: 189-196; Niedz et al. 1985, Plant Science 39: 199-204; Prioli and Söndahl, 1989, Nature Biotechnology 7: 589-594; S. Roest and Gilissen 1989, Acta Bot. Neerl. 38(1): 1-23; Shepard and Totten, 1975, Plant Physiol.55: 689-694; Shepard and Totten, 1977, Plant Physiol. 60: 313-316,which are incorporated herein by reference.

As explained herein, the skilled person understands that the method of the current invention may be applicable to different types of plant cells, for example plant cells of different plant species. Indeed it is contemplated the invention disclosed herein may be applicable to plant cells of a wide range of plants, both monocots and dicots. Non-limiting examples include plant cells from the Cucurbitaceae, Solanaceae and Gramineae, maize/corn (*Zea* species), wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), *Brassica* spp. (e.g. *B. napus, B. juncea, B. oleracea, B. rapa*, etc), sunflower (*Helianthus annus*), safflower, yam, cassava, alfalfa (*Medicago sativa*), rice (*Oryza* species, e.g. *O. sativa* indica cultivar-group or japonica cultivar-group), forage grasses, pearl millet (*Pennisetum* spp. e.g. *P. glaucum*), tree species (*Pinus*, poplar, fir, plantain, etc), tea, coffea, oil palm, coconut, vegetable species, such as pea, zucchini, beans (e.g. *Phaseolus* species), cucumber, artichoke, asparagus, broccoli, garlic, leek, lettuce, onion, radish, lettuce, turnip, Brussels sprouts, carrot, cauliflower, chicory, celery, spinach, endive, fennel, beet, fleshy fruit bearing plants (grapes, peaches, plums, strawberry, mango, apple, plum, cherry, apricot, banana, blackberry, blueberry, citrus, kiwi, figs, lemon, lime, nectarines, raspberry, watermelon, orange, grapefruit, etc.), ornamental species (e.g. *Rose, Petunia, Chrysanthemum, Lily, Gerbera* species), herbs (mint, parsley, basil, thyme, etc.), woody trees (e.g. species of *Populus, Salix, Quercus, Eucalyptus*), fibre species e.g. flax (*Linum usitatissimum*) and hemp (*Cannabis sativa*), or model organisms, such as *Arabidopsis thaliana*.

However, in a preferred embodiment the plant cells are plant cells obtained from a *Solanum* species such as potato or tomato (e.g. *Solanum lycopersicum*).

The skilled person may provide plant protoplasts by using methods available in the art for the preparation of plant protoplasts for various plants. For example, plant protoplasts may be prepared by treating a whole plant, a part of a plant or plant cells with enzymes such as cellulose or pectinase or by an appropriate mechanical means to remove the cell wall. The resultant plant protoplasts are then placed in an aqueous solution containing an osmotic pressure control agent in order to maintain them in a stable form (see for example Reusink et al. Science (1966) 154 (3746): 280-281 DOI: 10.1126/science.154.3746.280 or Muhlbach et al. Planta (1980)148 (1): 89-96.).

The skilled person will understand how to provide a plant cell within the context of the current invention, for example by providing the living plant cell in a suitable medium and at a suitable temperature. It will be understood by the skilled person that the number of cells is not limited in any way, however in general a population of plant cells will be provided. A non-limiting number of cells may, for example, be 10,000-2,000,000 plant cells per milliliter of aqueous medium used in the method. Although preferably the plant cells are from the same species, in some embodiments more than one species of plant cell may be used in the same experiment.

Fusion Protein

The one or more fusion proteins used in the method of the invention comprise at least one site-specific nuclease domain and at least one deaminase domain.

Site-Specific Nuclease Domain

The site-specific nuclease domain is, or is derived from, or is a variant of, a site-specific nuclease that binds to and recognizes a particular recognition sequence within a DNA molecule. Upon binding to a duplex DNA, a catalytically active site-specific nuclease may cleave one or both of the DNA strands in a strictly determined manner. The nuclease domain of the fusion protein defined herein may be active, or partly or wholly catalytically inactive, as detailed herein below.

The nuclease domain may be any type of site-specific nuclease or a variant or fragment thereof. Preferably, the nuclease domain is, or is a variant of a CRISPR-nuclease, such Cas9 or Cpf1. Optionally, the nuclease is a zinc-finger nuclease (ZFN), meganuclease or TALE nuclease. A TALE nuclease is a nuclease having a TALE binding domain fused to a bacterial nuclease FokI. The CRISPR-nuclease may be a mutant CRISPR-nuclease such that one or more domains of the nuclease is inactivated. Cas9 and Cpf1 comprise two nuclease domains each cleaving a single strand of a DNA duplex. In case one of these domains are inactivated a nickase results, which cleaves one strand of the double stranded DNA. In case both domains are inactivated, dead nuclease results, having no nucleic acid cleavage activity at all.

In case the nuclease is a CRISPR-nuclease, said nuclease is an RNA-guided nuclease. RNA-guided nucleases comprise a nuclease domain and at least one domain that interacts with a guide RNA. An RNA-guided nuclease is directed to a specific nucleic acid sequence by a guide RNA. The guide RNA interacts with the RNA-guided nuclease as well as with the specific recognition sequence in the DNA, such that, once directed to the site comprising the specific nucleotide acid sequence, the RNA-guided nuclease is able to introduce a single or double strand break at the target site, in case one or both domains of the nuclease are catalytically active, respectively.

In accordance therewith, the method of the invention may further comprise contacting the DNA to a guide RNA that comprises a guide sequence for targeting the site-specific nuclease to the target site in the DNA molecule. Preferably the guide RNA contacting the DNA interacts simultaneously with the nuclease domain(s). The skilled person knows how to prepare the different components of the CRISPR-CAS system, including CRISPR-nuclease. In the prior art, numerous reports are available on its design and use. See for example the recent review by Haeussler et al (J Genet Genomics. (2016)43(5):239-50. doi: 10.1016/j.jgg.2016.04.008.) on the design of guide RNA and its combined use with a CAS-protein (originally obtained from *S. pyogenes*), or the recent review by Lee et al. (Plant Biotechnology Journal (2016) 14(2) 448-462), which are all incorporated herein by reference. Therefore, the skilled person is well aware on how to design a guide RNA in a manner that it, when combined with a catalytically active CRISPR-nuclease effects the introduction of a strand break on a predefined site in the DNA molecule.

The nuclease domain may be, or be a variant of, a Cas9 protein derived from the bacteria *Streptococcus pyogenes* (SpCas9; NCBI Reference Sequence NC_017053.1; UniProtKB-Q99ZW2). Variants may be SpCas9 VQR mutant, SpCas9 VRER mutant and/or SpCas9 EQR mutant as described in Kleinstiver et al., 2015 (Kleinstiver et al, Nature 2015, 523, 481-485). Other Cas9 proteins may also be useful, such as *Streptococcus aureus* Cas9 or SaCas9 (CCK741173.1) and variants thereof such as SaCas9 KKH mutant (Kleinstiver et al, Nature Biotechnology 2015, 33, 1293-1298), GeoCas9 (Harrington et al, Nature Communications, 2017 Nov. 10; 8(1):1424) and ThermoCas9 (Mougiakos et al., 2017, Nature Communications 2017 Nov. 21; 8(1):1647), or variants thereof. Further useful examples of CRISPR related proteins include but are not limited to CAS9, CSY4, dCAS9, and dCAS9-effector domain (activator and/or inhibitor domain) fusion proteins, and another example, such as Cpf1 and such as for example described in 2015 by Zetsche et al. (Cell 163, 759-771) and in WO2015/006747. Cpf1 may for example be AsCpf1 (from *Acidaminococcus*) and LbCpf1 (from Lachnospiraceae), or variants thereof. Cpf1 is a single RNA-Guided Endonuclease of a Class 2 CRISPR-Cas System (see e.g. Cell (2015) 163(3): 759-771. Cpf1 is a single RNA-guided endonuclease lacking tracrRNA, and it utilizes a T-rich protospacer-adjacent motif. Cpf1 cleaves DNA via a staggered DNA double-stranded break. Cpf1 has shown to have efficient genome-editing activity in human cells. Cpf1 may thus be used as an alternative CAS-protein as part of the CRISPR system.

In general, a Cas protein, such as a Cas9 protein comprises two nuclease domains. For example, a Cas9 protein can comprise a RuvC-like nuclease domain and an HNH-like nuclease domain. The RuvC and HNH domains work together to cut single strands to make a double-stranded break in DNA. (Jinek et al., Science, 337: 816-821). Such Cas protein, that would normally introduce a DSB, may be modified to contain only one functional nuclease domain (for example, either a RuvC-like or an HNH-like nuclease domain), or to contain none functional nuclease domain. The nuclease domain may be or be a variant of a Cas protein wherein one or more nuclease domains is mutated such that it is no longer functional (i.e., the nuclease activity is absent), therewith creating a CRISPR nickase. Examples are SpCas9 variants having mutations such as D10A (for example as described by Cong et al (Science (2013); 339 (6121):819-23)) or H840A. Such CRISPR nickase is thus able to introduce a nick into a double-stranded nucleic acid, but not cleave the double-stranded DNA. In case both domains are mutated such that they are no longer functional, dCas results. An example is a SpCas9 variant having both the mutation D10A and H840A. Such dCas is able to bind the double-stranded nucleic acid but does not cleave either of the strands. CRISPR nickases and dCas are known to the skilled person, and examples thereof are provided herein elsewhere. One or both of the nuclease domains of a CRISPR-nuclease can be modified, for example inactivated, using well-known methods, such as site-directed mutagenesis, PCR-mediated mutagenesis, and total gene synthesis, as well as other methods known in the art.

The nuclease domain of the fusion protein may comprise or consist of the whole Cas9 protein or variant or may comprise a fragment thereof. Preferably such fragment does bind crRNA and tracrRNA or sgRNA, but may lack one or more residues required for nuclease activity. In addition to the above indicated preferred Cas9 protein, Cas9 may be Cas9 from *Corynebacterium ulcerous* (NCBI Refs: NC_015683.1, NC_017317.1); *Corynebacterium diphtheria* (NCBI Refs: NC_016782.1, NC_016786.1); *Spiroplasma syrphidicola* (NCBI Ref. NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychrojlexus torquisl* (NCBI Ref: NC_018721.1); *Streptococcus thermophilus* (NCBI Ref: YP_820832.1); *Listeria innocua* (NCBI Ref: NP 472073.1); *Campylobacter jejuni* (NCBI Ref: YP_002344900.1); ox *Neisseria, meningitidis* (NCBI Ref: YP_002342100.1). Encompassed are Cas9 variants from these, having an inactivated HNH and/or RuvC domain homologues to SpCas9 D10A, SpCas9 H840A and SpCas9 D10A/H840A.

The recently discovered CRISPR-Cas nuclease Cpf1 was first believed to contain only a RuvC nuclease domain, but very recently, structural and functional studies show that Cpf1 acts as a monomer and contains a second putative novel nuclease (NUC) domain (see Gao et al. Cell Research (2016) 26:901-913, Yamano et al. Cell (2016) 165(4): 949-962).

According to a preferred embodiment, the nuclease domain may be a Cpf1 protein or fragment or variant thereof. Cpf1 may be Cpf1 from *Acidaminococcus* sp; UniProtKB-U2UMQ6. The variant may be Cpf1 having an inactivated RuvC and/or NUC domain, wherein the RuvC and/or NUC domain has no nuclease activity anymore. The skilled person is well aware of techniques available in the art such as site-directed mutagenesis, PCR-mediated mutagenesis, and total gene synthesis that allow for inactivated nucleases such as inactivated RuvC, NUC and/or HNH domains. The nuclease domain of the method of the invention may also be a variant of Cpf1 having an inactivated NUC domain. An example of such variant is Cpf1 R1226A (see Gao et al. Cell Research (2016) 26:901-913, Yamano et al. Cell (2016) 165(4): 949-962). In this variant, there is an arginine to alanine (R1226A) conversion in the NUC-domain, which inactivates the NUC-domain.

In another embodiment, the site-specific nuclease may be a functional fragment of a TALE nuclease. Transcription activator-like effector nucleases (TALENs) have rapidly emerged as an alternative to ZFNs for genome editing and introducing targeted double-strand breaks (DSBs), i.e. in which both strands of the DNA duplex are severed. TALENs are similar to ZFNs and comprise a non-specific FokI nuclease domain fused to a customizable DNA-binding domain. This DNA-binding domain is composed of highly conserved repeats derived from transcription activator-like effectors (TALEs), which are proteins secreted by Xanthomonas bacteria to alter transcription of genes in host plant cells.

In more detail, TALEs consist of a number of repeating protein domains, each of which is able to specifically recognize and bind to one of the four DNA nucleotides (A, T, G, C). The domains specific for each nucleotide have been identified and arrays of these domains, which have high binding affinity for any DNA sequence can be produced (Christian, 2010, Genetics 186: 757-761; Cormac et al., 2011, Nucleic Acids Res 39:e82; Bogdanove and Voytas, 2011, Science 333: 1843-1846; Boch, 2011, Nature Biotechnology 29:135-136). These arrays are then fused to the nuclease domain of FokI to create a TALEN and, similar to ZFN, two TALEN proteins are used to induce a DNA DSB in the target DNA duplex. Several papers have described the use of TALENs to create mutations at the target sequence (Curtin (2012) The Plant Genome, 5, 42-50). Joung et al. (Nat Rev Mol Cell Biol. (2013) 14(1): 49-55. doi: 10.1038/nrm3486A) reviewed and compared various techniques employing TALENs in targeted genome editing. Like CRISPR systems, Transcription activator-like effector (TALE) nucleases (TALENs) are an efficient genome-editing tool.

Optionally, the site-specific nuclease domain is a TALE nuclease or functional fragment thereof that does not introduce double strand breaks, but only introduces a nick in one of the strands. Optionally, said site-specific nuclease domain is a TALE nuclease or functional fragment thereof that has no nuclease activity, i.e. both domains or monomers of the TALE nuclease are inactive. The skilled person is well aware of techniques available in the art such as site-directed mutagenesis, PCR-mediated mutagenesis, and total gene synthesis that allow for the provision of a TALE nickase or a nuclease inactive TALE. Examples of TALE nickases are described in the art (see for example Wu et al. Biochem Biophys Res Commun. (2014) 2014 Mar. 28; 446(1):261-266 and Luo et al. Scientific Reports 6 (2016), Article number: 20657 and WO 2015/164748). Inactivation of a TALE monomer involves a D450 mutation of the FokI catalytic domain creating an inactive monomer with strand-specific nicking activity (see Luo et al. supra).

Deaminase Domain

Optionally, the deaminase domain of the method of the invention is a deaminase, or functional fragment thereof, selected from the group consisting of an apolipoprotein B mRNA-editing complex (APOBEC) family deaminase, an activation-induced cytosine deaminase (AID), an ACF1/ASE deaminase, an adenine deaminase, and an ADAT family deaminase. Alternatively, the deaminase or functional fragment thereof may be ADAR1 or ADAR2, or a variant thereof.

The apolipoprotein B mRNA-editing complex (APOBEC) family of cytosine deaminase enzymes encompasses eleven proteins that serve to initiate mutagenesis in a controlled and beneficial manner. The cytosine deaminase of the APOBEC family is activation-induced cytosine (or cytidine) deaminase (AID) or apolipoprotein B editing complex 3 (APOBEC3). These proteins all require a $Zn^{2+}$-coordinating motif (His-X-Glu-X23-26-Pro-Cys-X2_4-Cys) and bound water molecule for catalytic activity. Preferably, in a method of the invention, the deaminase domain of the fusion protein is an APOBEC1 family deaminase. Preferably, the deaminase domain is rat deaminase (rAPOBEC1) having the sequence as indicated in FIGS. 1A-1C in italics (SEQ ID NO: 1 provides the encoding sequence and SEQ ID NO: 2 provides the amino acid sequence), or variant thereof.

Another exemplary suitable type of deaminase for use in the fusion protein of the method of the present invention is an adenine (or adenosine) deaminase. For example, an ADAT family adenine deaminase can be fused to a site-specific nuclease domain, such as a Cas9 domain, e.g., a nuclease-inactive Cas9 domain, thus yielding a Cas9-ADAT fusion protein. Further, the adenine deaminase may be TadA or a variant thereof, preferably as described in Gaudelli et al., 2017 (Gaudelli et al. 2017 Nature 551: 464-471). Preferably, the deaminase domain is TadA having the sequence as indicated in FIGS. 1C-1E in italics (SEQ ID NO: 3 provides the encoding sequence and SEQ ID NO: 4 provides the amino acid sequence), or variant thereof. Further, the fusion protein may comprise a site-specific nuclease domain, such as a Cas9 domain, fused to an adenine deaminase domain, e.g. derived from ADAR1 or ADAR2.

The deaminase domain of the present invention may comprise or consist of a whole deaminase protein or a fragment thereof which has catalytic activity.

Linker

The deaminase domain may be fused to the N- or C-terminus of the nuclease domain. Preferably, the deaminase domain is fused to the N-terminus of the nuclease domain. Optionally, the deaminase and nuclease domain of fusion protein of the method of the invention are fused directly to each other or via a linker (also denominated herein as a spacer). The linker may be any suitable linker in the art, e.g., ranging from very flexible linkers of the form (GGGGS)n, (GGS)n, and (G)n to more rigid linkers of the form (EAAAK)n (SEQ ID NO: 38), SPKKKRKVEAS (SEQ ID NO: 32), or SGSETPGTSESATPES SEQ ID NO: 33), or KSGSETPGTSESATPES (SEQ ID NO: 34), or any variant thereof, wherein n preferably is between 1 and 7, i.e. 1, 2, 3, 4, 5, 6, or 7. The linker preferably has a length between 2 and 30 amino acids, or between 3 and 23 amino acids, or between 3 and 12 amino acids. The linker may have the sequence as indicated in FIGS. 1A-1E in regular font underlined in SEQ ID NO: 1 and 3 (encoding sequence) and SEQ ID NO: 2 and 4 (amino acid sequence), or a variant thereof.

Uracil DNA Glycosylase Inhibitor Domain

Optionally, the fusion protein further comprises an UDG inhibitor (UGI) domain. The UGI domain may be fused to the N- or C-terminus of the nuclease domain. Preferably, the deaminase domain is fused to the C-terminus of the nuclease domain. The fusion may be direct or via a linker as indicated above. Preferably, the fusion protein comprises the deaminase domain fused to the N-terminus of the nuclease domain, and the UGI domain is fused to the C-terminus of the nuclease domain.

Uracil DNA glycosylases (UDGs) recognize uracil, inadvertently present in DNA and initiate uracil excision repair pathway by cleaving the N-glycosidic bond between the uracil and the deoxyribose sugar, releasing uracil and leaving behind a basic site (AP-site). The AP-site is then processed and restored to a canonical base by the subsequent actions of AP-endonuclease, dRPase, DNA polymerase and DNA ligase enzymes. By fusing a UGI domain to the cytosine deaminase-nuclease fusion protein, the efficiency of base editing increases. Preferably, the UGI domain is or is a variant of UGI from *B. subtilis* bacteriophage PBS1 or PBS2 (UniProtKB-P14739). The UGI domain may have the sequence as indicated in FIGS. 1A-1C in underlined italics in SEQ ID NO: 1 (encoding sequence) and 2 (amino acid sequence), or variant thereof.

In an embodiment, the UDG inhibitor is not fused to the fusion protein as defined herein, but is contacted to the DNA to be edited as a further functional protein, preferably together with the fusion protein and optionally with the guide RNA. In this embodiment, the cell, preferably the plant cell, may be transfected using the UDG inhibitor or a construct encoding the UDG inhibitor. In the latter case, said construct may further comprise a sequence encoding the fusion protein of the invention, or alternatively, the UDG inhibitor and fusion protein of the invention may be encoded on separate constructs.

Tags

The fusion protein may further provide a tag for ease of purification and/or detection. Such tags are well known in the art. Such tag is preferably located N- or C-terminal of the fusion protein, preferably N-terminal. Preferably, the tag is a His-tag (HHHHHH) (SEQ ID NO: 37).

The fusion protein of the invention may further comprise one or more nuclear localization signal sequences (NLS), preferably at the N- or C-terminus of the fusion protein, or both the N-and C-terminus. The NLS may be any suitable NLS known in the art, preferably having the sequence as indicated in bold italics in FIGS. 1A-1E in SEQ ID NO: 1 and 3 (encoding sequence) and SEQ ID NO: 2 and 4 (amino acid sequence), or variant thereof.

The fusion protein used in the method of the invention may be a protein encoded by a nucleotide sequence comprising or consisting of a sequence as shown in FIGS. 1A-1D (SEQ ID NO: 1 and 3), or a variant thereof having at least 70%, such as at least 75%, 80%, 85%, 90%, 95%, 96%, 97%, 98%, or 99% sequence identity to the open reading frame (ORF) having a nucleotide sequence as shown in FIGS. 1A-1D (SEQ ID NO:1 or SEQ ID NO: 3). Preferably the fusion protein is a protein comprises or consists of an amino acid sequence as shown in FIGS. 1B-1C and 1E (SEQ ID NO: 2 and 4), or a variant thereof having at least 70%, such as at least 75%, 80%, 85%, 90%, 95%, 96%, 97%, 98%, or 99% sequence identity to the amino acid sequence as shown in FIGS. 1B-1C and 1E (SEQ ID NO:2 or SEQ ID NO: 4).

Guide RNA

In case the nuclease domain is or is a variant of a CRISPR-nuclease, the method of the invention further comprises contacting a DNA molecule with a guide RNA that comprises a guide sequence for targeting the fusion protein(s) and/or the site-specific nuclease domain to the target sequence or the antisense sequence in the complementary strand in the DNA molecule. Although the guide RNA is not in particular limited to a certain size (length, nucleotides), according to a preferred embodiment, the guide sequence is 5-100, preferably 10-50, even more preferably 15-25, or 20 nucleotides in length. Optionally, more than one type of guide RNA may be used in the same experiment, for example aimed at two or more different target sequences, or even aimed at the same target sequence.

Preferably, the guide sequence is identical to the target sequence on the template to be edited or the antisense sequence thereof in the complementary strand. In other words, preferably the guide RNA is designed such that the guide sequence is identical to the sequence of the template to be edited or antisense thereof. Preferably, the guide sequence comprises or consists of the same sequence as the target sequence comprising the nucleotide(s) to be edited or the sequence antisense thereof, i.e. the stretch of 5-100, preferably 10-50, even more preferably 15-25 or 20 nucleotides of the target sequence comprising the nucleotide to be deaminated, or the sequence antisense thereof.

The desired editing of the target sequence determines the design of the combination of fusion protein(s) and guide RNA(s). For instance, if one or more C to T (or G to A) conversions are desired in the target sequence, preferably a fusion protein is selected as defined herein comprising a cytosine deaminase fused to a site-specific (e.g. CRISPR)-nuclease. Similarly, if one or more A to G (or T to C) conversions are desired in the target sequence, preferably a fusion protein is selected as defined herein comprising an adenine deaminase fused to a site-specific (e.g. CRISPR)-nuclease.

In case the fusion protein comprises a CRISPR-nuclease domain, preferably, the nuclease domain is a CRISPR-nickase that is capable of nicking the strand complementary to the strand comprising the PAM sequence. Such CRISPR-nickase may be a Cas9 which contains a nuclease disabling mutation in the RuvC domain such as Cas9-D10A, or variant thereof. The desired editing of the target sequence determines the design of the combination of fusion protein(s) and guide RNA(s), as exemplified below for the situation where a fusion domain is used comprising a nuclease domain that is a CRISPR-Cas9 which contains a nuclease disabling mutation in the RuvC domain.

For instance, if one or more C to T conversions are desired in the target sequence, preferably the fusion protein used in the method of the invention comprises a cytosine deaminase fused to a CRISPR-nuclease that requires a PAM sequence that is flanked by the target sequence in such a way that a suitable guide RNA comprising a guide sequence that comprises or consists of the target sequence, targets the fusion protein-guide RNA to the target site, which results in nicking of the strand complementary to the strand comprising the target sequence. Without being wished to be bound by any theory, nicking of the strand complementary to the target sequence is thought to allow the deaminase to convert one or more cytosines of the strand that remains intact.

In case one or more A to G conversions are desired in the target sequence, preferably the fusion protein used in the method of the invention comprises an adenine deaminase fused to a CRISPR-nuclease that requires a PAM sequence that is flanked by the target sequence in such a way that a suitable guide RNA comprising a guide sequence that comprises or consists of the target sequence, targets the fusion protein-guide RNA to the target site, which results in nicking of the strand complementary to the strand comprising the target sequence. Without being wished to be bound by any theory, nicking of the strand complementary to the target sequence is thought to allow the deaminase to convert one or more adenines of the strand that remains intact.

In case one or more G to A conversions are desired in the target sequence, preferably the fusion protein used in the method of the invention comprises a cytosine deaminase fused to a CRISPR-nuclease, preferably a Cas9-D10A variant, that requires a PAM sequence that is flanked by the antisense sequence of the target sequence (i.e. in the strand complementary to the strand comprising the target sequence) in such a way that a suitable guide RNA comprising a guide sequence that is complementary to the target sequence, targets the fusion protein-guide RNA to the target site, which results in nicking of the strand comprising the target sequence. The conversion of one or more cytosines to uracil in the strand that remains intact (i.e. the strand comprising the antisense sequence) effectively results in a conversion of one or more guanines to an adenines in the target sequence.

In case one or more T to C conversions are desired in the target sequence, preferably the fusion protein used in the method of the invention comprises an adenine deaminase fused to a CRISPR-nuclease, preferably a Cas9-D10A variant, that requires a PAM sequence that is flanked by the antisense sequence of the target sequence (i.e. in the strand complementary to the strand comprising the target sequence) in such a way that a suitable guide RNA comprising a guide sequence that is complementary to the target sequence, targets the fusion protein-guide RNA to the target site, which results in nicking of the strand comprising the target sequence. The conversion of one or more adenines to inosines in the strand that remains intact (i.e. the strand comprising the antisense sequence) effectively results in a conversion of one or more a thymines to cytosines in the target sequence.

As detailed herein, the inventors unexpectedly discovered that the use of combinations of different fusion proteins can be used to effectively edit target sequences in a single transfection event and in a single cell. It is even possible to edit a single target sequence in a single transfection event and in a single cell using different fusion proteins and/or different guide RNAs, thereby making several different nucleotide conversions (e.g. combinations of one or more C to T, one or more A to G, one or more G to A and/or one or more T to C conversions) in a single target sequence. Therefore, the method of the invention is in particular suitable for the conversion of different kind of nucleotides, i.e. introducing mutations at different nucleotides (i.e. one or more C to T conversions, one or more G to A conversions, one or more A to G conversion, one or more T to C conversions, and any combination thereof) in a single target sequence in a single cell and in a single transfection event.

Contacting

In the method of the invention, the DNA of the cell, preferably the plant cell, is contacted at least with the fusion protein of the invention. Optionally, the cell is contacted with at least two proteins of the invention, preferably each comprising different deaminase domains. For instance, one of the fusion proteins (a first fusion protein) may comprise a cytosine deaminase domain and the other fusion protein (a second fusion protein) may comprise an adenine deaminase domain. As set out above, this allows for one or more C to T (or G to A) conversions and one or more and A to G (or T to C) conversions in a single transfection event in a single cell. The inventors even found that one or more C to T (or G to A) conversions and one or more and A to G (or T to C) conversions could be made using this method at a single target site within a cell, i.e. using a single guide RNA that targets both the first and the second fusion protein to the same target sequence. Thus, provided is a method comprising contacting the DNA with a fusion protein comprising a cytosine deaminase domain and a fusion protein comprising an adenine deaminase domain, wherein said contacting is reached using a single transfection event. In other words, within this embodiment, the cell in which the targeted nucleotide editing is desired is transfected using a transfection medium comprising both the first and the second fusion protein, or construct(s) encoding the same. In case both fusion proteins comprise a CRISPR-nuclease and both C to T (or G to A) and A to G (or T to C) conversion(s) in a single target sequence is desired, such transfection medium may further comprise a single guide RNA that is capable of targeting both the first and second fusion protein said target sequence, for instance because both fusion proteins comprise the same CRISPR-nuclease domain.

Alternatively, at least two guide RNAs may be employed, wherein a first and second guide RNA are both capable of complexing with and targeting a fusion protein to the DNA of the cell, however their guide sequence differs in such a way that they are capable of hybridizing to different sites in the DNA of the cell, or at the same site but each at a different strand of the duplex DNA. In the latter case, the guide sequence of the first guide RNA may be antisense to the target sequence and the guide sequence of the second guide RNA may be sense to the target sequence. In this case, combinations of C to T changes and G to A changes in the target sequence may be accomplished in case the fusion protein comprises a cytosine deaminase. Likewise, combinations of A to G and T to C conversions may be accomplished in case the fusion protein comprises an adenine deaminase. In case a C to T (or G to A) is desired at a first target sequence of the DNA of the cell, and an A to G (or T to C) conversion is desired at a second (different) target sequence of said DNA, the method of the invention may comprise contacting said DNA with at least a first and a second guide RNA, wherein the first guide RNAs is capable of targeting the first fusion protein to the first target sequence, and the second guide RNA is capable of targeting the second fusion protein to the second target sequence, wherein preferably the first guide RNA is incapable, or at least to a much lesser extent, of targeting the second fusion protein to the first target sequence, and vice versa.

"Contacted" is intended to mean exposing the DNA within the cell, preferably the plant cell, to a fusion protein as defined herein. This may be reached by contacting the cell with said fusion protein (denominated herein as protein) optionally in combination with guide RNA (denominated herein as protein/RNA transfection) or with a construct encoding the same (denominated herein as nucleotide construct transfection) in such a manner that the fusion protein or construct gains access to the interior of the cell, enabling the (encoded) fusion protein to interact with the DNA comprising the target sequence. In case the nuclease domain is a CRISPR-nuclease, the contacting may be reached by contacting the cell with a construct encoding the fusion construct in combination with in vitro transcribed or synthetic guide RNA, either at the same time or consecutively.

Preferably, the method of the invention makes use of a single transfection event, which is to be understood herein as a single incubation step wherein the cell is exposed to a single transfection medium comprising the one or more fusions proteins, optional guide RNA(s) and optional further functional protein(s), or constructs encoding the same, needed for the desired editing to occur, as further detailed herein.

The methods of the invention do not depend on a particular method for introducing the fusion protein into the cell. In case of protein/RNA transfection, the fusion protein is provided to the cells as a polypeptide, optionally together with a guide RNA and/or further functional protein(s) such as an UDG inhibitor protein as defined herein, which is/are taken up into the cell interior. In case of nucleotide construct transfection, the DNA of the cell or protoplast is exposed to the fusion protein and optionally the guide RNA and/or further functional protein(s), by introducing into the cell one or more nucleic acid constructs for expression of the same in the cell. Such nucleic acid construct may be any suitable construct known in the art and which is used to deliver exogenous DNA into a host cell with the purpose of expression in the host cell of a DNA region (here the fusion protein and/or the guide RNA) comprised on the construct. Introduction of the fusion protein, guide RNA and/or further functional protein(s) or the nucleic acid construct encoding the same, may be accomplished by any method known, which permits the successful introduction of the protein or the nucleic acid construct into the cells, and which, in case of a nucleic acid construct, results in the expression of the introduced nucleic acid. Methods include but are not limited to such methods as transfection, microinjection, electroporation, nucleofection and lipofection. Preferably, a PEG transfection is used, as further detailed herein below.

In the case of nucleic acid construct transfection, the fusion protein, and where applicable the guide RNA, and/or further functional protein(s), are preferably introduced in the cell using the same nucleic acid construct. In other words, the nucleic acid construct is for expression of both the fusion protein and the guide RNA in the cell. Optionally, the fusion protein, one or more guide RNAs and/or further functional proteins are introduced in the cell using different nucleic acid constructs. In any case, it is preferred that the nucleic acid sequence encoding the proteins (i.e. the fusion protein and/or further functional protein(s)) and the nucleic acid sequence encoding the guide RNA are under control of different promoters. For example, the guide RNA may, preferably, be under control of, i.e. operably linked to, a pol III promoter (such as U6 and H1) preferably for expression in the cells type of interest, e.g. for expression in plants if the cell of the method of the invention is a plant cell; RNA pol III promoters, such as U6 and H1, are commonly used to express these small RNAs (see e.g. Ma et al. Molecular Therapy Nucleic Acids (2014) 3, e161).

For example, the fusion protein and/or further functional protein(s) may, preferably, be under control of a constitutive promotes, preferably for expression in the cells type of interest, e.g. for expression in plants if the cell of the method of the invention is a plant cell, such the 35S promoter (e.g. the 35S promoted from cauliflower mosaic virus (CaMV); Odell et al. Nature 313:810-812; 1985). Other suitable constitutive promoters include but are not limited to the cassava vein mosaic virus (CsVMV) promoter, and the sugarcane bacilliform badnavirus (ScBV) promoter (see e.g.

Samac et al. Transgenic Res. 2004 August; 13(4):349-61.) Other constitutive promoters include, for example, the core promoter of the Rsyn7 promoter and other constitutive promoters disclosed in WO 99/43 838 and U.S. Pat. No. 6,072,050; ubiquitin (Christensen et al., Plant Mol. Biol. 12:619-632, 1989 and Christensen et al., Plant Mol. Biol. 18:675-689, 1992); pEMU (Last et al., Theor. Appl. Genet. 81:581-588, 1991); AA6 promoter (WO2007/069894); and the like.

The nucleic acid constructs may also include transcription termination regions. Where transcription terminations regions are used, any termination region may be used in the preparation of the nucleic acid constructs.

In a preferred embodiment, the nucleic acid construct is for transient expression. In other words, in case the cell of the method of the invention is a plant cell, the expression in the plant material is temporary as a consequence of the non-permanent presence of the nucleic acid construct. Expression may be transient, for instance when the construct is not integrated into the host genome. For example, fusion protein, guide RNA and/or further functional protein(s), or construct(s) expressing the same, are transiently provided to a plant cell, followed by a decline in the amount of one or more of the components. Subsequently, the plant cell, progeny of the plant cell, and plants which comprise the plant cell wherein the duplex DNA has been altered, comprise a diminished amount of one or more of the components used in the method of the invention, or no longer contain one or more of the components.

In conjunction with any of the methods and preferred embodiments as disclosed herein, the nucleic acid construct may be optimized for increased expression in the transformed cell, preferably a plant cell. In this embodiment, there is provided for the method of the invention, wherein the nucleic acid sequence encoding the fusion protein is codon optimized for expression in the the cells type of interest, e.g. for expression in plant cells if the cell of the method of the invention is a plant cell. That is, the nucleic acid construct encoding the fusion protein can be synthesized using plant-preferred codons for improved expression. See, for example, Campbell and Gowri, (Plant Physiol. 92: 1-11, 1990) for a discussion of host-preferred codon usage. Methods are available in the art for synthesizing plant-preferred genes (see, for example, Murray et al., Nucleic Acids Res. (1989) 17:477-498, or Lanza et al. (2014) BMC Systems Biology 8:33-43).

In case the cell of the method of the invention is a plant cell, PEG transformation may be used in the method of the invention to introduce into the plant cell the fusion protein, where applicable the guide RNA and/or further functional proteins(s), or nucleic acid construct(s) encoding the same. Polyethylene glycol (PEG) is a polyether compound with many applications from industrial manufacturing to medicine. PEG is also known as polyethylene oxide (PEO) or polyoxyethylene (POE). The structure of PEG is commonly expressed as H—(O—CH2-CH2)n-OH. Preferably, the PEG used in the method according to the invention is an oligomer and/or polymers, or mixtures thereof with a molecular mass below 20,000 g/mol. PEG-mediated gene transformation has been known since 1985. The first method for plant protoplast transformation utilized PEG (Krens et al. (1982) Nature 296: 72-74; Potyrykus et al. (1985) Plant Mol. Biol. Rep. 3:117-128; Negrutiu et al. (1987) Plant Mol. Biol. 8: 363-373). The technique is applicable to protoplasts from many different plants (Rasmussen et al. (1993) Plant Sci. 89: 199-207). PEG is thought to stimulate transformation by precipitating the DNA, in the presence of divalent cations, onto the surface of the plant protoplasts from where it then becomes internalized (Maas & Werr (1989) Plant Cell Rep. 8: 148-151).

Preferably, the method of the invention comprises contacting the plant cell with an aqueous medium, wherein the aqueous medium comprises the fusion protein, and optionally the guide RNA and/or further functional protein(s), or constructs encoding the same, and wherein the aqueous medium comprises polyethylene glycol (PEG) and is substantially free of glycerol. Glycerol is a simple polyol compound. It is a colorless, odorless, viscous liquid that is sweet-tasting and generally considered non-toxic. Glycerol is commonly used in buffers, media, and the like, used in biological sciences. Glycerol is used to stabilize proteins in solutions and/or as an anti-freeze agent, so that the proteins and enzymes can be kept at low temperature. For example, CAS9 protein is commonly sold in the form of a storage solution comprising high levels of glycerol (e.g. up to 50%; see for example, www.neb.com/products/m0386-cas9-nuclease-s-pyogenes#pd-description). Thus whereas glycerol is used to stabilize proteins in solution, it was found that in the context of the current invention, the presence of such glycerol in the aqueous medium comprising the fusion protein reduced overall efficacy of the method (e.g. in providing plant cell having a targeted alteration in a DNA molecule). Indeed when glycerol concentration is too high in the aqueous medium, results showed that no plant cell having a targeted alteration in a DNA molecule may be obtained at all.

The skilled person understands that the allowable concentration of glycerol may, to some extent, depend on the experimental settings and, based on the current disclosure, the skilled person will have no problems determining such maximal allowable concentration, and above which the efficacy of the method of the current invention is reduced. In a preferred embodiment, the aqueous medium comprising the plant cells comprises less than 0.1% (v/v) glycerol, preferably the aqueous medium is free of (detectable) glycerol. In other words, the end concentration glycerol in de aqueous medium comprising the plant cells is preferably less than 0.1% (v/v), for example, less than 0.08%, 0.05%, 0.01%, 0.005%, 0.001% (v/v) glycerol.

Preferably, for transfection, an aqueous solution of plant cells or protoplasts of about 10000-2 000 000 plant cells per milliliter of aqueous medium is contacted with the fusion protein and optionally the guide RNA and/or further functional proteins, or expression construct(s) encoding the same, and PEG solution. Preferably, guide RNA and/or further functional proteins, or expression construct(s) encoding the same are added to an amount of aqueous solution comprising about 1 000 000 plant cells per milliliter, which is subsequently admixed with PEG solution, preferably at a ratio of about 1:1.

In an embodiment wherein the nuclease domain is or is derived from a CRISPR-nuclease and wherein transfection is performed using different constructs encoding either the fusion protein or the guide RNA, the weight ratio of fusion protein expressing plasmid relative to guide RNA expressing plasmid is in the range of 10:1 to 1:200, such as 2:1 to 1:10, or 1:1 to 1:5, more preferred in the range of 1:1 to 1:3, such as about 1:2. Preferably, at least 0.1 µg of fusion protein expressing plasmid is used per mL transfection solution (comprising both the cells in aqueous solution and PEG), such as at least 0.5 µg, at least 1 µg, at least 5 µg, or at least 10 µg, or about 10 µg. In an embodiment, said at least 0.1 µg, such as at least 0.5 µg, at least 1 µg, at least 5 µg, or at least 10 µg, or about 10 µg of fusion protein expressing plasmid is combined with guide RNA expressing plasmid in the appropriate weight range as taught herein, and said combination of fusion protein expressing plasmid and guide RNA expressing plasmid is combined with 10,000-10,000,000, preferably about 50,000-5,000,000, more preferably about 100,000-1,000,000, for example about 500,000 plant cells or plant protoplasts.

In another preferred embodiment there is provided for the method of the invention wherein the aqueous medium does not comprise any plasmid or vector material, in particular any plasmids material or vector material that encodes for a fusion protein. Having such vector present in the medium may cause the undesired introduction thereof in the DNA molecule in the plant or plant cell. In an embodiment for transfection with the fusion protein, guide RNA and/or further functional proteins, or constructs encoding the same, the plant cells or plant protoplasts may be present in a volume of about 500 μl. In an embodiment, the volume ratio of plant cell/plant protoplast (including fusion protein/guide RNA) to PEG solution, which is preferably a solution comprising 400 g/L PEG 4000 and 0.1M $Ca(NO_3)_2$, is in the range of 2:1 to 2:3, and preferably about 1:1.

In case of protein/RNA transfection (i.e. transfection of the fusion protein, optionally together with the guide RNA and/or further functional protein(s)), desirable results are obtained when the aqueous medium aqueous medium comprising the plant cells comprises 2-80 nanomolar (nM) fusion protein. Thus where the concentration may, for example, vary between 1 and 200 nM, in a preferred embodiment the concentration is between 2-80 nM, for example between 5-70 nM, between 10-50 nM or between 20-40 nM. The concentration of the guide RNA in the aqueous medium, is, within the context of the invention disclosed herein, preferably within certain ranges. More in particular it was found that using a concentration of 30-600 nanomolar of the guide RNA in the aqueous medium improves the results obtained (e.g. in providing plant cells having a targeted alteration in a DNA molecule). Thus, for example, a concentration of 10-1000 nM guide RNA (total concentration in case more than one different guide RNAs are used simultaneously used in the of the invention) may be used, but preferable the concentration is between 30-600 nM, for example between 50-400 nM, for example, between 100-300 nM, for example, between 150-250 nM. Preferably, the molar ratio between the fusion protein and guide RNA in the aqueous medium is from 1:300 to 8:3, preferably the molar ratio is 1:20. For example, the molar ratio may from 1:1-1:50, or from 1:5-1:30, or from 1:1 to 8:3, and any other ratio within these preferred ratio's. Preferably the concentration and ratio of the fusion protein and the guide RNA is within both the given concentration ranges and the given molar ratios.

Within the context of the current invention it was found that preferably the concentration of the PEG, for both nucleic acid construct and for protein/RNA transfection, is within certain ranges. In particular, the aqueous medium comprising the plant cells comprises 100-400 mg/ml PEG. So the final concentration of PEG is between 100-400 mg/ml, for example, between 150 and 300 mg/ml, for example between 180 and 250 mg/ml. A preferred PEG is PEG 4000 Sigma-Aldrich no. 81240. (i.e. having an average Mn 4000 (Mn, the average molecular weight is the total weight of all the polymer molecules in a sample, divided by the total number of polymer molecules in a sample.). Preferably the PEG used has an Mn of about 1000-10,000, for example between 2000-6000).

As already detailed herein, in a highly preferably embodiment, protein/RNA transfection is performed using an aqueous medium comprising the plant cells, wherein said medium further comprises:
- 2-80 nanomolar (nM) fusion protein, wherein said fusion protein comprises a CRISPR-nuclease;
- 30-600 nanomolar (nM) guide RNA;
- less than 0.1% (v/v) glycerol;
- 100-400 mg/ml PEG, and
- 10,000-2,000,000 plant cells/ml.

It was found that this combination of parameters is surprisingly effective in providing plant cells having a targeted alteration in a DNA molecule. Indeed it was found that deviations of the above parameters may reduce efficiency and/or efficacy. In addition, it was found that efficiency and/or efficacy of the method of the invention is improved when PEG is added to the aqueous medium after the fusion protein and optionally the guide RNA are provided to the medium. Thus, whereas PEG may be added to the aqueous medium before the fusion protein and optionally the guide RNA are provided to the medium, preferably the aqueous medium is first provided with the fusion protein and optionally the guide RNA, and after which the PEG is provided to the medium. Preferably the time between adding the fusion protein and the optionally guide RNA and the PEG is between 5 seconds and 10 minutes, but may be shorter or longer, if so desired.

Although not limited thereto, the plant cells are preferably contacted with protein(s), RNA or constructs encoding the same, as defined herein for a period of at least 5 minutes, for example for a period of between 5 minutes and 24 hours, or between 5 minutes and 6 hours, or between 5 minutes and 60 minutes, or between 5 minutes and 30 minutes, or between 5 minutes and 25 minutes. Contacting may be at any suitable temperature, for example a temperature between 4 degrees Celsius and 40 degrees Celsius, preferably between 10 degrees Celsius and 30 degrees Celsius, for example at room temperature. Moreover, the skilled person will understand that next to the specific requirement defined herein with respect to the medium, it may be any suitable medium. For example, the medium has preferably a pH value of between 5-8, preferably between 6-7.5. In an embodiment, PEG transfection may be allowed to take place for a period of time in the range of 10-60 minutes, such as 15-40 minutes, preferably about 20 minutes.

After transfection, a 0.1-0.6 M, such as a 0.2-0.4 M, or about 0.275 M, $Ca(NO_3)_2$ solution may be added to the transfection solution taught above. Preferably, about 8-12 times, such as about 10 times the volume of the transfection solution taught above may be used prior to harvesting the cells or protoplasts by centrifugation and resuspension in culture medium for further cultivation.

According to a further preferred embodiment, there is provided for a method of the invention wherein the plant cells are further cultivated, i.e. after being contacted with the aqueous medium, as detailed herein, in the presence of feeder plant cells, preferably wherein the feeder plant cells are plant protoplasts, preferably wherein the feeder plant cells are of the same plant species as the plant cells to be edited, preferably wherein the feeder plant cells are provided in the form of a feeder disc, preferably containing 50000-250000 feeder plant cells.

The skilled person knows how to cultivate protoplasts in the presence of feeder cells, for example as detailed in the examples. It was found that the presence of feeder cells during the cultivation period after the plant cells have been contacted with the aqueous medium that is substantially free of glycerol, but comprises the fusion protein and optionally the guide RNA and the PEG, may increase overall efficacy and/or efficacy of the method according to the invention. This is in particular true when the feeder cells are of the same plant species as the plant cells that were contacted with the fusion protein and/or the guide RNA in the aqueous medium, and in particular when an amount of 50000-250000 feeder plant cells per feeder disc is used (normally one feeder disc per experiment is used).

The skilled person knows other techniques on how to cultivate protoplast in the presence of feeder cells, for example as detailed in Plant Science Letters (1984) 33 (3): 293-302; doi:10.1016/0304-4211(84)90020-8 or described in various handbooks including Plant Cell and Tissue Culture (ISBN 0-7923-2493-5; edited by Vasil and Thorpe; Kluwer Academic Publishers).

Also contemplated is for a method of the invention wherein the individual protoplasts are further cultivated into plant cells comprising a plant cell wall, plant calli, and/or plants.

The method of the invention is in particular suitable for targeting, within the DNA molecule, a nucleotide sequence, for example gene or promoter, that confers one or more of the following traits: herbicide tolerance, drought tolerance, male sterility, insect resistance, abiotic stress tolerance, modified fatty acid metabolism, modified carbohydrate metabolism, modified seed yield, modified oil percent, modified protein percent, and resistance to bacterial disease, fungal disease or viral disease, although it may be used to target any kind of sequence within the DNA molecule.

According to another preference, in the method of the invention two or more guide RNAs are used. The two or more guide RNAs may direct the fusion proteins of the method of the invention to the same site in the DNA duplex, or to a different site (for example in order to introduce more than one nick, either in the same strand or in any other strand).

According to another preference the fusion protein, where applicable the guide RNA, and/or the construct encoding the same, is transiently expressed in the cell, preferably the plant cells, as already discussed herein elsewhere.

With the method according to the invention an alteration is introduced in the duplex DNA in cells, preferably in plant cells. Preferably, said targeted alteration may comprise modification of at least one base pair. For example, 1, 2, 3, 4, 5, 6, 7, 8, 9, 10 or more base pairs may be altered with the method of the invention. More than one modification may be introduced in a single experiment, and/or the experiment may be repeated to introduce subsequent alteration in the duplex DNA in the cell. Preferably, more than one base pair is altered in a single transfection event with the method of the invention. Preferably, any combination of C to T, G to A, A to G and T to C alterations are made in a single transfection event. The invention therefore also provides for combinations of fusion proteins in a mixture or composition, preferably for use in the method of the invention. Preferably such mixture or composition comprises both a first and a second fusion protein, wherein the first fusion protein is a fusion protein as defined herein comprising a cytosine deaminase domain, and the second fusion protein is a fusion protein as defined herein having an adenine deaminase domain. Said first fusion protein may be a fusion protein consisting of or comprising the sequence of SEQ ID NO: 2, or a variant thereof, and said second fusion protein may be a fusion protein consisting of or comprising the sequence of SEQ ID NO: 4, or a variant thereof. Said first fusion protein may be a fusion protein encoded by a nucleotide sequence comprising or consisting of SEQ ID NO: 1, or a variant thereof, and said second fusion protein may be a fusion protein encoded by a nucleotide sequence comprising or consisting of SEQ ID NO: 3, or a variant thereof. The mixture may comprise the fusion proteins in protein form or as constructs encoding the same. Said mixture may comprise a first construct encoding the first fusion protein or a second construct encoding the second fusion protein. Preferably, said first construct comprises SEQ ID NO: 1, or a variant thereof, or encodes SEQ ID NO: 2, or a variant thereof, and said second construct comprises SEQ ID NO: 3, or a variant thereof, or encodes SEQ ID NO: 4, or a variant thereof. Alternatively, the mixture may comprise a construct encoding both the first and the second fusion protein. Preferably, said construct comprises both SEQ ID NO: 1 and 3, or variants thereof, or encodes both SEQ ID NO: 2 and 4, or variants thereof. Optionally, the above indicated mixtures may further comprise one or more guide RNAs, or constructs encoding the same, as defined herein. Optionally said one or more guide RNAs are encoded by a construct further encoding the one more fusion protein of the method of the invention. Optionally, said construct further encodes both a fusion protein comprising a cytosine deaminase domain as defined herein and a fusion protein comprising an adenine deaminase domain as defined herein.

In case the cell of the method of the invention is a plant cell, the method may further comprise the step of regenerating a plant or descendent thereof comprising the targeted alteration. The skilled person is well aware of methods and protocols of regenerating a plant from a plant cell. Progeny, descendant's, variants, and mutants of the regenerated plants are also included within the scope of the invention, provided that these parts comprise the targeted alteration introduced with the method according to the invention.

Provided herein are the use of a fusion protein or construct encoding the same, for targeted nucleotide editing in a cell, preferably a plant cell, as detailed herein above. Also provided is a plant, plant part, seed, or plant cell obtained by any of the methods detailed herein above, wherein the plant, plant part, plant product, seed, or plant cell is modified by comprising the targeted alteration when compared to a control plant cell, and wherein the control plant cell is plant cell before the targeted alteration was introduced by any of the methods detailed herein above. Optionally, said plant product (e.g. plant oil, plant protein, plant carbohydrates) may be non-propagating.

The invention further provides for a kit, preferably for use in the method of the invention. Said kit preferably comprises at least two fusion proteins, i.e. at least a first and a second fusion protein, or (a) construct(s) encoding the same according, to the invention, wherein the first fusion protein comprises a cytosine deaminase domain, and the second fusion protein comprises an adenine deaminase domain. In other words, the kit of the invention may comprise a first vial comprising:

both the first and second fusion protein,
a construct encoding the first and second fusion protein, or
a construct encoding the first fusion protein and a construct encoding the second fusion protein.

Alternatively, the kit of the invention may comprise
a first vial comprising the first fusion protein or a construct encoding the first fusion protein, and
a second vial comprising the second fusion protein or a construct encoding the second fusion protein.

The kit may further comprise one or more further vials each comprising one or more guide RNAs. Optionally, these one or more guide RNAs are comprised within or included in the first and/or second vial as defined herein above. The volume of the vials of the kit are preferably between 1 and 5 mL or between 1 and 10 mL or between 1 and 25 mL.

Having now generally described the invention, the same will be more readily understood through reference to the following examples which are provided by way of illustration and is not intended to be limiting of the present invention.

EXAMPLES

Example 1

Programmable Editing of a Target Base at the Lin5 Locus in Plant Cells
Constructs A construct comprised of three components, the rat APOBEC deaminase (rAPOBEC1), the Cas9 protein and the UDP-uracil glycosylase inhibitor protein UGI were assembled to create a fusion protein. The rAPOBEC1 sequence was codon optimized for expression in *Solanum* species and flanked by NcoI/KpnI sites for cloning at the N terminus of Cas9. A 6× His tag was also introduced to the 5' end of this sequence. The UGI sequence was also codon optimized for *Solanum* species and synthesized together with a nuclear localization signal (NLS) and flanked by AgeI/XhoI sites. A vector containing the Cas9 ORF (pET28::Cas9) was then digested with the enzymes NcoI and XhoI for isolation of the vector backbone and with KpnI/AgeI to isolate a fragment of the Cas9 ORF. The rAPOBEC1, Cas9, UGI-NLS and vector fragments were then combined in a single ligation and clones consisting of all the fragments were isolated, giving the construct pET28::rAPOBEC1-Cas9-UGI-NLS. This construct was used as a template for mutagenesis of either the D10 or H840 amino acid residues of the Cas9 ORF into the amino acid alanine, thus creating nickase versions (D10A or H840A) of the original construct. The pET28::rAPOBEC1-Cas9-UGI-NLS and the nickase derivatives were then amplified by PCR and cloned into the Gateway compatible entry vector pDONR221. They were then transferred into the plant expression destination vector pK2GW7 that carries the 35S promoter. Plasmid DNA of the constructs pK2GW7::rAPOBEC1-Cas9-UGI-NLS (KG10012), pK2GW7::rAPOBEC1-Cas9 D10A-UGI-NLS (KG10098) and pK2GW7::rAPOBEC1-Cas9 H840A-UGI-NLS (KG10112) were then isolated for tomato protoplast transfection. A construct carrying the adenine deaminase fused to the N terminus of the Cas9 nickase (TadA-Cas9 D10A-NLS) was synthesized in pDONR221. This cassette was then also transferred to the plant expression vector K2GW7, giving the construct KG10436, and plasmid DNA for protoplast transfection was isolated. The DNA and protein sequences of these constructs are shown in FIGS. 1A-1E.

Two sgRNAs that are able to target the fusion protein(s) to the tomato LIN5 locus were designed and synthesized. This included the sequence of the sgRNA linked to the *A. thaliana* U6 promoter for expression in plant cells. The plasmids carrying these cassettes (KG10075 and KG10252) were then isolated for tomato protoplast transfection.
Protein Expression and Purification The *E. coli* strain BL21 DE3 containing the pET28::rAPOBEC1-Cas9-UGI-NLS expression plasmid was grown in LB medium supplemented with kanamycin (50 µg/ml) to an OD600=0.6 and IPTG was then added a final concentration of 1 mM to induce protein production. These cultures were then grown overnight in a shaker at 22° C. for optimal protein expression. The recombinant proteins were then purified using the Ni-NTA Spin Kit (Qiagen) following the manufacturers protocol. Protein production was then confirmed by separation of the purified proteins on a 10% polyacrylamide gel (Invitrogen) followed by Coomassie staining. The purified proteins were then dialysed against a buffer (G) consisting of 20 mM HEPES, 150 mM KCl, 1 mM DTT and 10% glycerol using 20K Slide-a-Lyzer dialysis cassettes (Thermo Scientific) overnight at 4° C. The protein was then removed from the cassette and passed over an Amicon Ultra-4 100K Centrifugation Filter (Millipore). The protein on the filter was washed with 1× PBS buffer (NaCl, 80 g/l; KCl, 2 g/l; $Na_2HPO_4$, 14.4 g/l; $KH_2PO_4$, 2.4 g/l; pH7.4) and then finally washed from the filter using 200 µl 1× PBS buffer. The concentration of the Cas9 protein was the quantified on a 10% polyacrylamide gel using a commercial Cas9 protein (M0641, New England Biolabs, 166 ng/µl) as a standard followed by Coomassie gel staining.
LIN5 sgRNA Synthesis The LIN5 sgRNA from the plasmid KG10075 was amplified using primers, whereby the forward primer also included the T7 polymerase promoter. The PCR products were then precipitated and purified over Probe Quant G50 Micro column (GE Healthcare) and then used as a template for in vitro RNA synthesis using the Ampliscribe T7 Flash Transcription Kit (Epicentre). The sgRNAs was then purified and concentrated using the ssDNA/RNA Clean and Concentrator kit (ZymoResearch) and quantified on the Qubit.
Tomato Protoplast Isolation and Transfection In vitro shoot cultures of *Solanum lycopersicon* var *Moneyberg* were maintained on MS20 medium with 0.8% agar in high plastic jars at 16/8 h photoperiod of 2000 lux at 25° C. and 60-70% RH. Young leaves (1 g) were gently sliced perpendicularly to the mid nerve to ease the penetration of the enzyme mixture. Sliced leaves were transferred to the enzyme mixture (2% Cellulase Onozuka RS, 0.4% Macerozyme Onozuka R10 in CPW9M) and cell wall digestion was allowed to proceed overnight in the dark at 25° C. The protoplasts were filtered through a 50 µm nylon sieve and were harvested by centrifugation for 5 minutes at 800 rpm. Protoplasts were resuspended in CPW9M (Frearson, 1973) medium and 3 mL CPW18S (Frearson, 1973) was added at the bottom of each tube using a long-neck glass Pasteur pipette. Live protoplasts were harvested by centrifugation for 10 minutes at 800 rpm as the cell fraction at the interface between the sucrose and CPW9M medium. Protoplasts were counted and resuspended in MaMg (Negrutiu, 1987) medium at a final density of $10^6$ per mL.

For the protoplast transfections 10 µg of the rAPOBEC1-Cas9-UGI-NLS expression plasmids (or the nickase variants) or the TadA-Cas9 D10A-NLS expression plasmids together with 20 µg of the sgRNA expressing plasmid KG10075 were mixed with 500 µL (500000 protoplasts) of the protoplast suspension and 500 µL of PEG solution (400 g/l poly(ethylene glycol) 4000, Sigma-Aldrich #81240; 0.1M $Ca(NO_3)_2$) was then added and the transfection was allowed to take place for 20 minutes at room temperature. In other experiments 5 µg of rAPOBEC1-Cas9 D10A-UGI-NLS (KG10098) and 5 µg of TadA-Cas9 D10A-NLS (KG10436) were mixed together with 20 µg of the sgRNA expressing plasmid KG10075 and transfected to tomato protoplasts as described above. Control samples were also produced by omitting one or both of the plasmids from the transfection. When the purified rAPOBEC1-Cas9-UGI-NLS protein and LIN5 sgRNA was used, 8 pmol of the Cas9 protein resuspended in 1× PBS buffer and 150 pmol of the LIN5 sgRNA were mixed with (500000 protoplasts) of the protoplast suspension and 500 µL of PEG solution (400 g/l poly(ethylene glycol) 4000, Sigma-Aldrich #81240; 0.1M Ca(NO$_3$)$_2$) was then added and the transfection was allowed to take place for 20 minutes at room temperature.

Then, 10 mL of 0.275 M Ca(NO$_3$)$_2$ solution was added and thoroughly, but gently mixed in. The protoplasts were harvested by centrifugation for 5 minutes at 800 rpm and resuspended in 9M culture medium at a density of 0.5×10$^6$ per ml and transferred to a 4 cm diameter petri dish and an equal volume of 2% alginate solution (20 g/l Alginate-Na (Sigma-Aldrich #A0682), 0.14 g/l CaCl$_2$.2H$_2$O, 90 g/l mannitol) was added. Then 1 ml aliquots (125000 transfected protoplasts) were spread over Ca-Agar plates (72.5 g/l mannitol, 7.35 g/l CaCl$_2$.2H$_2$O, 8 g/l agar, pH5.8) and allowed to polymerize for 1 hour. When plasmid constructs had been used in the transfection, the embedded protoplasts were grown in a 4 cm tissue culture dish containing 4 ml of K8p (Kao, 1975) culture medium. When the fusion protein had been used in the transfection, we improved protoplast survival by producing "feeder" discs containing 200000 tomato protoplasts (*Moneyberg* variety) that had not been transfected but were embedded in alginate using the same protocol as above. A single disc of transfected protoplasts was then combined with a single feeder disc of protoplasts in a 4 cm tissue culture dish containing 4 ml of K8p (Kao, 1975) culture medium. To detect indels in tomato protoplasts the disc of transfected protoplasts was removed from the dish after 48 hours and the alginate was dissolved and the protoplasts were isolated. For the regeneration of calli, the protoplasts were incubated in the K8p medium for 21 days at 28° C. in the dark. After this period the discs of transfected protoplasts were transferred to solid GM medium (Tan, 1987) supplemented with 1 mg.l$^{-1}$ zeatin and 0.2 mg.l$^{-1}$ GA3 and grown for a further 3 weeks at which point the calli were approximately 0.3 mm in size. The alginate was then dissolved and the calli were spread on a fresh plate of GM medium and allowed to grow until they were approximately 1.5 mm, at which point they were once again transferred to fresh medium and then genotyped after a further 14 days.

Genotyping Protoplasts and Calli

Total genomic DNA was isolated from tomato protoplasts (48 hrs post transfection) using the DNeasy Plant Mini Kit (Qiagen). The gDNA was then used in a PCR reaction to amplify the LIN5 target sites using the following primers (Fw: 5'CACTATTGGCATGTATCACAC (SEQ ID NO: 35); Rev: 5' GTGATGCTGAGATCCCTTTAAC (SEQ ID NO:36)). This PCR product was then used as a template to generate a library from each sample which was then sequenced on the MiSeq platform (Illumina). Each sample was identified using a unique 5 bp tag. After sequencing the reads of each sample were processed to identify the number and types of sequence changes present at the target site.

Calli were genotyped directly using the direct PCR kit (Phire Plant Direct PCR kit, Thermo Scientific) and the gene specific primers described above. The resulting PCR products were then genotyped to identify which calli contained mutations at the target site. These were then transferred to MS medium supplemented with 2 mg.l$^{-1}$ zeatin and 0.1 mg.l$^{-1}$ IAA media after which regenerated tomato plantlets were rooted on MS medium supplemented with 0.5 mg.l$^{-1}$ IBA before transfer to the greenhouse.

Results

In order to demonstrate that targeted deamination of cytosines, leading to C to T transversions, is feasible in plant cells we first tested whether such events could be detected after expression of the rAPOBEC1-Cas9-UGI-NLS fusion proteins and LIN5 sgRNA from transfected plasmid constructs or after the transfection of the fusion proteins and the in vitro transcribed LIN5 sgRNA. We assumed that the deaminase activity of the APOBEC1 domain would be active on cytosines located within the 20 bps of the target site present on the guide RNA. We chose the LIN5 guide RNA (sgRNA) because it contains three cytosines located at the 5' end of the target site that are ideally positioned for deamination by the APOBEC1 domain. The efficiency of different guide RNAs in tomato protoplasts can vary significantly and therefore it is first important to test whether, and to what extent, a specific guide RNA design is active in plant cells. Therefore we first introduced the LIN5 sgRNA expression cassette present on a vector (KG10075) into tomato protoplasts together with a vector that expressed the Cas9 protein (35S:Cas9, KG10088). After 48 hours the cells were harvested and the genomic DNA was isolated. The LIN5 target sequence was then amplified from all of the cells in the sample and resulting amplicon was used to prepare a library for sequencing on the MiSeq platform. The resulting sequence reads were then analyzed for the presence of indel mutations in and around the PAM site. We found >16% of the reads carried an indel at the expected position, showing that the LIN5 sgRNA was highly active in tomato protoplasts and could therefore be used in our deamination experiments.

To test whether the deaminase activity of rAPOBEC1 could be targeted by Cas9 to cytosines in this LIN5 sequence we first transfected the constructs KG10098 (pK2GW7::rAPOBEC1-Cas9 D10A-UGI-NLS) and KG10126 (pK2GW7::rAPOBEC1-Cas9-UGI-NLS) together with the plasmid KG10075 to tomato protoplasts and after 48 hours harvested the cells and amplified the LIN5 target site from the transfected cells. In similar experiments we also introduced the purified rAPOBEC1-Cas9 D10A-UGI-NLS protein together with the in vitro transcribed LIN5 sgRNA into tomato protoplasts and also analyzed these protoplasts for C to T transitions at the LIN5 target site. The LIN5 amplicons were used for library preparation and were then sequenced on the MiSeq platform. The resulting reads were analyzed to identify any nucleotide changes that may have occurred at the LIN5 target site. As shown in FIG. 3, when the vector KG10098 was used we found a large number of sequence reads (0.8%) that contained a single C to T transition at the cytosine 6 nt from the 5' end of the target site. We also found a lower number of reads (0.08%) in which multiple cytosines on a single read had been converted to thymine. We did not detect any reads that contained indels in or around the PAM site because the vector KG10098 expresses a Cas9 nickase whose nicking activity does not lead to indel formation. Transfection of tomato protoplasts with none or only one of the vectors was also performed, but such samples never resulted in reads showing mutations at the LIN5 target site. Such C to T transitions could also be made when the construct KG10126 (pK2GW7::rAPOBEC1-Cas9-UGI-NLS) was used that is still able to introduce DNA DSBs at the target site. In this case we found that the efficiency of C to T transitions was 10 fold lower than when the rAPOBEC1-Cas9 D10-UGI-NLS nickase was expressed in the cells. However, this did demonstrate that a deaminase-Cas9 fusion protein that has retained its DSB induction activity is active in plant cells. Some of the sequence reads also contained indel mutations in and around the PAM site, sometimes in combination with transitions. This made it possible to compare the relative efficiencies of C to T transitions with that of indel formation. We found that approximately 0.89% of the reads contained an indel mutation when KG10126 was used compared with 0.8% of the reads containing a single C to T transition when KG10098 was used. Therefore, we were able to conclude that the efficiency of C to T transitions at the LIN5 target sequence is as efficient as the formation of indels.

We noticed that the indel efficiency using KG10126 was approximately 16 fold lower than when the unmodified Cas9 protein was used in our experiments. This demonstrates that the addition of the APOBEC1 and/or the UGI sequences at the N and C termini of the Cas9 protein does have a negative effect on its DSB induction capacity. We found similar results when the rAPOBEC1-Cas9 D10A-UGI-NLS protein and the LIN5 sgRNA were transfected to tomato protoplasts. Analysis of the reads derived from these protoplasts also showed C to T transitions at approximately the same efficiency and position in the LIN5 target sequence as when the same proteins had been expressed from the plasmid constructs.

In summary, this result shows that a deaminase protein can be targeted to a specific genomic sequence in plant cells by its fusion to the Cas9 protein. The C to T transitions can be produced in the coding sequence of a gene, thus altering a codon and resulting in an altered protein sequence. Therefore, this technique can be used to change individual amino acids in coding sequences that may result in improved overall plant performance. The construct KG10098 was also transfected to protoplasts together with a plasmid expressing the LIN5 sgRNA2 (KG10252) and sequencing was done to determine the efficiency of the deamination reaction at this alternative target sequence. The results are shown in FIG. 3. At this second target sequence an efficient conversion of either single or multiple cytosines to thymines was again observed.

The modified adenine deaminase (TadA) fused to the N terminus of Cas9 converts adenine to inosine that then preferentially base pairs with cytosine. This thus results in a A:T to G:C conversion activity that can be targeted to a specific genomic sequence. The pK2GW7::TadA-Cas9 D10A-NLS construct (KG10436) was transfected to tomato protoplasts together with the LIN5 sgRNA1 plasmid KG10075 and sequencing was performed on the protoplasts to determine the efficiency of A:T to C:G conversion at this target sequence. As shown in FIG. 3 we were able to detect reads in which the adenines at positions 5 and 8 had been converted to guanine. This demonstrates that targeted adenine deamination is feasible in plant cells.

The combination of both the cytosine and adenine targeted deaminases was then tested in plant cells. The constructs KG10098 and KG10436 were mixed and transfected together with the LIN5 sgRNA1 sgRNA expression plasmid to tomato protoplasts. The rAPOBEC1-Cas9 D10A-UGI-NLS (KG10098) and TadA-Cas9 D10A-NLS (KG10436) cytosine and adenine deaminases respectively are both active at the LIN5 sgRNA1 target site utilize the same sgRNA for targeting. When transfected together the deaminases may produce C to T and A to G conversions at the target sequence in a single cell. This could be detected by the presence of sequencing and would demonstrate that the deaminases can be used to together to introduce novel combinations of nucleotide changes. The results of this experiment are shown in FIG. 3. In this sample, 0.35% of the reads contained a C to T change at position 6, generated by the cytosine deaminase (KG10098), and 0.15% of the reads contained a A to G change at position 5, produced by the adenine deaminase (KG10436). Interestingly, reads were found with both a C to T change at position 6 and an A to G change at position 8 which could only have been produced through the activity of both deaminases at the same locus. Therefore, this approach shows that the cytosine and adenine deaminases can be expressed in the same plant cell(s) and are targeted to the same locus where they are able to produce different nucleotide changes. This thus increases that range of amino acid changes that can be achieved.

In order to obtain a plant with targeted C to T transitions protoplasts containing such mutations must be regenerated into mature plants. These are then genotyped to show that the mutations are not lost during the regeneration process. Tomato protoplasts were transfected with the rAPOBEC-Cas9 D10A-UGI-NLS vector (KG10098) in combination with KG10075 or KG10252. Alternatively rAPOBEC1-Cas9 D10A-UGI-NLS protein was used together with LIN5 sgRNA1. The protoplasts were then incubated in growth medium until they had formed calli that could be genotyped for the presence of C to T transitions at the LIN5 target sequence. From the KG10098 and KG10075 transfections more than 2000 calli were generated and genotyped. Approximately 1.5% (32 calli) of these were found to be heterozygous for a C to T transition at position 6 in the target sequence which corresponds well with the mutation frequency at this position found after sequencing (0.8%). Another 6 calli were shown to be homozygous for the C to T transition at position 6, demonstrating that these reagents are able to produce biallelic mutations. We found similar numbers of calli with mutations at the LIN5 target sequence when the rAPOBEC1-Cas9 D10A-UGI-NLS protein and LIN5 sgRNA1 were used. The calli were then regenerated into mature plants that were then genotyped (FIG. 4). Most of lines carried several heterozygous C to T mutations at the target region except for line 6 that contained three biallelic mutations. In each case the mutation found in the callus was present in the regenerated shoots. These results demonstrate that targeted base editing can be performed in plant protoplasts and that after regeneration mutant calli can be identified by genotyping (without application of selection) and then regenerated into mature mutant plants.

Example 2

Use of Targeted Deaminases to Introduce Herbicide Resistance in Plants

Tomato contains two copies of the gene acetolactate synthase (ALS1 and ALS2) whose protein is a target for a wide range of herbicides. Specific amino acid changes at the ALS2 positions P184 and S640, and also at the corresponding amino acids in the ALS1 protein (P186 and S642), generate proteins that are resistant to the activity of the herbicide and plant cells expressing such proteins survive herbicide application. Mutations at the both the P184 and S640 codons are dominant and can be selected for at both the single cell and the plant level. We reasoned that the rAPOBEC1-Cas9 D10A-UGI-NLS protein could be targeted to these codons in protoplasts, generating mutations that would confer herbicide resistance. Addition of the herbicide to the protoplast growth medium would select protoplasts that contained C to T transitions in and around the P184 and S640 codons and herbicide resistant calli would then be generated. Such calli can then be genotyped to identify the mutations produced at these target sites. These experiments would demonstrate that C to T transitions can be introduced at other plant loci. As we demonstrated in example 1 multiple cytosines in the target region can be altered, resulting the alteration of several adjacent amino acids. Therefore, we may be able to select herbicide resistant calli with combinations of amino acid changes that have not been previously identified that show improved resistance to ALS inhibiting herbicides. Also, as two copies of ALS are present in tomato, we wanted to assess the ability of the deaminase-Cas9 proteins to introduce mutations at both the ALS1 and ALS2 genes simultaneously in a single cell.

Based on the location of PAM sequences (NGG) around the target codons we designed three sgRNAs for both the ALS1 and ALS2 loci (FIG. 5) and then synthesized these fused to the *Arabidopsis* U6 promoter (FIG. 2). These sgRNA expression vectors were then introduced into tomato protoplasts by PEG transfection together with the rAPOBEC1-Cas9 D10A-UGI-NLS expression vector KG10098. After 48 hours the transfected protoplasts in one alginate disc were harvested for genomic DNA isolation while the other disc was incubated in growth medium containing either chlorsulfuron to select for mutations at P184 or imidazole to select for mutations at S640. The genomic DNA from the transfected protoplasts was used as a template to generate amplicons containing the target codons from both the ALS1 and ALS2 loci and these were used to prepare libraries that were then sequenced on the MiSeq platform. The sequence reads were then analyzed for the presence of C to T transitions. Calli resistant to either of the herbicides were genotyped and the mutations present at both the ALS1 and/or the ALS2 loci were identified.

FIGS. 6A-6B shows the nucleotide changes that can be expected due to a C to T transition on either the DNA strand and the amino acid changes that result from these mutations. All of the mutations indicated in FIGS. 6A-6B could be found in the sequence reads, demonstrating that the rAPOBEC1-Cas9 D10A-UGI-NLS protein is able to produce C to T transitions at the both the ALS1 and ALS2 loci. Plants were then regenerated from the herbicide resistant calli and genotyped. As shown in FIG. 7 plants were regenerated that contained for the most part heterozygous mutations at the P186 and/or P184 codons of ALS1 and ALS2 respectively. For instance, line 5 in FIG. 7, table A, contains mutations that confer herbicide resistance at both the ALS1 and ALS2 loci, indicating that a single guide RNA can be used to create mutations in members of a conserved gene family in the same cell. In this case there is a single SNP between the guide RNA used and the ALS1 target sequence but the guide RNA is still active at this locus. The genotype of the plants resistant to imazapyr is shown in FIG. 7, table B. In this case the guide RNA was only active at the ALS2 locus as the ALS1 locus lacks the corresponding PAM site. Heterozygous mutations were found that produced the S640N imazapyr resistance mutation as well as a line containing two additional heterozygous mutations (S640N, G642N).

The invention claimed is:

1. A method for targeted conversion of one or more cytosines to thymines (C-to-T) in combination with one or more adenines to guanines (A-to-G) in a target sequence in a cell, comprising
 i) contacting DNA in the cell with at least a first and a second fusion protein,
 wherein the first fusion protein comprises a CRISPR-nuclease domain and a cytosine deaminase domain and wherein the second fusion protein comprises a CRISPR-nuclease domain and an adenine deaminase domain,
 wherein the DNA is contacted transiently by at least one of:
  transiently introducing into the cell one or more DNA constructs for the combined expression of the first and second fusion proteins; and
  transiently introducing into the cell the first and second fusion proteins,
 wherein the cell is transfected using a transfection medium comprising a guide RNA and both the first and the second fusion protein, or construct(s) encoding the same,
 wherein the first and second fusion protein comprise the same CRISPR-nuclease domain; and
 ii) sequencing the DNA to identify the C-to-T and A-to-G conversions in the target sequence.

2. The method according to claim 1, wherein the CRISPR-nuclease domain is Cas9 or Cpf1.

3. The method according to claim 1, wherein the cytosine deaminase domain of the first fusion protein is selected from the group consisting of an apolipoprotein B mRNA-editing complex (APOBEC) family deaminase, an activation-induced cytosine deaminase (AID), and an ACF1/ASE deaminase, or a variant thereof, and/or wherein the adenine deaminase domain of the second fusion protein is at least one of an ADAT family deaminase, ADAR1, ADAR2 and TadA, or a variant thereof.

4. The method according to claim 1, wherein the deaminase domain in at least one of the fusion proteins is fused to the N-terminus of the nuclease domain.

5. The method according to claim 1, wherein the first fusion protein comprising a cytosine deaminase domain further comprises a Uracil DNA glycosylase inhibitor domain.

6. The method according to claim 5, wherein the Uracil DNA glycosylase inhibitor domain is fused to the C-terminus of the nuclease domain.

7. The method according to claim 1, wherein the guide RNA is contacted to the DNA by introducing into the cell one or more DNA constructs for expression of said guide RNAs in the cell.

8. The method according to claim 1, wherein the guide RNA is contacted to said DNA molecule by introducing into the cell said guide RNA.

9. The method according to claim 1, wherein the cell is a plant cell, and wherein
at least one of the fusion proteins;
the guide RNA; and/or
one or more constructs for expression of at least one of the fusion proteins and/or the guide RNA, are introduced into the plant cell using polyethylene glycol (PEG) mediated transformation.

10. The method according to claim 1, wherein the cell is a plant cell.

11. A plant, plant part, plant product, seed, or plant cell obtained by the method of claim 1 wherein the cell is a plant cell, wherein the plant, plant part, seed, or plant cell is modified by comprising the targeted alteration when compared to a control plant, plant part, seed, or plant cell.

12. A composition comprising a first fusion protein and second fusion protein as defined in claim 1, or construct(s) encoding the same, wherein the first fusion protein comprises a cytosine deaminase domain and the second fusion protein comprises an adenine deaminase domain.

13. A kit for targeted nucleotide editing of DNA in a cell comprising at least a first and a second fusion protein as defined in claim 1, wherein the first fusion protein comprises a cytosine deaminase domain and the second fusion protein comprises an adenine deaminase domain.

14. The method according to claim 9, wherein the PEG mediated transformation is conducted using an aqueous medium comprising PEG.

15. The method according to claim 10, further comprising the step of regenerating a plant or descendent thereof comprising the targeted alteration.

16. The plant, plant part, plant product, seed, or plant cell according to claim 11, wherein the control plant, plant part, seed, or plant cell is a plant, plant part, seed, or plant cell before the targeted alteration was introduced by the method.

17. The method according to claim 1, wherein the target sequence is at least one of an intron, an exon, a coding sequence and a regulatory element.

18. The method according to claim 10, wherein the DNA is contacted transiently by transiently introducing into the cell the first and second fusion proteins using an aqueous medium comprising the plant protoplasts, and wherein the medium further comprises:
2-80 nanomolar (nM) of the first and second fusion protein;
30-600 nanomolar (nM) of the guide RNA;
less than 0.1% (v/v) glycerol;
100-400 mg/ml PEG; and
10,000-2,000,000 plant protoplast cells/ml.

* * * * *

SEQUENCE LISTING

```
<160> NUMBER OF SEQ ID NOS: 95

<210> SEQ ID NO 1
<211> LENGTH: 5082
<212> TYPE: DNA
<213> ORGANISM: Artificial Sequence
<220> FEATURE:
<223> OTHER INFORMATION: Description of Artificial Sequence: Synthetic
      DNA sequence encoding the rAPOBEC-Cas9-UGI fusion protein

<400> SEQUENCE: 1
atgggtagca gccatcatca tcaccatcat atgagcagcg aaacaggtcc ggttgcagtt      60
gatccgaccc tgcgtcgtcg tattgaaccg catgaatttg aagttttttt tgatccgcgt     120
gagctgcgta aagaaacctg tctgctgtat gaaattaact ggggtggtcg tcatagcatt     180
tggcgtcata ccagccagaa taccaataaa catgtggaag tgaacttcat cgagaaattt     240
accaccgaac gttattttg tccgaatacc cgttgtagca ttacctggtt tctgagctgg     300
tcaccgtgtg gtgaatgtag ccgtgcaatt accgaatttc tgagccgtta tccgcatgtt     360
accctgttta tctatattgc ccgtctgtat catcatgcag atccgcgtaa tcgtcagggt     420
ctgcgtgatc tgattagcag cggtgttacc attcagatta tgaccgaaca agaaagcggt     480
tattgctggc gtaattttgt gaattatagc ccgagcaatg aagcacattg gcctcgctat     540
ccgcatctgt gggttcgtct gtatgttctg gaactgtatt gtattattct gggtctgcct     600
ccgtgtctga atattctgcg tcgtaaacag ccgcagctga cctttttac cattgcactg     660 cagagctgtc attatcagcg tctgccaccg catattctgt gggcaacagg tctgaaaagc     720
ggtagcgaaa caccgggtac aagcgaaagc gcaacaccgg aaagcgacaa aaaatacagc     780
attggtctgg acattggtac caacagcgtg ggctgggccg tgatcaccga cgagtacaag     840
gtgcccagca gaagttcaa ggtgctgggc aacaccgacc gccacagcat caagaagaac     900
ctgatcggcg ccctgctgtt cgacagcggc gagaccgccg aggccacccg cctgaagcgc     960
accgcccgcc gccgctacac ccgccgcaag aaccgcatct gctacctgca ggagatcttc    1020
```

```
agcaacgaga tggccaaggt ggacgacagc ttcttccacc gcctggagga gagcttcctg    1080
gtggaggagg acaagaagca cgagcgccac cccatcttcg gcaacatcgt ggacgaggtg    1140
gcctaccacg agaagtaccc caccatctac cacctgcgca agaagctggt ggacagcacc    1200
gacaaggccg acctgcgcct gatctacctg gccctggccc acatgatcaa gttccgcggc    1260
cacttcctga tcgagggcga cctgaacccc gacaacagcg acgtggacaa gctgttcatc    1320
cagctggtgc agacctacaa ccagctgttc gaggagaacc ccatcaacgc cagcggcgtg    1380
gacgccaagg ccatcctgag cgcccgcctg agcaagagcc gccgcctgga aacctgatc    1440 gcccagctgc ccgcgagaa gaagaacggc ctgttcggca acctgatcgc cctgagcctg    1500
ggcctgaccc ccaacttcaa gagcaacttc gacctggccg aggacgccaa gctgcagctg    1560
agcaaggaca cctacgacga cgacctggac aacctgctgg cccagatcgg cgaccagtac    1620
gccgacctgt tcctggccgc caagaacctg agcgacgcca tcctgctgag cgacatcctg    1680
cgcgtgaaca ccgagatcac caaggccccc ctgagcgcca gcatgatcaa gcgctacgac    1740
gagcaccacc aggacctgac cctgctgaag gccctggtgc gccagcagct gcccgagaag    1800
tacaaggaga tcttcttcga ccagagcaag aacggctacg ccggctacat cgacggcggc    1860
gccagccagg aggagttcta caagttcatc aagcccatcc tggagaagat ggacggcacc    1920
gaggagctgc tggtgaagct gaaccgcgag gacctgctgc gcaagcagcg caccttcgac    1980
aacggcagca tcccccacca gatccacctg ggcgagctgc acgccatcct gcgccgccag    2040
gaggacttct accccttcct gaaggacaac cgcgagaaga tcgagaagat cctgaccttc    2100
cgcatcccct actacgtggg cccctggcc cgcggcaaca gccgcttcgc ctggatgacc    2160
cgcaagagcg aggagaccat cacccctgg aacttcgagg aggtggtgga caagggcgcc    2220
agcgcccaga gcttcatcga gcgcatgacc aacttcgaca agaacctgcc caacgagaag    2280
gtgctgccca gcacagcct gctgtacgag tacttcaccg tgtacaacga gctgaccaag    2340
gtgaagtacg tgaccgaggg catgcgcaag cccgccttcc tgagcggcga gcagaagaag    2400
gccatcgtgg acctgctgtt caagaccaac cgcaaggtga ccgtgaagca gctgaaggag    2460
gactacttca gaagatcga gtgcttcgac agcgtggaga tcagcggcgt ggaggaccgc    2520
ttcaacgcca gcctgggcac ctaccacgac ctgctgaaga tcatcaagga caaggacttc    2580
ctggacaacg aggagaacga ggacatcctg gaggacatcg tgctgacccct gaccctgttc    2640 gaggaccgcg agatgatcga ggagcgcctg aagacctacg cccacctgtt cgacgacaag    2700
gtgatgaagc agctgaagcg ccgccgctac accggctggg gccgcctgag ccgcaagctt    2760
atcaacggca tccgcgacaa gcagagcggc aagaccatcc tggacttcct gaagagcgac    2820
ggcttcgcca accgcaactt catgcagctg atccacgacg acagcctgac cttcaaggag    2880
gacatccaga aggcccaggt gagcggccag ggcgacagcc tgcacgagca catcgccaac    2940
ctggccggca gccccgccat caagaagggc atcctgcaga ccgtgaaggt ggtggacgag    3000
ctggtgaagg tgatgggccg ccacaagccc gagaacatcg tgatcgagat ggcccgcgag    3060
aaccagacca cccagaaggg ccagaagaac agccgcgagc gcatgaagcg catcgaggag    3120
ggcatcaagg agctgggcag ccagatcctg aaggagcacc ccgtgagaa cacccagctg    3180 cagaacgaga gctgtacct gtactacctg cagaacggcc gcgacatgta cgtggaccag    3240
gagctggaca tcaaccgcct gagcgactac gacgtggacc acatcgtgcc ccagagcttc    3300
ctgaaggacg acagcatcga caacaaggtg ctgacccgca gcgacaagaa ccgcggcaag    3360
```

```
agcgacaacg tgcccagcga ggaggtggtg aagaagatga agaactactg cgccagctg      3420 ctgaacgcca agctgatcac ccagcgcaag ttcgacaacc tgaccaaggc cgagcgcggc      3480
ggcctgagcg agctggacaa ggccggcttc atcaagcgcc agctggtgga cccgccag       3540 atcaccaagc acgtggccca gatcctggac agccgcatga acaccaagta cgacgagaac      3600
gacaagctga tccgcgaggt gaaggtgatc accctgaaga gcaagctggt gagcgacttc      3660
cgcaaggact ccagttctca aggtgcgc gagatcaaca actaccacca cgcccacgac        3720
gcctacctga acgccgtggt gggcaccgcc ctgatcaaga agtaccccaa gctggagagc      3780
gagttcgtgt acggcgacta caaggtgtac gacgtgcgca agatgatcgc caagagcgag     3840
caggagatcg gcaaggccac cgccaagtac ttcttctaca gcaacatcat gaacttcttc     3900
aagaccgaga tcaccctggc caacggcgag atccgcaagc gccccctgat cgagaccaac      3960
ggcgagaccg gcgagatcgt gtgggacaag gccgcgact cgccaccgt gcgcaaggtg        4020 ctgagcatgc cccaggtgaa catcgtgaag aagaccgagg tgcagaccgg cggcttcagc     4080
aaggagagca tcctgcccaa gcgcaacagc gacaagctga tcgcccgcaa gaaggactgg     4140
gaccccaaga gtacggcgg cttcgacagc cccaccgtgg cctacagcgt gctggtggtg      4200
gccaaggtgg agaagggcaa gagcaagaag ctgaagagcg tgaaggagct gctgggcatc     4260
accatcatgg agcgcagcag cttcgagaag aaccccatcg acttcctgga ggccaagggc    4320
tacaaggagt gaagaagga cctgatcatc aagctgccca gtacagcct gttcgagctg        4380 gagaacggcc gcaagcgcat gctggccagc gccggcgagc tgcagaaggg caacgagctg     4440
gccctgccca gcaagtacgt gaacttcctg tacctggcca gccactacga gaagctgaag     4500
ggcagccccg aggacaacga gcagaagcag ctgttcgtgg agcagcacaa gcactacctg     4560
gacgagatca tcgagcagat cagcgagttc agcaagcgcg tgatcctggc cgacgccaac     4620
ctggacaagg tgctgagcgc ctacaacaag caccgcgaca gcccatccg cgagcaggcc      4680 gagaacatca tccacctgtt caccctgacc aacctgggcg ccccgccgc cttcaagtac     4740 ttcgacacca ccatcgaccg caagcgctac accagcacca aggaggtgct ggacgccacc    4800
ctgatccacc agagcatcac cggtctgtat gaaacccgta ttgatctgag ccagctgggt    4860
ggtgatagcg gtggtagcac caatctgagc gatatcattg aaaagaaac cggcaaacag      4920 ctggtgattc aagaaagcat tctgatgctg cctgaagaag tggaagaagt tattggtaat     4980
aaaccggaaa gcgatattct ggttcatacc gcatatgatg aaagcaccga tgaaaatgtt    5040
atgctgagcg tggttccccc gaaaaaaaaa cgtaaagttt aa                         5082
```

<210> SEQ ID NO 2
<211> LENGTH: 1693
<212> TYPE: PRT
<213> ORGANISM: Artificial Sequence
<220> FEATURE:
<223> OTHER INFORMATION: Description of Artificial Sequence: Synthetic rAPOBEC-Cas9-UGI fusion protein

<400> SEQUENCE: 2

Met Gly Ser Ser His His His His His His Met Ser Ser Glu Thr Gly
1               5                   10                  15

Pro Val Ala Val Asp Pro Thr Leu Arg Arg Arg Ile Glu Pro His Glu
                20                  25                  30

Phe Glu Val Phe Phe Asp Pro Arg Glu Leu Arg Lys Glu Thr Cys Leu
            35                  40                  45

Leu Tyr Glu Ile Asn Trp Gly Gly Arg His Ser Ile Trp Arg His Thr

-continued

```
                50                  55                  60
Ser Gln Asn Thr Asn Lys His Val Glu Val Asn Phe Ile Glu Lys Phe
 65                  70                  75                  80

Thr Thr Glu Arg Tyr Phe Cys Pro Asn Thr Arg Cys Ser Ile Thr Trp
                     85                  90                  95

Phe Leu Ser Trp Ser Pro Cys Gly Glu Cys Ser Arg Ala Ile Thr Glu
                    100                 105                 110

Phe Leu Ser Arg Tyr Pro His Val Thr Leu Phe Ile Tyr Ile Ala Arg
                    115                 120                 125

Leu Tyr His His Ala Asp Pro Arg Asn Arg Gln Gly Leu Arg Asp Leu
                    130                 135                 140

Ile Ser Ser Gly Val Thr Ile Gln Ile Met Thr Glu Gln Glu Ser Gly
145                 150                 155                 160

Tyr Cys Trp Arg Asn Phe Val Asn Tyr Ser Pro Ser Asn Glu Ala His
                    165                 170                 175

Trp Pro Arg Tyr Pro His Leu Trp Val Arg Leu Tyr Val Leu Glu Leu
                    180                 185                 190

Tyr Cys Ile Ile Leu Gly Leu Pro Pro Cys Leu Asn Ile Leu Arg Arg
                    195                 200                 205

Lys Gln Pro Gln Leu Thr Phe Phe Thr Ile Ala Leu Gln Ser Cys His
                    210                 215                 220

Tyr Gln Arg Leu Pro Pro His Ile Leu Trp Ala Thr Gly Leu Lys Ser
225                 230                 235                 240

Gly Ser Glu Thr Pro Gly Thr Ser Glu Ser Ala Thr Pro Glu Ser Asp
                    245                 250                 255

Lys Lys Tyr Ser Ile Gly Leu Asp Ile Gly Thr Asn Ser Val Gly Trp
                    260                 265                 270

Ala Val Ile Thr Asp Glu Tyr Lys Val Pro Ser Lys Lys Phe Lys Val
                    275                 280                 285

Leu Gly Asn Thr Asp Arg His Ser Ile Lys Lys Asn Leu Ile Gly Ala
                    290                 295                 300

Leu Leu Phe Asp Ser Gly Glu Thr Ala Glu Ala Thr Arg Leu Lys Arg
305                 310                 315                 320

Thr Ala Arg Arg Arg Tyr Thr Arg Arg Lys Asn Arg Ile Cys Tyr Leu
                    325                 330                 335

Gln Glu Ile Phe Ser Asn Glu Met Ala Lys Val Asp Asp Ser Phe Phe
                    340                 345                 350

His Arg Leu Glu Glu Ser Phe Leu Val Glu Glu Asp Lys Lys His Glu
                    355                 360                 365

Arg His Pro Ile Phe Gly Asn Ile Val Asp Glu Val Ala Tyr His Glu
                    370                 375                 380

Lys Tyr Pro Thr Ile Tyr His Leu Arg Lys Lys Leu Val Asp Ser Thr
385                 390                 395                 400

Asp Lys Ala Asp Leu Arg Leu Ile Tyr Leu Ala Leu Ala His Met Ile
                    405                 410                 415

Lys Phe Arg Gly His Phe Leu Ile Glu Gly Asp Leu Asn Pro Asp Asn
                    420                 425                 430

Ser Asp Val Asp Lys Leu Phe Ile Gln Leu Val Gln Thr Tyr Asn Gln
                    435                 440                 445

Leu Phe Glu Glu Asn Pro Ile Asn Ala Ser Gly Val Asp Ala Lys Ala
                    450                 455                 460

Ile Leu Ser Ala Arg Leu Ser Lys Ser Arg Arg Leu Glu Asn Leu Ile
465                 470                 475                 480
```

```
Ala Gln Leu Pro Gly Glu Lys Asn Gly Leu Phe Gly Asn Leu Ile
            485                 490                 495

Ala Leu Ser Leu Gly Leu Thr Pro Asn Phe Lys Ser Asn Phe Asp Leu
            500                 505                 510

Ala Glu Asp Ala Lys Leu Gln Leu Ser Lys Asp Thr Tyr Asp Asp Asp
            515                 520                 525

Leu Asp Asn Leu Leu Ala Gln Ile Gly Asp Gln Tyr Ala Asp Leu Phe
            530                 535                 540

Leu Ala Ala Lys Asn Leu Ser Asp Ala Ile Leu Leu Ser Asp Ile Leu
545                 550                 555                 560

Arg Val Asn Thr Glu Ile Thr Lys Ala Pro Leu Ser Ala Ser Met Ile
            565                 570                 575

Lys Arg Tyr Asp Glu His His Gln Asp Leu Thr Leu Leu Lys Ala Leu
            580                 585                 590

Val Arg Gln Gln Leu Pro Glu Lys Tyr Lys Glu Ile Phe Phe Asp Gln
            595                 600                 605

Ser Lys Asn Gly Tyr Ala Gly Tyr Ile Asp Gly Gly Ala Ser Gln Glu
            610                 615                 620

Glu Phe Tyr Lys Phe Ile Lys Pro Ile Leu Glu Lys Met Asp Gly Thr
625                 630                 635                 640

Glu Glu Leu Leu Val Lys Leu Asn Arg Glu Asp Leu Leu Arg Lys Gln
            645                 650                 655

Arg Thr Phe Asp Asn Gly Ser Ile Pro His Gln Ile His Leu Gly Glu
            660                 665                 670

Leu His Ala Ile Leu Arg Arg Gln Glu Asp Phe Tyr Pro Phe Leu Lys
            675                 680                 685

Asp Asn Arg Glu Lys Ile Glu Lys Ile Leu Thr Phe Arg Ile Pro Tyr
            690                 695                 700

Tyr Val Gly Pro Leu Ala Arg Gly Asn Ser Arg Phe Ala Trp Met Thr
705                 710                 715                 720

Arg Lys Ser Glu Glu Thr Ile Thr Pro Trp Asn Phe Glu Glu Val Val
            725                 730                 735

Asp Lys Gly Ala Ser Ala Gln Ser Phe Ile Glu Arg Met Thr Asn Phe
            740                 745                 750

Asp Lys Asn Leu Pro Asn Glu Lys Val Leu Pro Lys His Ser Leu Leu
            755                 760                 765

Tyr Glu Tyr Phe Thr Val Tyr Asn Glu Leu Thr Lys Val Lys Tyr Val
            770                 775                 780

Thr Glu Gly Met Arg Lys Pro Ala Phe Leu Ser Gly Glu Gln Lys Lys
785                 790                 795                 800

Ala Ile Val Asp Leu Leu Phe Lys Thr Asn Arg Lys Val Thr Val Lys
            805                 810                 815

Gln Leu Lys Glu Asp Tyr Phe Lys Lys Ile Glu Cys Phe Asp Ser Val
            820                 825                 830

Glu Ile Ser Gly Val Glu Asp Arg Phe Asn Ala Ser Leu Gly Thr Tyr
            835                 840                 845

His Asp Leu Leu Lys Ile Ile Lys Asp Lys Asp Phe Leu Asp Asn Glu
            850                 855                 860

Glu Asn Glu Asp Ile Leu Glu Asp Ile Val Leu Thr Leu Thr Leu Phe
865                 870                 875                 880

Glu Asp Arg Glu Met Ile Glu Glu Arg Leu Lys Thr Tyr Ala His Leu
            885                 890                 895
```

```
Phe Asp Asp Lys Val Met Lys Gln Leu Lys Arg Arg Tyr Thr Gly
            900                 905                 910

Trp Gly Arg Leu Ser Arg Lys Leu Ile Asn Gly Ile Arg Asp Lys Gln
        915                 920                 925

Ser Gly Lys Thr Ile Leu Asp Phe Leu Lys Ser Asp Gly Phe Ala Asn
        930                 935                 940

Arg Asn Phe Met Gln Leu Ile His Asp Asp Ser Leu Thr Phe Lys Glu
945                 950                 955                 960

Asp Ile Gln Lys Ala Gln Val Ser Gly Gln Gly Asp Ser Leu His Glu
                965                 970                 975

His Ile Ala Asn Leu Ala Gly Ser Pro Ala Ile Lys Lys Gly Ile Leu
            980                 985                 990

Gln Thr Val Lys Val Val Asp Glu Leu Val Lys Val Met Gly Arg His
            995                 1000                1005

Lys Pro Glu Asn Ile Val Ile Glu Met Ala Arg Glu Asn Gln Thr
        1010                1015                1020

Thr Gln Lys Gly Gln Lys Asn Ser Arg Glu Arg Met Lys Arg Ile
        1025                1030                1035

Glu Glu Gly Ile Lys Glu Leu Gly Ser Gln Ile Leu Lys Glu His
        1040                1045                1050

Pro Val Glu Asn Thr Gln Leu Gln Asn Glu Lys Leu Tyr Leu Tyr
        1055                1060                1065

Tyr Leu Gln Asn Gly Arg Asp Met Tyr Val Asp Gln Glu Leu Asp
        1070                1075                1080

Ile Asn Arg Leu Ser Asp Tyr Asp Val Asp His Ile Val Pro Gln
        1085                1090                1095

Ser Phe Leu Lys Asp Asp Ser Ile Asp Asn Lys Val Leu Thr Arg
        1100                1105                1110

Ser Asp Lys Asn Arg Gly Lys Ser Asp Asn Val Pro Ser Glu Glu
        1115                1120                1125

Val Val Lys Lys Met Lys Asn Tyr Trp Arg Gln Leu Leu Asn Ala
        1130                1135                1140

Lys Leu Ile Thr Gln Arg Lys Phe Asp Asn Leu Thr Lys Ala Glu
        1145                1150                1155

Arg Gly Gly Leu Ser Glu Leu Asp Lys Ala Gly Phe Ile Lys Arg
        1160                1165                1170

Gln Leu Val Glu Thr Arg Gln Ile Thr Lys His Val Ala Gln Ile
        1175                1180                1185

Leu Asp Ser Arg Met Asn Thr Lys Tyr Asp Glu Asn Asp Lys Leu
        1190                1195                1200

Ile Arg Glu Val Lys Val Ile Thr Leu Lys Ser Lys Leu Val Ser
        1205                1210                1215

Asp Phe Arg Lys Asp Phe Gln Phe Tyr Lys Val Arg Glu Ile Asn
        1220                1225                1230

Asn Tyr His His Ala His Asp Ala Tyr Leu Asn Ala Val Val Gly
        1235                1240                1245

Thr Ala Leu Ile Lys Lys Tyr Pro Lys Leu Glu Ser Glu Phe Val
        1250                1255                1260

Tyr Gly Asp Tyr Lys Val Tyr Asp Val Arg Lys Met Ile Ala Lys
        1265                1270                1275

Ser Glu Gln Glu Ile Gly Lys Ala Thr Ala Lys Tyr Phe Phe Tyr
        1280                1285                1290

Ser Asn Ile Met Asn Phe Phe Lys Thr Glu Ile Thr Leu Ala Asn
```

```
              1295                1300                1305
Gly Glu Ile Arg Lys Arg Pro Leu Ile Glu Thr Asn Gly Glu Thr
        1310                1315                1320
Gly Glu Ile Val Trp Asp Lys Gly Arg Asp Phe Ala Thr Val Arg
        1325                1330                1335
Lys Val Leu Ser Met Pro Gln Val Asn Ile Val Lys Lys Thr Glu
        1340                1345                1350
Val Gln Thr Gly Gly Phe Ser Lys Glu Ser Ile Leu Pro Lys Arg
        1355                1360                1365
Asn Ser Asp Lys Leu Ile Ala Arg Lys Lys Asp Trp Asp Pro Lys
        1370                1375                1380
Lys Tyr Gly Gly Phe Asp Ser Pro Thr Val Ala Tyr Ser Val Leu
        1385                1390                1395
Val Val Ala Lys Val Glu Lys Gly Lys Ser Lys Lys Leu Lys Ser
        1400                1405                1410
Val Lys Glu Leu Leu Gly Ile Thr Ile Met Glu Arg Ser Ser Phe
        1415                1420                1425
Glu Lys Asn Pro Ile Asp Phe Leu Glu Ala Lys Gly Tyr Lys Glu
        1430                1435                1440
Val Lys Lys Asp Leu Ile Ile Lys Leu Pro Lys Tyr Ser Leu Phe
        1445                1450                1455
Glu Leu Glu Asn Gly Arg Lys Arg Met Leu Ala Ser Ala Gly Glu
        1460                1465                1470
Leu Gln Lys Gly Asn Glu Leu Ala Leu Pro Ser Lys Tyr Val Asn
        1475                1480                1485
Phe Leu Tyr Leu Ala Ser His Tyr Glu Lys Leu Lys Gly Ser Pro
        1490                1495                1500
Glu Asp Asn Glu Gln Lys Gln Leu Phe Val Glu Gln His Lys His
        1505                1510                1515
Tyr Leu Asp Glu Ile Ile Glu Gln Ile Ser Glu Phe Ser Lys Arg
        1520                1525                1530
Val Ile Leu Ala Asp Ala Asn Leu Asp Lys Val Leu Ser Ala Tyr
        1535                1540                1545
Asn Lys His Arg Asp Lys Pro Ile Arg Glu Gln Ala Glu Asn Ile
        1550                1555                1560
Ile His Leu Phe Thr Leu Thr Asn Leu Gly Ala Pro Ala Ala Phe
        1565                1570                1575
Lys Tyr Phe Asp Thr Thr Ile Asp Arg Lys Arg Tyr Thr Ser Thr
        1580                1585                1590
Lys Glu Val Leu Asp Ala Thr Leu Ile His Gln Ser Ile Thr Gly
        1595                1600                1605
Leu Tyr Glu Thr Arg Ile Asp Leu Ser Gln Leu Gly Gly Asp Ser
        1610                1615                1620
Gly Gly Ser Thr Asn Leu Ser Asp Ile Ile Glu Lys Glu Thr Gly
        1625                1630                1635
Lys Gln Leu Val Ile Gln Glu Ser Ile Leu Met Leu Pro Glu Glu
        1640                1645                1650
Val Glu Glu Val Ile Gly Asn Lys Pro Glu Ser Asp Ile Leu Val
        1655                1660                1665
His Thr Ala Tyr Asp Glu Ser Thr Asp Glu Asn Val Met Leu Ser
        1670                1675                1680
Gly Gly Ser Pro Lys Lys Lys Arg Lys Val
        1685                1690
```

<210> SEQ ID NO 3
<211> LENGTH: 5328
<212> TYPE: DNA
<213> ORGANISM: Artificial Sequence
<220> FEATURE:
<223> OTHER INFORMATION: Description of Artificial Sequence: Synthetic
    DNA sequence encoding the TadA-Cas9 D10A-NLS fusion protein

<400> SEQUENCE: 3

| | | | | | |
|---|---|---|---|---|---|
| atgtccgagg | tcgagttctc | tcatgagtac | tggatgaggc | acgctctcac | tcttgctaaa | 60 |
| agagcttggg | acgagagaga | ggttccagtt | ggagctgttt | tggtgcacaa | caaccgtgtg | 120 |
| attggcgaag | gatggaacag | gccaattgga | aggcatgatc | caactgctca | cgctgagatt | 180 |
| atggccctta | gacaaggtgg | actcgtgatg | cagaactaca | ggcttatcga | cgccactctc | 240 |
| tacgtgacac | ttgagccatg | tgttatgtgc | gctggtgcca | tgattcactc | caggattgga | 300 |
| agggttgtgt | cggagctaga | gatgctaaa | actggcgctg | ccggatctct | catggatgtg | 360 |
| cttcatcatc | ctgggatgaa | ccacagggtt | gagatcactg | agggaatcct | tgctgatgag | 420 |
| tgcgctgctc | tcctgtctga | ttttttcagg | atgaggcgtc | aagagatcaa | ggcccagaag | 480 |
| aaggctcagt | cctctactga | ttctggcgga | tcttctggtg | ggtcatctgg | atctgaaacc | 540 |
| cctggaactt | ctgagtccgc | tactccagaa | tcatccggtg | gatctagtgg | tggttctagc | 600 |
| gaggttgagt | cagccacgga | atactggatg | cgtcacgcac | ttactttggc | taagagggct | 660 |
| cgtgatgaga | gggaagttcc | tgttggtgca | gtgctcgtgc | ttaacaacag | agtgatcgga | 720 |
| gaaggctgga | atcgtgctat | cggacttcat | gatcctaccg | cacatgcaga | gatcatggct | 780 |
| ttgaggcaag | gtgggcttgt | catgcaaaat | taccgtctga | tcgacgctac | cttgtacgtc | 840 |
| acattcgagc | cttgcgtgat | gtgtgctggg | gctatgatcc | attctaggat | cggtagagtg | 900 |
| gtgttcggtg | tgaggaatgc | taagacaggt | gctgctggct | cacttatgga | tgtgttgcat | 960 |
| taccccggca | tgaaccaccg | tgtggaaatt | acagagggca | tcttggcaga | tgagtgtgcc | 1020 |
| gctctttgt | gctacttctt | caggatgcca | cgtcaggtgt | tcaacgctca | aaagaaggcc | 1080 |
| caatccagca | ccgattctgg | tggtagtagt | ggtggatctt | ccggatcaga | gactcctggt | 1140 |
| actagtgagt | ctgctacccc | tgaaagtagc | ggaggttcaa | gtggtgggtc | gacaagaag | 1200 |
| tactctatcg | gattggctat | cgggaccaac | tctgttggat | gggctgtgat | cactgacgag | 1260 |
| tacaaggtgc | cctccaagaa | gttcaaggtt | ctcggaaaca | ccgacaggca | ctccatcaag | 1320 |
| aagaacctca | tcggggctct | gcttttcgat | tcaggtgaaa | ctgctgaggc | caccaggctt | 1380 |
| aagagaactg | ctagaagaag | gtacacccgt | aggaagaaca | ggatctgcta | cctccaagag | 1440 |
| atcttctcca | acgagatggc | taaggtggac | gactcattct | tccacaggct | cgaagagtcc | 1500 |
| ttcttggtgg | aagaggataa | gaagcacgag | aggcacccaa | tcttcggaa | cattgtggat | 1560 |
| gaagtggcct | accacgagaa | gtacccaacc | atctaccacc | tgaggaagaa | gctcgttgac | 1620 |
| tccaccgata | aggctgacct | gaggcttatc | taccttgctc | tcgctcacat | gatcaagttc | 1680 |
| cgtgggcact | tccttatcga | agggatctg | aacccagaca | actccgatgt | ggacaagctg | 1740 |
| ttcattcagc | tcgtgcagac | ctacaaccag | ctgttcgaag | agaacccaat | caacgcttct | 1800 |
| ggtgtggacg | ctaaggctat | cctttctgcc | aggctttcca | gtccagaag | gcttgagaac | 1860 |
| ctgattgctc | agcttcctgg | ggagaagaag | aacggacttt | cgggaacct | gatcgccctc | 1920 |
| tctcttggac | ttactcccaa | cttcaagtcc | aacttcgacc | tcgctgagga | tgccaagctt | 1980 |
| cagctctcta | aggataccta | cgatgacgac | ctcgacaacc | tccttgctca | gattggagat | 2040 |

```
cagtacgccg accttttcct cgccgctaaa aacctctctg acgccatcct cctgtccgat    2100
attcttaggg tgaacaccga gatcaccaag gcaccacttt ccgcctctat gatcaagcgt    2160
tacgatgagc accaccagga cctcactttg cttaaggctc ttgttaggca gcagctccca    2220
gagaagtaca aagagatttt cttcgaccag tccaagaacg ggtacgccgg ttatattgat    2280
ggtggggctt ctcaagaaga gttctacaag ttcatcaagc ccatcttgga aaagatggac    2340
gggaccgaag agttgctcgt gaagcttaac cgtgaggacc ttcttaggaa gcagcgaact    2400
ttcgacaacg gctctattcc tcaccagatc caccttggag agctgcacgc tattcttcgt    2460
aggcaagagg acttctaccc attcctcaag gacaaccgtg agaagatcga aagattctc     2520
accttcagga tcccttacta cgtgggacca cttgctaggg gaaattctag gttcgcttgg    2580
atgacccgta agagcgaaga gactatcact ccatggaact tcgaagaggt ggtggacaaa    2640
ggtgctagcg ctcagtcttt catcgagagg atgactaact tcgacaagaa cctgccaaac    2700
gagaaggtgc tcccaaagca ctctctgctc tacgagtact tcaccgtgta caacgagctg    2760
accaaggtca agtatgtgac cgagggaatg cgtaagccag ctttccttag tggtgagcag    2820
aaaaaggcca tcgtggacct cttgttcaag accaatagaa aggtgaccgt gaagcagctc    2880
aaagaggact acttcaaaaa gatcgagtgc ttcgactccg tcgagatctc tggtgttgag    2940
gataggttca acgcctcctt gggaacttac cacgacctcc tcaagatcat caaggataag    3000
gatttcttgg acaacgagga aaacgaggac atcttggagg acatcgtgct caccccttacc  3060
ttgttcgagg atcgagagat gatcgaggaa cgactcaaga cctacgctca cctgttcgat    3120
gacaaggtca tgaagcagtt gaagaggcgt aggtacactg gatggggacg tttgtcccgt    3180
aagctcatta acggaatcag ggacaagcag tccggcaaga ctatcctcga cttcctcaag    3240
tctgatgggt tcgccaaccg taacttcatg cagctcatcc acgacgacag cctgacctttt   3300
aaagaggaca tccaaaaggc ccaggtgtcc ggtcaaggcg attctcttca tgagcacatt    3360
gctaacctcg ctgggtcacc agctatcaag aagggaattc tccagactgt gaaggtcgtg    3420
gacgagttgg ttaaggtgat gggtagacac aagcccgaga acatcgtgat tgagatggct    3480
cgtgagaacc agactactca gaaggggcag aagaactcca gggaacgtat gaagaggatc    3540
gaagagggga tcaaagagct ggggtcccag attcttaaag agcacccagt tgagaacacc    3600
cagctccaga atgagaagct ctacctctac tacctgcaga acggcaggga tatgtacgtg    3660
gaccaagagc tggatatcaa caggctctcc gactacgatg ttgaccacat tgtgccccag    3720
tctttcttga aggacgactc catcgacaac aaggtgctca ccaggtctga taagaaccgt    3780
gggaagtctg acaacgtgcc atctgaagag gtcgtgaaga agatgaagaa ctactggcgt    3840
cagctcctca acgccaagct tattactcag aggaagttcg acaacttgac caaggctgag    3900
cgtggtggac tttccgaact tgataaggcc ggattcatca gaggcagct cgtggaaact    3960
aggcagatca ctaagcacgt ggcccagatc ttggactcta ggatgaacac caagtacgac    4020
gagaacgaca agctcatccg tgaggtgaag gtcatcaccc tcaagagcaa gctggtgtcc    4080
gatttcagaa aggacttcca attctacaag gtgagagaga tcaacaacta ccatcacgct    4140
cacgacgctt accttaacgc tgttgttgga accgctctca tcaaaaagta ccccaagctc    4200
gagtccgagt tcgtgtacgg tgattacaag gtgtacgacg tgcgtaagat gatcgccaag    4260
tcagagcaag agatcggtaa ggctaccgcc aagtatttct tctactccaa catcatgaat    4320
ttcttcaaga ctgagatcac cctcgccaac ggggagatta gaaagaggcc acttatcgag    4380
```

```
actaacggcg agactggtga atcgtgtgg gataaggga gagacttcgc cactgtgcgt    4440
aaggtgttgt ctatgccaca ggtgaacatc gtcaagaaaa ccgaggttca gaccggcggg    4500
ttctccaaag aatctatcct tccaaagagg aactccgaca gctgatcgc taggaagaag    4560 gattgggacc caaaaagta cggtgggttc gattctccaa ccgtggctta ctctgttctt    4620
gttgtggcca aggttgagaa ggggaagtct aagaaactca gtccgtgaa agagctgctc    4680 gggatcacta tcatggaaag gtccagcttc gagaagaatc caatcgattt cctcgaggcc    4740
aagggctaca agaggtgaa gaaggacctt atcatcaagc tccccaagta cagcctcttc    4800
gagttggaga acgacgtaa gaggatgctt gcttctgctg gggaacttca gaagggaaac    4860
gaactcgctc tgccctctaa gtacgtgaac ttcctgtacc tcgcttccca ctacgagaag    4920
cttaagggat ctccagagga taacgagcaa aagcagcttt tcgtcgagca gcacaagcac    4980
tacctcgacg agattatcga gcagatctcc gagttctcca gcgtgtgat tctcgctgat    5040 gccaacttgg acaaggtgtt gagcgcttac aacaagcacc gtgacaagcc aattagagag    5100
caggctgaga acatcatcca cctgttcact ctcaccaacc ttggtgctcc agctgccttt    5160
aagtacttcg ataccaccat cgaccgtaag aggtacacct ccaccaaaga ggttttggac    5220
gctaccctta tccaccagtc catcactgga ctttacgaga ctaggatcga cctctcacag    5280
ctcggtggtg actctggtgg atcaccaaag aagaagagga aggtctaa              5328
```

<210> SEQ ID NO 4
<211> LENGTH: 1775
<212> TYPE: PRT
<213> ORGANISM: Artificial Sequence
<220> FEATURE:
<223> OTHER INFORMATION: Description of Artificial Sequence: Synthetic
      TadA-Cas9 D10A-NLS fusion protein

<400> SEQUENCE: 4

```
Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
            180                 185                 190
```

```
Gly Gly Ser Ser Gly Gly Ser Ser Glu Val Glu Phe Ser His Glu Tyr
            195                 200                 205
Trp Met Arg His Ala Leu Thr Leu Ala Lys Arg Ala Arg Asp Glu Arg
210                 215                 220
Glu Val Pro Val Gly Ala Val Leu Val Leu Asn Asn Arg Val Ile Gly
225                 230                 235                 240
Glu Gly Trp Asn Arg Ala Ile Gly Leu His Asp Pro Thr Ala His Ala
            245                 250                 255
Glu Ile Met Ala Leu Arg Gln Gly Leu Val Met Gln Asn Tyr Arg
            260                 265                 270
Leu Ile Asp Ala Thr Leu Tyr Val Thr Phe Glu Pro Cys Val Met Cys
            275                 280                 285
Ala Gly Ala Met Ile His Ser Arg Ile Gly Arg Val Val Phe Gly Val
            290                 295                 300
Arg Asn Ala Lys Thr Gly Ala Ala Gly Ser Leu Met Asp Val Leu His
305                 310                 315                 320
Tyr Pro Gly Met Asn His Arg Val Glu Ile Thr Glu Gly Ile Leu Ala
            325                 330                 335
Asp Glu Cys Ala Ala Leu Leu Cys Tyr Phe Phe Arg Met Pro Arg Gln
            340                 345                 350
Val Phe Asn Ala Gln Lys Lys Ala Gln Ser Ser Thr Asp Ser Gly Gly
            355                 360                 365
Ser Ser Gly Gly Ser Ser Gly Ser Glu Thr Pro Gly Thr Ser Glu Ser
    370                 375                 380
Ala Thr Pro Glu Ser Ser Gly Gly Ser Ser Gly Gly Ser Asp Lys Lys
385                 390                 395                 400
Tyr Ser Ile Gly Leu Ala Ile Gly Thr Asn Ser Val Gly Trp Ala Val
            405                 410                 415
Ile Thr Asp Glu Tyr Lys Val Pro Ser Lys Lys Phe Lys Val Leu Gly
            420                 425                 430
Asn Thr Asp Arg His Ser Ile Lys Lys Asn Leu Ile Gly Ala Leu Leu
            435                 440                 445
Phe Asp Ser Gly Glu Thr Ala Glu Ala Thr Arg Leu Lys Arg Thr Ala
450                 455                 460
Arg Arg Arg Tyr Thr Arg Arg Lys Asn Arg Ile Cys Tyr Leu Gln Glu
465                 470                 475                 480
Ile Phe Ser Asn Glu Met Ala Lys Val Asp Asp Ser Phe Phe His Arg
            485                 490                 495
Leu Glu Glu Ser Phe Leu Val Glu Glu Asp Lys Lys His Glu Arg His
            500                 505                 510
Pro Ile Phe Gly Asn Ile Val Asp Glu Val Ala Tyr His Glu Lys Tyr
            515                 520                 525
Pro Thr Ile Tyr His Leu Arg Lys Lys Leu Val Asp Ser Thr Asp Lys
530                 535                 540
Ala Asp Leu Arg Leu Ile Tyr Leu Ala Leu Ala His Met Ile Lys Phe
545                 550                 555                 560
Arg Gly His Phe Leu Ile Glu Gly Asp Leu Asn Pro Asp Asn Ser Asp
            565                 570                 575
Val Asp Lys Leu Phe Ile Gln Leu Val Gln Thr Tyr Asn Gln Leu Phe
            580                 585                 590
Glu Glu Asn Pro Ile Asn Ala Ser Gly Val Asp Ala Lys Ala Ile Leu
            595                 600                 605
Ser Ala Arg Leu Ser Lys Ser Arg Arg Leu Glu Asn Leu Ile Ala Gln
```

```
                610             615             620
Leu Pro Gly Glu Lys Lys Asn Gly Leu Phe Gly Asn Leu Ile Ala Leu
625             630             635             640

Ser Leu Gly Leu Thr Pro Asn Phe Lys Ser Asn Phe Asp Leu Ala Glu
                645             650             655

Asp Ala Lys Leu Gln Leu Ser Lys Asp Thr Tyr Asp Asp Leu Asp
                660             665             670

Asn Leu Leu Ala Gln Ile Gly Asp Gln Tyr Ala Asp Leu Phe Leu Ala
                675             680             685

Ala Lys Asn Leu Ser Asp Ala Ile Leu Leu Ser Asp Ile Leu Arg Val
                690             695             700

Asn Thr Glu Ile Thr Lys Ala Pro Leu Ser Ala Ser Met Ile Lys Arg
705             710             715             720

Tyr Asp Glu His His Gln Asp Leu Thr Leu Leu Lys Ala Leu Val Arg
                725             730             735

Gln Gln Leu Pro Glu Lys Tyr Lys Glu Ile Phe Phe Asp Gln Ser Lys
                740             745             750

Asn Gly Tyr Ala Gly Tyr Ile Asp Gly Gly Ala Ser Gln Glu Glu Phe
                755             760             765

Tyr Lys Phe Ile Lys Pro Ile Leu Glu Lys Met Asp Gly Thr Glu Glu
                770             775             780

Leu Leu Val Lys Leu Asn Arg Glu Asp Leu Leu Arg Lys Gln Arg Thr
785             790             795             800

Phe Asp Asn Gly Ser Ile Pro His Gln Ile His Leu Gly Glu Leu His
                805             810             815

Ala Ile Leu Arg Arg Gln Glu Asp Phe Tyr Pro Phe Leu Lys Asp Asn
                820             825             830

Arg Glu Lys Ile Glu Lys Ile Leu Thr Phe Arg Ile Pro Tyr Tyr Val
                835             840             845

Gly Pro Leu Ala Arg Gly Asn Ser Arg Phe Ala Trp Met Thr Arg Lys
                850             855             860

Ser Glu Glu Thr Ile Thr Pro Trp Asn Phe Glu Glu Val Val Asp Lys
865             870             875             880

Gly Ala Ser Ala Gln Ser Phe Ile Glu Arg Met Thr Asn Phe Asp Lys
                885             890             895

Asn Leu Pro Asn Glu Lys Val Leu Pro Lys His Ser Leu Leu Tyr Glu
                900             905             910

Tyr Phe Thr Val Tyr Asn Glu Leu Thr Lys Val Lys Tyr Val Thr Glu
                915             920             925

Gly Met Arg Lys Pro Ala Phe Leu Ser Gly Glu Gln Lys Lys Ala Ile
                930             935             940

Val Asp Leu Leu Phe Lys Thr Asn Arg Lys Val Thr Val Lys Gln Leu
945             950             955             960

Lys Glu Asp Tyr Phe Lys Lys Ile Glu Cys Phe Asp Ser Val Glu Ile
                965             970             975

Ser Gly Val Glu Asp Arg Phe Asn Ala Ser Leu Gly Thr Tyr His Asp
                980             985             990

Leu Leu Lys Ile Ile Lys Asp Lys Asp Phe Leu Asp Asn Glu Glu Asn
                995             1000            1005

Glu Asp Ile Leu Glu Asp Ile Val Leu Thr Leu Thr Leu Phe Glu
        1010            1015            1020

Asp Arg Glu Met Ile Glu Glu Arg Leu Lys Thr Tyr Ala His Leu
        1025            1030            1035
```

```
Phe Asp Asp Lys Val Met Lys Gln Leu Lys Arg Arg Arg Tyr Thr
    1040            1045                1050

Gly Trp Gly Arg Leu Ser Arg Lys Leu Ile Asn Gly Ile Arg Asp
    1055            1060                1065

Lys Gln Ser Gly Lys Thr Ile Leu Asp Phe Leu Lys Ser Asp Gly
    1070            1075                1080

Phe Ala Asn Arg Asn Phe Met Gln Leu Ile His Asp Asp Ser Leu
    1085            1090                1095

Thr Phe Lys Glu Asp Ile Gln Lys Ala Gln Val Ser Gly Gln Gly
    1100            1105                1110

Asp Ser Leu His Glu His Ile Ala Asn Leu Ala Gly Ser Pro Ala
    1115            1120                1125

Ile Lys Lys Gly Ile Leu Gln Thr Val Lys Val Val Asp Glu Leu
    1130            1135                1140

Val Lys Val Met Gly Arg His Lys Pro Glu Asn Ile Val Ile Glu
    1145            1150                1155

Met Ala Arg Glu Asn Gln Thr Thr Gln Lys Gly Gln Lys Asn Ser
    1160            1165                1170

Arg Glu Arg Met Lys Arg Ile Glu Glu Gly Ile Lys Glu Leu Gly
    1175            1180                1185

Ser Gln Ile Leu Lys Glu His Pro Val Glu Asn Thr Gln Leu Gln
    1190            1195                1200

Asn Glu Lys Leu Tyr Leu Tyr Tyr Leu Gln Asn Gly Arg Asp Met
    1205            1210                1215

Tyr Val Asp Gln Glu Leu Asp Ile Asn Arg Leu Ser Asp Tyr Asp
    1220            1225                1230

Val Asp His Ile Val Pro Gln Ser Phe Leu Lys Asp Asp Ser Ile
    1235            1240                1245

Asp Asn Lys Val Leu Thr Arg Ser Asp Lys Asn Arg Gly Lys Ser
    1250            1255                1260

Asp Asn Val Pro Ser Glu Glu Val Val Lys Lys Met Lys Asn Tyr
    1265            1270                1275

Trp Arg Gln Leu Leu Asn Ala Lys Leu Ile Thr Gln Arg Lys Phe
    1280            1285                1290

Asp Asn Leu Thr Lys Ala Glu Arg Gly Gly Leu Ser Glu Leu Asp
    1295            1300                1305

Lys Ala Gly Phe Ile Lys Arg Gln Leu Val Glu Thr Arg Gln Ile
    1310            1315                1320

Thr Lys His Val Ala Gln Ile Leu Asp Ser Arg Met Asn Thr Lys
    1325            1330                1335

Tyr Asp Glu Asn Asp Lys Leu Ile Arg Glu Val Lys Val Ile Thr
    1340            1345                1350

Leu Lys Ser Lys Leu Val Ser Asp Phe Arg Lys Asp Phe Gln Phe
    1355            1360                1365

Tyr Lys Val Arg Glu Ile Asn Asn Tyr His His Ala His Asp Ala
    1370            1375                1380

Tyr Leu Asn Ala Val Val Gly Thr Ala Leu Ile Lys Lys Tyr Pro
    1385            1390                1395

Lys Leu Glu Ser Glu Phe Val Tyr Gly Asp Tyr Lys Val Tyr Asp
    1400            1405                1410

Val Arg Lys Met Ile Ala Lys Ser Glu Gln Glu Ile Gly Lys Ala
    1415            1420                1425
```

Thr Ala Lys Tyr Phe Phe Tyr Ser Asn Ile Met Asn Phe Phe Lys
1430                1435                1440

Thr Glu Ile Thr Leu Ala Asn Gly Glu Ile Arg Lys Arg Pro Leu
1445                1450                1455

Ile Glu Thr Asn Gly Glu Thr Gly Glu Ile Val Trp Asp Lys Gly
1460                1465                1470

Arg Asp Phe Ala Thr Val Arg Lys Val Leu Ser Met Pro Gln Val
1475                1480                1485

Asn Ile Val Lys Lys Thr Glu Val Gln Thr Gly Gly Phe Ser Lys
1490                1495                1500

Glu Ser Ile Leu Pro Lys Arg Asn Ser Asp Lys Leu Ile Ala Arg
1505                1510                1515

Lys Lys Asp Trp Asp Pro Lys Lys Tyr Gly Gly Phe Asp Ser Pro
1520                1525                1530

Thr Val Ala Tyr Ser Val Leu Val Val Ala Lys Val Glu Lys Gly
1535                1540                1545

Lys Ser Lys Lys Leu Lys Ser Val Lys Glu Leu Leu Gly Ile Thr
1550                1555                1560

Ile Met Glu Arg Ser Ser Phe Glu Lys Asn Pro Ile Asp Phe Leu
1565                1570                1575

Glu Ala Lys Gly Tyr Lys Glu Val Lys Lys Asp Leu Ile Ile Lys
1580                1585                1590

Leu Pro Lys Tyr Ser Leu Phe Glu Leu Glu Asn Gly Arg Lys Arg
1595                1600                1605

Met Leu Ala Ser Ala Gly Glu Leu Gln Lys Gly Asn Glu Leu Ala
1610                1615                1620

Leu Pro Ser Lys Tyr Val Asn Phe Leu Tyr Leu Ala Ser His Tyr
1625                1630                1635

Glu Lys Leu Lys Gly Ser Pro Glu Asp Asn Glu Gln Lys Gln Leu
1640                1645                1650

Phe Val Glu Gln His Lys His Tyr Leu Asp Glu Ile Ile Glu Gln
1655                1660                1665

Ile Ser Glu Phe Ser Lys Arg Val Ile Leu Ala Asp Ala Asn Leu
1670                1675                1680

Asp Lys Val Leu Ser Ala Tyr Asn Lys His Arg Asp Lys Pro Ile
1685                1690                1695

Arg Glu Gln Ala Glu Asn Ile Ile His Leu Phe Thr Leu Thr Asn
1700                1705                1710

Leu Gly Ala Pro Ala Ala Phe Lys Tyr Phe Asp Thr Thr Ile Asp
1715                1720                1725

Arg Lys Arg Tyr Thr Ser Thr Lys Glu Val Leu Asp Ala Thr Leu
1730                1735                1740

Ile His Gln Ser Ile Thr Gly Leu Tyr Glu Thr Arg Ile Asp Leu
1745                1750                1755

Ser Gln Leu Gly Gly Asp Ser Gly Gly Ser Pro Lys Lys Lys Arg
1760                1765                1770

Lys Val
1775

<210> SEQ ID NO 5
<211> LENGTH: 183
<212> TYPE: DNA
<213> ORGANISM: Artificial Sequence
<220> FEATURE:
<223> OTHER INFORMATION: Description of Artificial Sequence: Synthetic LIN5 sgRNA1

<400> SEQUENCE: 5
ggagtgatca aaagtcccac atcgatcagg tgatatatag cagcttagtt tatataatga    60
tagagtcgac atagcgattg cctgacgatg aaattaagaa gttttagagc tagaaatagc   120
aagttaaaat aaggctagtc cgttatcaac ttgaaaaagt ggcaccgagt cggtgctttt   180
ttt                                                                 183

<210> SEQ ID NO 6
<211> LENGTH: 183
<212> TYPE: DNA
<213> ORGANISM: Artificial Sequence
<220> FEATURE:
<223> OTHER INFORMATION: Description of Artificial Sequence: Synthetic
      LIN5 sgRNA2

<400> SEQUENCE: 6
ggagtgatca aaagtcccac atcgatcagg tgatatatag cagcttagtt tatataatga    60
tagagtcgac atagcgattg ttcatcgtca ggtaatacat gttttagagc tagaaatagc   120
aagttaaaat aaggctagtc cgttatcaac ttgaaaaagt ggcaccgagt cggtgctttt   180
ttt                                                                 183

<210> SEQ ID NO 7
<211> LENGTH: 183
<212> TYPE: DNA
<213> ORGANISM: Artificial Sequence
<220> FEATURE:
<223> OTHER INFORMATION: Description of Artificial Sequence: Synthetic
      ALS2 sgRNA1

<400> SEQUENCE: 7
ggagtgatca aaagtcccac atcgatcagg tgatatatag cagcttagtt tatataatga    60
tagagtcgac atagcgattg caagtgccga ggaggatgat gttttagagc tagaaatagc   120
aagttaaaat aaggctagtc cgttatcaac ttgaaaaagt ggcaccgagt cggtgctttt   180
ttt                                                                 183

<210> SEQ ID NO 8
<211> LENGTH: 183
<212> TYPE: DNA
<213> ORGANISM: Artificial Sequence
<220> FEATURE:
<223> OTHER INFORMATION: Description of Artificial Sequence: Synthetic
      ALS2 sgRNA2

<400> SEQUENCE: 8
ggagtgatca aaagtcccac atcgatcagg tgatatatag cagcttagtt tatataatga    60
tagagtcgac atagcgattg catcctcctc ggcacttgac gttttagagc tagaaatagc   120
aagttaaaat aaggctagtc cgttatcaac ttgaaaaagt ggcaccgagt cggtgctttt   180
ttt                                                                 183

<210> SEQ ID NO 9
<211> LENGTH: 183
<212> TYPE: DNA
<213> ORGANISM: Artificial Sequence
<220> FEATURE:
<223> OTHER INFORMATION: Description of Artificial Sequence: Synthetic
      ALS2 sgRNA3

<400> SEQUENCE: 9

```
ggagtgatca aaagtcccac atcgatcagg tgatatatag cagcttagtt tatataatga    60
tagagtcgac atagcgattg ttaccggtca agtgccgagg gttttagagc tagaaatagc   120
aagttaaaat aaggctagtc cgttatcaac ttgaaaaagt ggcaccgagt cggtgctttt   180
ttt                                                                 183
```

<210> SEQ ID NO 10
<211> LENGTH: 183
<212> TYPE: DNA
<213> ORGANISM: Artificial Sequence
<220> FEATURE:
<223> OTHER INFORMATION: Description of Artificial Sequence: Synthetic
      ALS2 S640 sgRNA1

<400> SEQUENCE: 10

```
ggagtgatca aaagtcccac atcgatcagg tgatatatag cagcttagtt tatataatga    60
tagagtcgac atagcgattg gcaccgccac tgggaatcat gttttagagc tagaaatagc   120
aagttaaaat aaggctagtc cgttatcaac ttgaaaaagt ggcaccgagt cggtgctttt   180
ttt                                                                 183
```

<210> SEQ ID NO 11
<211> LENGTH: 183
<212> TYPE: DNA
<213> ORGANISM: Artificial Sequence
<220> FEATURE:
<223> OTHER INFORMATION: Description of Artificial Sequence: Synthetic
      ALS2 S640 sgRNA2

<400> SEQUENCE: 11

```
ggagtgatca aaagtcccac atcgatcagg tgatatatag cagcttagtt tatataatga    60
tagagtcgac atagcgattg tctttgaaag caccgccact gttttagagc tagaaatagc   120
aagttaaaat aaggctagtc cgttatcaac ttgaaaaagt ggcaccgagt cggtgctttt   180
ttt                                                                 183
```

<210> SEQ ID NO 12
<211> LENGTH: 183
<212> TYPE: DNA
<213> ORGANISM: Artificial Sequence
<220> FEATURE:
<223> OTHER INFORMATION: Description of Artificial Sequence: Synthetic
      ALS2 S640 sgRNA3

<400> SEQUENCE: 12

```
ggagtgatca aaagtcccac atcgatcagg tgatatatag cagcttagtt tatataatga    60
tagagtcgac atagcgattg ctaccgatga ttcccagtgg gttttagagc tagaaatagc   120
aagttaaaat aaggctagtc cgttatcaac ttgaaaaagt ggcaccgagt cggtgctttt   180
ttt                                                                 183
```

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      LIN5 target site

<400> SEQUENCE: 13

```
cctgacgatg aaattaagaa agg                                            23
```

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      LIN5 target site

<400> SEQUENCE: 14
cctgacgatg aaattaagaa agg                                          23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      LIN5 target site

<400> SEQUENCE: 15
ccgatgtatt acctgacgat gaa                                          23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      LIN5 target site

<400> SEQUENCE: 16
cctgacgatg aaattaagaa agg                                          23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      LIN5 target site

<400> SEQUENCE: 17
cctgacgatg aaattaagaa agg                                          23

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      WT target sequence

<400> SEQUENCE: 18
atgtattacc tgacgatgaa                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      line 1 target sequence

<400> SEQUENCE: 19
atgtattayc tgaygatgaa                                              20

```
<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      line 2 target sequence

<400> SEQUENCE: 20
atgtattacy tgaygatgaa                                                20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      line 3 target sequence

<400> SEQUENCE: 21
atgtattayy tgaygatgaa                                                20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      line 4 target sequence

<400> SEQUENCE: 22
atgtattacc tgacratraa                                                20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      line 5 target sequence

<400> SEQUENCE: 23
atgtattacc tracratraa                                                20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      line 6 target sequence

<400> SEQUENCE: 24
atgtattacc taacaataaa                                                20

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      target site

<400> SEQUENCE: 25
tgctattacc ggtcaagtgc cgaggaggat gattggtac                           39

<210> SEQ ID NO 26
```

```
<211> LENGTH: 39
<212> TYPE: DNA
<213> ORGANISM: Artificial Sequence
<220> FEATURE:
<223> OTHER INFORMATION: Description of Artificial Sequence: Synthetic
      target site

<400> SEQUENCE: 26
gtaccaatca tcctcctcgg cacttgaccg gtaatagca                              39

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      target site

<400> SEQUENCE: 27
tgttctaccg atgattccca gtggcggtgc tttcaaaga                              39

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      target site

<400> SEQUENCE: 28
tctttgaaag caccgccact gggaatcatc ggtagaaca                              39

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Synthetic
      P184 ref

<400> SEQUENCE: 29
tgctattacc ggtcaagtgc cgaggaggat gattggtac                              39

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      S640 ref

<400> SEQUENCE: 30
tgttctaccg atgattccca gtggcggtgc tttcaaaga                              39

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence: Synthetic
      S640 ref

<400> SEQUENCE: 31
tgttctaccg atgattccca gtggcggtgc tttcaaaga                              39

<210> SEQ ID NO 32
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 32

Ser Pro Lys Lys Lys Arg Lys Val Glu Ala Ser
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 33

Ser Gly Ser Glu Thr Pro Gly Thr Ser Glu Ser Ala Thr Pro Glu Ser
1               5                   10                  15

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 34

Lys Ser Gly Ser Glu Thr Pro Gly Thr Ser Glu Ser Ala Thr Pro Glu
1               5                   10                  15

Ser

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 35
cactattggc atgtatcaca c                                            21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      reversed primer

<400> SEQUENCE: 36
gtgatgctga gatcccttta ac                                           22

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 37

His His His His His His
```

```
<210> SEQ ID NO 38
<211> LENGTH: 35
<212> TYPE: PRT
<213> ORGANISM: Artificial Sequence
<220> FEATURE:
<223> OTHER INFORMATION: Description of Artificial Sequence: Synthetic
      linker
<220> FEATURE:
<221> NAME/KEY: MISC_FEATURE
<222> LOCATION: (1)..(35)
<223> OTHER INFORMATION: This sequence may encompass 1-7 "Glu Ala Ala
      Ala Lys" repeating units
<220> FEATURE:
<223> OTHER INFORMATION: See specification as filed for detailed
      description of substitutions and preferred embodiments

<400> SEQUENCE: 38

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
            20                  25                  30

Ala Ala Lys
        35

<210> SEQ ID NO 39
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(29)
<223> OTHER INFORMATION: Any amino acid
<220> FEATURE:
<221> NAME/KEY: MISC_FEATURE
<222> LOCATION: (4)..(29)
<223> OTHER INFORMATION: This region may encompass 23-26 residues
<220> FEATURE:
<221> NAME/KEY: MOD_RES
<222> LOCATION: (32)..(35)
<223> OTHER INFORMATION: Any amino acid
<220> FEATURE:
<221> NAME/KEY: MISC_FEATURE
<222> LOCATION: (32)..(35)
<223> OTHER INFORMATION: This region may encompass 2-4 residues

<400> SEQUENCE: 39

His Xaa Glu Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Pro Cys Xaa
            20                  25                  30

Xaa Xaa Xaa Cys
        35

<210> SEQ ID NO 40
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MISC_FEATURE
<222> LOCATION: (1)..(35)
<223> OTHER INFORMATION: This sequence may encompass 1-7 "Gly Gly Gly
      Gly Ser" repeating units
<220> FEATURE:
<223> OTHER INFORMATION: See specification as filed for detailed
      description of substitutions and preferred embodiments

<400> SEQUENCE: 40

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Ser Gly Gly
            20                  25                  30

Gly Gly Ser
        35

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(21)
<223> OTHER INFORMATION: This sequence may encompass 1-7 "Gly Gly Ser"
      repeating units
<220> FEATURE:
<223> OTHER INFORMATION: See specification as filed for detailed
      description of substitutions and preferred embodiments

<400> SEQUENCE: 41

Gly Gly Ser Gly Gly Ser Gly Gly Ser Gly Gly Ser Gly Gly Ser Gly
1               5                   10                  15

Gly Ser Gly Gly Ser
            20

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(7)
<223> OTHER INFORMATION: This sequence may encompass 1-7 residues
<220> FEATURE:
<223> OTHER INFORMATION: See specification as filed for detailed
      description of substitutions and preferred embodiments

<400> SEQUENCE: 42

Gly Gly Gly Gly Gly Gly Gly
1               5

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cctgatgatg aaattaagaa                                             20
```

```
<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cttgatgatg aaattaagaa                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tttgatgatg aaattaagaa                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tctgacgatg aaattaagaa                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cctgatgatg aaattaagaa                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tctgacgatg aaattaagaa                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tttgatgatg aaattaagaa                                              20

<210> SEQ ID NO 50
```

```
<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tctgatgatg aaattaagaa                                                   20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
atgtattacc tgacaataaa                                                   20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
atgtattacc tgacaatgaa                                                   20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
atgtattacc taacaataaa                                                   20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cctggcgatg aaattaagaa                                                   20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cctgacggtg aaattaagaa                                                   20

<210> SEQ ID NO 56
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cctgatgatg aaattaagaa                                                     20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cctggcgatg aaattaagaa                                                     20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cctgatggtg aaattaagaa                                                     20

<210> SEQ ID NO 59
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tgctattacc ggtcaagtgt cgaggaggat gattggtac                                39

<210> SEQ ID NO 60
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tgctattacc ggtcaagtgc tgaggaggat gattggtac                                39

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tgctattacc ggtcaagtgt tgaggaggat gattggtac                                39

<210> SEQ ID NO 62
<211> LENGTH: 39
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 62
tgctattacc ggttaagtgc cgaggaggat gattggtac                                39

<210> SEQ ID NO 63
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tgctattacc ggtcaagtgc cgaagaggat gattggtac                                39

<210> SEQ ID NO 64
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tgctattacc ggtcaagtgc cgagaaggat gattggtac                                39

<210> SEQ ID NO 65
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tgctattacc ggtcaagtgc cgaggaagat gattggtac                                39

<210> SEQ ID NO 66
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tgctattacc ggtcaagtgc cgaggaggat aattggtac                                39

<210> SEQ ID NO 67
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tgctattatc ggtcaagtgc cgaggaggat gattggtac                                39

<210> SEQ ID NO 68
<211> LENGTH: 39
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 68
tgctattact ggtcaagtgc cgaggaggat gattggtac                                39

<210> SEQ ID NO 69
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tgctattatt ggtcaagtgc cgaggaggat gattggtac                                39

<210> SEQ ID NO 70
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tgctattacc ggttaagtgc cgaggaggat gattggtac                                39

<210> SEQ ID NO 71
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tgctattacc ggtcaagtgt cgaggaggat gattggtac                                39

<210> SEQ ID NO 72
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tgctattacc ggtcaagtgc tgaggaggat gattggtac                                39

<210> SEQ ID NO 73
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tgctattacc ggtcaagtgt tgaggaggat gattggtac                                39

<210> SEQ ID NO 74
<211> LENGTH: 39
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 74
tgttctaccg ataattccca gtggcggtgc tttcaaaga                              39

<210> SEQ ID NO 75
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tgttctaccg atgattccca atggcggtgc tttcaaaga                              39

<210> SEQ ID NO 76
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tgttctaccg atgattccca gtagcggtgc tttcaaaga                              39

<210> SEQ ID NO 77
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tgttctaccg atgattccca gtgacggtgc tttcaaaga                              39

<210> SEQ ID NO 78
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tgttctaccg atgattccca gtggcagtgc tttcaaaga                              39

<210> SEQ ID NO 79
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tgttctaccg atgattccca gtggcgatgc tttcaaaga                              39

<210> SEQ ID NO 80
<211> LENGTH: 39
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 80
tgttctaccg atgattccca gtggcggtac tttcaaaga          39

<210> SEQ ID NO 81
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tgttctaccg atgattccca atggcggtgc tttcaaaga          39

<210> SEQ ID NO 82
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tgttctaccg atgattccca gtagcggtgc tttcaaaga          39

<210> SEQ ID NO 83
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tgttctaccg atgattccca gtgacggtgc tttcaaaga          39

<210> SEQ ID NO 84
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tgttctaccg atgattccca gtggcagtgc tttcaaaga          39

<210> SEQ ID NO 85
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tgttctaccg atgattccca gtggcgatgc tttcaaaga          39

<210> SEQ ID NO 86
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 86
tgttctaccg atgattccca gtggcggtac tttcaaaga                                39

<210> SEQ ID NO 87
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
tgttctaccg atgattccca gtggcggtgc tttcaaaaa                                39

<210> SEQ ID NO 88
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tgttttaccg atgattccca gtggcggtgc tttcaaaga                                39

<210> SEQ ID NO 89
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tgttctatcg atgattccca gtggcggtgc tttcaaaga                                39

<210> SEQ ID NO 90
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tgttctactg atgattccca gtggcggtgc tttcaaaga                                39

<210> SEQ ID NO 91
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tgttctaccg atgatttcca gtggcggtgc tttcaaaga                                39

<210> SEQ ID NO 92
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 92
tgttctaccg atgattctca gtggcggtgc tttcaaaga                          39

<210> SEQ ID NO 93
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tgttctaccg atgattccta gtggcggtgc tttcaaaga                          39

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Gly Glu Val Pro Arg Arg Met Ile Gly
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Pro Met Ile Pro Ser Gly Gly Ala Phe Leu
1               5                   10
```